(12) United States Patent
Sugawara

(10) Patent No.: US 10,322,211 B2
(45) Date of Patent: Jun. 18, 2019

(54) METHOD FOR CONTROLLING WORK TIME FOR FORMING SHAPE OF BIPHASIC SELF-SETTING CALCIUM PHOSPHATE

(71) Applicants: MEDICAL U & A, INC., Osaka-shi, Osaka (JP); FRONTIER SCIENCE CORPORATION, Tokyo (JP)

(72) Inventor: Akiyoshi Sugawara, Tokyo (JP)

(73) Assignees: MEDICAL U & A, INC., Osaka-shi, Osaka (JP); FRONTIER SCIENCE CORPORATION, Minato-ku, Tokyo (JP)

(*) Notice: Subject to any disclaimer, the term of this patent is extended or adjusted under 35 U.S.C. 154(b) by 0 days.

(21) Appl. No.: 15/123,533

(22) PCT Filed: Mar. 5, 2015

(86) PCT No.: PCT/JP2015/001210
§ 371 (c)(1),
(2) Date: Sep. 2, 2016

(87) PCT Pub. No.: WO2015/133149
PCT Pub. Date: Sep. 11, 2015

(65) Prior Publication Data
US 2017/0072104 A1    Mar. 16, 2017

(30) Foreign Application Priority Data

Mar. 6, 2014 (JP) .................................. 2014-044449
Sep. 13, 2014 (JP) .................................. 2014-187138

(51) Int. Cl.
*C04B 12/02* (2006.01)
*C04B 28/34* (2006.01)
(Continued)

(52) U.S. Cl.
CPC ............ *A61L 27/50* (2013.01); *A61K 6/0038* (2013.01); *A61K 6/0643* (2013.01);
(Continued)

(58) Field of Classification Search
None
See application file for complete search history.

(56) References Cited

U.S. PATENT DOCUMENTS

| 8,557,038 | B2 | 10/2013 | Chow et al. | |
| 2005/0074415 | A1* | 4/2005 | Chow | A61K 6/0038 424/49 |
| 2012/0165822 | A1* | 6/2012 | Yetkinler | A61B 17/8822 606/93 |

FOREIGN PATENT DOCUMENTS

| JP | 06-329405 A | 11/1994 |
| JP | 2003-052804 A | 2/2003 |

OTHER PUBLICATIONS

Tagaya, M., et al., "Development of Self-Setting Te-CP/ α-TCP Cement for Pulpotomy", Dental Materials Journal, vol. 24 (4), 2005, 555-561 (7 pages).
(Continued)

*Primary Examiner* — Ernst V Arnold
*Assistant Examiner* — Kyung S Chang
(74) *Attorney, Agent, or Firm* — Sughrue Mion, PLLC

(57) ABSTRACT

Biphasic self-setting calcium phosphate (SSCP) used for bone graft material and dental material applications having shape formability, shape retentivity, and bone replacement properties in addition to biocompatibility, safety, non-infectiousness, and absence of outflow, wherein the work time for forming the shape of a kneaded material obtained by kneading biphasic SSCP powder and biphasic SSCP liquid is controlled. A method for controlling the work time for forming the shape of biphasic SSCP in which the moldable work time from the start of kneading to the setting of the
(Continued)

kneaded material is adjusted to within a range of from 10 seconds to 600 seconds by kneading a biphasic SSCP powder and biphasic SSCP liquid, the biphasic SSCP powder comprising tetracalcium phosphate and α-tricalcium phosphate and the biphasic SSCP liquid comprising a phosphoric acid aqueous solution containing a calcium component.

7 Claims, 45 Drawing Sheets

(51) Int. Cl.
- C04B 22/06 (2006.01)
- C04B 40/00 (2006.01)
- A61K 6/00 (2006.01)
- A61K 6/06 (2006.01)
- A61L 27/50 (2006.01)
- A61L 27/12 (2006.01)
- A61L 27/02 (2006.01)
- C04B 111/00 (2006.01)

(52) U.S. Cl.
CPC .............. *A61L 27/025* (2013.01); *A61L 27/12* (2013.01); *C04B 12/02* (2013.01); *C04B 28/34* (2013.01); *C04B 28/348* (2013.01); *C04B 40/0032* (2013.01); *A61L 2400/06* (2013.01); *A61L 2430/02* (2013.01); *C04B 2111/00836* (2013.01)

(56) References Cited

OTHER PUBLICATIONS

Tagaya, M., et al., "Development f α-TCP/Te-CP cement for Pulpotomy", Asahi Univ., vol. 22, No. 2, 2010 (4 pages).

Takeda, S., et al, "Application of α-TCP/Te-CP cement to pulp capping materials", Asahi Univ., vol. 31, No. 5, Sep. 25, 2012 (5 pages).

Sugawara, A., et al, "Single-solid-ingredient-based Calcium Phosphate Cements", 2007 IADR 2007 (3 pages).

Mostafa, A., "Rapid-setting Tetracalcium Phosphate (TTCP)-based Cements", 88th IADR, 2010 (3 pages).

Sugawara, A., et al, "Histopathological study of rapid setting TTCP-cements used for bone defect", 91th IADR, Mar. 23, 2013 (3 pages).

Shimada, Y., et al., "Properties of Injectable Apatite-Forming Premixed Cements", Journal of Research of the National Institute of Standards and Technology, vol. 115, No. 4, Jul. 2010, 233-241 (9 pages).

* cited by examiner

METHOD FOR CONTROLLING WORK TIME FOR FORMING SHAPE OF BIPHASIC SELF-SETTING CALCIUM PHOSPHATE

CROSS REFERENCE TO RELATED APPLICATIONS

This application is a National Stage of International Application No. PCT/JP2015/001210, filed Mar. 5, 2015, claiming priorities based on Japanese Patent Application Nos. 2014-044449, filed Mar. 6, 2014 and 2014-187138, filed Sep. 13, 2014, the contents of all of which are incorporated herein by reference in their entirety.

TECHNICAL FIELD

The present invention relates to a method for controlling work time for shape-forming low-temperature hydroxyapatite produced from biphasic self-setting calcium phosphate (hereinafter referred to as "SSCP"), and to biphasic SSCP having shape formability and shape maintainability in which the work time is controlled.

BACKGROUND ART

Known techniques of setting a calcium phosphate compound include the following.

For example, it has been previously reported that a set material is obtained by mixing a mixture of tetracalcium phosphate (hereinafter referred to as "TTCP") and α-tricalcium phosphate (hereinafter referred to as "α-TCP") with a liquid agent (Patent Literature 1). The first prior art already published states that a set material having a three-dimensional shape is obtained by using a raw material powder containing TTCP and/or α-TCP and having a Ca/P ratio (molar ratio of calcium to phosphorus) of 1.40 to 2.0, including a first step of forming a layer composed of the raw material powder and a second step of bringing a reactive solution that chemically reacts with the raw material powder into contact with at least a part of the layer to set the raw material powder, and repeating the first step and the second step to thereby build up a plurality of the layers (claim 1 of Patent Literature 1).

However, the structural formula of TTCP is $Ca_4(PO_4)_2O$, and the Ca/P ratio of TTCP is 2.00. Further, the structural formula of α-TCP is $Ca_3(PO_4)_2$, and the Ca/P ratio of α-TCP is 1.50.

Therefore, when only TTCP and α-TCP are mixed at any ratio, the Ca/P ratio of the mixture does not have a value of less than 1.50.

However, all the lower limits of the Ca/P ratio disclosed in the first prior art are 1.40, and there is no description in which the lower limit is 1.50.

The case where the lower limit of the Ca/P ratio of the mixture is less than 1.50 is limited to a case where a component other than TTCP and α-TCP is contained. Therefore, it is unknown from the first prior art what kind of result is obtained when a raw material consisting of TTCP and α-TCP (hereinafter referred to as a "biphasic SSCP powder portion") is used.

Further, there is also description that a mixture can be used as a liquid agent to be used in the first prior art, the mixture being obtained by adding, to water, an organic acid such as citric acid, an organic acid salt such as sodium salt and potassium salt of the organic acid, an inorganic acid such as phosphoric acid, an inorganic acid salt such as sodium phosphate, sodium carbonate, potassium phosphate, and potassium carbonate, a pH adjuster, a thickener, an X-ray contrast medium, an antibacterial agent, a monosaccharide such as glucose and fructose, a disaccharide such as saccharose and maltose, a polysaccharide such as cellulose, chitin, and chitosan, a bone morphogenetic protein such as BMP, various preparations such as prostaglandin, and the like (Patent Literature 1, paragraph [0077]).

However, in the first prior art, there is no description about the setting time when the mixture and the liquid agent are mixed.

On the other hand, as a second prior art, there is proposed a method of producing TTCP including producing a raw material slurry by synthesizing a raw material component containing a calcium-supplying raw material and a phosphorus-supplying raw material by a wet process, then drying the raw material slurry, baking the dried raw material at 400 to 1200° C., and firing the baked raw material at 1300 to 1500° C. (Patent Literature 2).

The second prior art describes that monophasic TTCP is obtained.

Further, the second prior art describes calcium phosphate cement (CPC) obtained by mixing the resulting monophasic TTCP and dicalcium phosphate anhydrous (DCPA) at a molar ratio of 1:1.

The second prior art also describes that a set material is obtained by mixing the CPC with water.

Further, as a third prior art, there is also described a method of kneading a paste of TTCP and a paste of DCPA to set the pastes (Non Patent Literature 1).

As a fourth prior art, there is described a method of separately preparing a TTCP powder, an α-TCP powder, and a β-TCP powder and kneading each of the powder with a saturated aqueous solution of dicalcium phosphate dihydrate (hereinafter referred to as "DCPD") to set the kneaded mixture (Non Patent Literature 2).

As a fifth prior art, there is described a method of kneading a TTCP powder and a saturated MCPM phosphoric acid solution to set the kneaded mixture (Non Patent Literature 3).

However, in the first to the fifth prior arts, when a biphasic SSCP powder portion is used, it is unknown how much the setting time of the kneaded material containing the biphasic SSCP powder portion will be.

Next, a prior art which has disclosed a TTCP/α-TCP solid solution will be described.

A sixth prior art discloses that a cement powder is obtained by mechanically mixing calcium carbonate (hereinafter referred to as "$CaCO_3$") and DCPD at a molar ratio of 5:6, heating the mixture for 5 hours at 1500° C., and grinding the resulting fired block.

Further, it is also disclosed that a set material is obtained by kneading the cement powder and a liquid agent (Non Patent Literature 4).

Furthermore, a seventh prior art also discloses that the ratio of Ca to P contained in a fired block can be adjusted in a range of 1.5 to 2.0 using $CaCO_3$ and DCPD (Non Patent Literature 5).

The liquid agent used in the sixth prior art is either (1) 1 M orthophosphoric acid aqueous solution (powder-liquid ratio: 1.5), (2) 1 M sodium dihydrogenphosphate aqueous solution (powder-liquid ratio: 1.5), (3) 1 M sodium dihydrogenphosphate aqueous solution (powder-liquid ratio: 2.0), (4) 2 M sodium dihydrogenphosphate aqueous solution (powder-liquid ratio 1.5), (5) 2 M sodium dihydrogenphosphate aqueous solution (powder-liquid ratio: 2.0), (6) 1 M citric acid aqueous solution (powder-liquid ratio: 2.0), (7) 1

M citric acid aqueous solution (powder-liquid ratio: 2.5), or (8) 2 M citric acid aqueous solution (powder-liquid ratio: 1.5).

Further, the liquid agent used in the seventh prior art is 1 M sodium dihydrogenphosphate aqueous solution, and 0.6 ml of the liquid agent is used relative to 1.0 g of a powder portion containing 95 weights of TTCP/α-TCP solid solution and 5 weight % of apatite.

The sixth prior art also describes the setting time of the above kneaded material.

Specifically, it is described that, by kneading the cement powder and a liquid agent, the setting time of a kneaded material will be about 2 minutes when the liquid agent (8) is used, and the setting time of a kneaded material will be about 52 minutes when the liquid agent (2) is used.

However, it is described that, even when any of the above (1) to (8) is selected as a liquid agent, diffraction peaks derived from raw materials are detected for 72 hours from the start of kneading.

Further, the seventh prior art describes that, even after a lapse of 28 days, diffraction peaks derived from raw materials are detected in the resulting set material.

Thus, the sixth and seventh prior arts describe that, when a TTCP/α-TCP solid solution is used, a long period of time is required until setting reaction is completed.

Further, an eighth prior art discloses that a set material is obtained by mixing (A) a powder portion obtained by mixing nonstoichiometric TTCP with 2 M trisodium citrate aqueous solution at a powder-liquid ratio of 2.5 and (B) a liquid agent obtained by saturating 1.05 mol/L phosphoric acid aqueous solution having a pH of 2.1 with monocalcium phosphate monohydrate (hereinafter referred to as "MCPM") (Non Patent Literature 6).

However, the eighth prior art does not specifically disclose the nonstoichiometric TTCP other than it has a Ca/P ratio of 1.81. Therefore, it is unknown from the eighth prior art how the nonstoichiometric TTCP has been obtained.

Further, the eighth prior art does not describe the information about how much the setting time is when the nonstoichiometric TTCP is mixed with the saturated MCPM phosphoric acid aqueous solution.

On the other hand, a ninth prior art describes that a set material is obtained by kneading a first paste and a second paste (Patent Literature 3).

Here, the first paste contains at least one of dicalcium phosphate anhydrous (hereinafter referred to as "DCPA") and DCPD, and water, and the second paste is a nonaqueous paste containing TTCP.

The ninth prior art, which describes work time and setting time, also discloses that the setting time of a set material obtained by kneading the first paste and the second paste can be adjusted between 3 minutes and 26 minutes, and the work time can be adjusted between 1.3 minutes and 10 minutes.

However, in the case of the ninth prior art, single TTCP and at least one of DCPA and DCPD are used, and the information about the case where a biphasic SSCP powder portion is used is not disclosed.

Therefore, it is unknown that, when the biphasic SSCP powder portion is used, how much the work time and setting time will be.

Further, the ninth prior art also discloses that the set material obtained by kneading the first paste and the second paste can be used for bone grafting.

By the way, it is required that a bone graft material used for the purpose of grafting into bone defects be not only compatible and safe in that the material does not harm a body in which it is grafted but also not susceptible to infection by a disease germ, a virus, and the like. Further, it is required that the bone graft material have such physical and chemical stabilities that, after being grafted into bone defects, the bone graft material is difficult to outflow, dissolve, or move from the bone defects.

However, it is not necessarily sufficient that the bone graft material has compatibility, safety, non-susceptibility to infection, physical stability, and chemical stability described above. In addition to these properties, shape formability and shape maintainability are also required.

The shape formability refers to properties in which a material can be formed into an ideal shape to bone defects, and the shape maintainability refers to properties in which a material has physical properties that can endure a physical load required during grafting, and a set material thereof can maintain the shape for a certain period of time required until the bone is regenerated.

Furthermore, a bone graft material is also required to have bone replaceability in which the material itself is replaced by bone with the lapse of time in the body.

However, if calcium phosphate compounds other than hydroxyapatite (hereinafter referred to as "HA"), for example, unreacted TTCP and α-TCP, remain in the set material described in the first to the ninth prior arts described above, there will be a problem that the unreacted TTCP and α-TCP each chemically dissolve in the body fluid in the body.

This is because HA is supersaturated in the body fluid in the body, while all the calcium phosphate compounds are undersaturated in the body fluid in the body except that octacalcium phosphate (hereinafter referred to as "OCP") is saturated in the body fluid in the body, and therefore, the calcium phosphate compounds other than HA dissolve in the body fluid in the body except OCP.

There is also a fundamental problem that, in the process of bone replacement, when calcium ions and phosphate ions which are ionized by dissolution are combined, partial bone formation occurs in a part that has reprecipitated as a minute crystal of HA which is the calcium phosphate compound that is the most stable in the body, and α-TCP or TTCP itself does not directly undergo bone replacement.

An ideal bone graft material has properties called osteoconductivity in which, when the graft material is grafted in the body, it is directly bonded to existing bone without the intervention of connective tissue.

However, although high-temperature HA obtained by firing, which is typified by the set material described in the first prior art, has osteoconductivity, it is not replaced by bone itself in the body, but it only compensates for the bone defects for a certain period of time as a space-making material with which the space is simply filled.

Therefore, in the process of bone regeneration progressing with time, the bond of the high-temperature HA to surrounding bone is gradually lost, and it has a risk of outflowing from a body as foreign matter someday.

Further, in the case of a set material in which unreacted TTCP and α-TCP remain, a loss by the dissolution in the body fluid occurs. Therefore, a hole or a gap is inevitably produced in the set material, and even if a new bone is formed in a part of the set material as a result, anticipation of the final shape is difficult.

CITATION LIST

Patent Literature

Patent Literature 1:
JP 2003-52804A

Patent Literature 2:
JP H06-329405A
Patent Literature 3:
U.S. Pat. No. 8,557,038B Non Patent Literature Non Patent Literature 1:
J RES Natl Inst Stand Technol. 2010 July; 115(4): 233 to 241
Non Patent Literature 2:
Akiyoshi Sugawara, Kenji Fujikawa, Satoshi Hirayama, Shozo Takagi, and Lairence C, Chow: Single-solid-ingredient-based calcium phosphate cements, 39th IADR, 2007.
Non Patent Literature 3:
A. Mostafa, Shozo Takagi, and Laurence C. Chow: Rapid setting tetracalcium phosphate cements, 88th IADR, 2010.
Non Patent Literature 4:
The journal of the Japanese Society for Dental Materials and Devices 31 (5), 481, Sep. 25, 2012
Non Patent Literature 5:
Dental Materials & Appliances 22 (2), 77, Mar. 20, 2003
Non Patent Literature 6:
Akiyoshi Sugawara, Kenji Fujikawa, Makoto Hayashi, Hidehiro Ogata, Sakurako Iwata, Masumi Oki, Bunnai Ogiso, Shozo Takagi, and Laurence C Chow: Histopathological study of a rapid setting tetracalcium phosphate cements used for bone defect, 91th IADR, Mar. 23, 2013.

SUMMARY OF INVENTION

Technical Problem

By the way, according to the sixth prior art that has mentioned the setting time of a kneaded material, a set material is obtained in about 2 minutes after the start of kneading by using 2 M citric acid aqueous solution at a powder-liquid ratio of 1.5 relative to a TTCP/$\alpha$-TCP solid solution.

According to the investigation by the present inventor, it has been verified that when the TTCP/$\alpha$-TCP solid solution and the citric acid aqueous solution are kneaded, a set material is certainly obtained in a short time.

However, the present inventor has found that the set material may be obtained as a result of the reaction between a calcium component contained in the TTCP/$\alpha$-TCP solid solution and citric acid to form a chelate compound.

If the reaction of converting TTCP and $\alpha$-TCP to HA is accelerated by using a citric acid aqueous solution, it is difficult to theoretically describe the contents of the sixth prior art that has reported that the reaction of converting TTCP and $\alpha$-TCP to HA requires a long period of time regardless of using a citric acid aqueous solution.

Conversely, the phenomena can be smoothly described if it is considered that the following two reactions are competing: the reaction (1) in which a chelate compound such as calcium citrate is produced when the solid solution and the citric acid aqueous solution are kneaded, and the produced chelate compound is precipitated to set the kneaded material; and the reaction (2) of converting TTCP and $\alpha$-TCP to HA.

Since priority is given to the reaction of producing a chelate compound when the citric acid aqueous solution is used, a set material is quickly obtained by a pseudo-setting reaction.

On the other hand, the reaction of converting TTCP and $\alpha$-TCP to HA, which is a reaction different from the reaction of producing a chelate compound, requires a long period of time for the reaction.

Since the solid solution does not easily dissolve in the citric acid aqueous solution, when the solid solution and the citric acid aqueous solution are kneaded, the surface of the particles of the solid solution will be covered with a chelate compound such as calcium citrate.

As a result, the contact of TTCP and $\alpha$-TCP remaining in the inner part of the particles with the citric acid aqueous solution is difficult. Therefore, there are no contradictions in the contents of the report of the sixth prior art, which reports that the reaction time of converting TTCP and $\alpha$-TCP to HA is not reduced regardless of using a citric acid aqueous solution.

However, even if a set material is obtained by kneading a TTCP/$\alpha$-TCP solid solution and a citric acid aqueous solution, the setting reaction is a pseudoreaction due to the production of a chelate compound such as calcium citrate.

Further, a chelate compound such as calcium citrate and unreacted TTCP and $\alpha$-TCP are not directly replaced by existing bone and have the properties of being dissolved in the body fluid.

Therefore, if the set material obtained using citric acid is used for a defect produced in bone, there will be even a danger of producing a hole in the defect produced in the bone.

On the other hand, even if a calcium phosphate compound can be set by kneading a powder portion and a liquid portion, it will be difficult to apply the kneaded material to the application of a hard tissue regeneration material if the kneaded material cannot be formed into a shape due to excessively low or excessively high viscosity of the resulting kneaded material.

Further, it is not sufficient that the kneaded material can be only formed into a shape. If work time in which the kneaded material can be shape-formed cannot be controlled in a desired range, the work time cannot be controlled in a time range generally required for bone grafting, when the kneaded material is applied to the application of bone grafting. As a result, it is difficult to apply the kneaded material to the application of a hard tissue regeneration material.

An object of the present invention is to control the work time for shape-forming a biphasic self-setting calcium phosphate (SSCP), that is, a low-temperature HA obtained by kneading a biphasic SSCP powder portion and a biphasic SSCP liquid portion, which is used for the application of a hard tissue regeneration material having shape formability, shape maintainability, and bone replaceability in addition to biocompatibility, safety, non-infectiousness, and absence of outflow.

Solution to Problem

As a result of extensive and intensive studies to achieve the above object, the present inventor has found that a method for controlling the work time for shape-forming a biphasic SSCP is suitable for the object of the present invention, the biphasic SSCP powder portion comprising TTCP and $\alpha$-TCP, a calcium component contained in the biphasic SSCP liquid portion comprising at least one selected from the group consisting of calcium hydroxide (hereinafter referred to as "Ca(OH)$_2$"), calcium oxide (hereinafter referred to as "CaO"), and CaCO$_3$, wherein the work time that is required for shape-forming, from the start of kneading to the setting of a kneaded material, is adjusted in a range of 10 seconds to 600 seconds by kneading the biphasic SSCP powder portion and the biphasic SSCP liquid portion at a temperature in a range of 10 to 40° C. The present invention has been completed on the basis of these findings.

Specifically, the present invention provides

[1] A method for controlling work time for shape-forming a biphasic SSCP, the work time being from the start of kneading a biphasic SSCP powder portion and a biphasic SSCP liquid portion to the setting of the biphasic SSCP, the biphasic SSCP powder portion comprising TTCP and α-TCP, the biphasic SSCP liquid portion comprising a phosphoric acid aqueous solution containing a calcium component, the calcium component contained in the biphasic SSCP liquid portion comprising at least one selected from the group consisting of $Ca(OH)_2$, CaO, and $CaCO_3$, wherein the work time that is required for shape-forming, from the start of kneading to the setting of a kneaded material, is adjusted in a range of 10 seconds to 600 seconds by kneading the biphasic SSCP powder portion and the biphasic SSCP liquid portion at a temperature in a range of 10 to 40° C.

Further, one of the present inventions provides

[2] The method for controlling the work time for shape-forming a biphasic SSCP according to the above [1], wherein the biphasic SSCP contains a sodium citrate compound comprising at least one selected from the group consisting of monosodium citrate, disodium citrate, and trisodium citrate; and the sodium citrate compound is added to at least one of the biphasic SSCP powder portion and the biphasic SSCP liquid portion.

Further, one of the present inventions provides

[3] The method for controlling the work time for shape-forming a biphasic SSCP according to the above [1] or [2], wherein the biphasic SSCP powder portion is prepared by grinding a heated mixture obtained by heating a mixture comprising $CaCO_3$ and DCPs for 3 to 12 hours at a temperature range of 1200 to 1600° C., and the weight % of the $CaCO_3$ based on the sum of the weight of the $CaCO_3$ and the weight of the DCPs is in a range of 26.9 to 42.3 weight %.

Further, one of the present inventions provides

[4] The method for controlling the work time for shape-forming a biphasic SSCP according to the above [1] or [2], wherein the biphasic SSCP powder portion is a solid solution comprising TTCP and α-TCP, and the weight fraction of α-TCP in the solid solution is in a range of 10 to 90%.

Further, one of the present inventions provides

[5] The method for controlling the work time for shape-forming a biphasic SSCP according to any of the above [1] to [4], wherein the biphasic SSCP liquid portion is a phosphoric acid aqueous solution containing calcium, and the concentration of calcium in the aqueous solution is in a range of $1.0 \times 10^{-3}$ mol/L to 1.1 mol/L.

Further, one of the present inventions provides

[6] The method for controlling the work time for shape-forming a biphasic SSCP according to any of the above [1] to [5], wherein the powder-liquid ratio of the biphasic SSCP powder portion to the biphasic SSCP liquid portion is in a range of 1.0 to 5.0 based on the weight of the powder portion to the weight of the liquid portion.

Further, one of the present inventions provides

[7] The method for controlling the work time for shape-forming a biphasic SSCP according to any of the above [1] to [6], wherein the biphasic SSCP liquid portion is an aqueous solution containing 3 to 45 weight % of phosphoric acid.

Further, one of the present inventions provides

[8] The method for controlling the work time for shape-forming a biphasic SSCP according to any of the above [1] to [7], wherein when the phosphorus concentration (mol/L) of the biphasic SSCP liquid portion is taken along the x-axis and the calcium concentration (mol/L) of the biphasic SSCP liquid portion is taken along the y-axis, the values (x, y) of the phosphorus concentration and the calcium concentration of the biphasic SSCP liquid portion are included in the range of a triangle obtained by connecting the 3 points of (2.96, 1.09), (0.592, 0.218), and (7.38, 0.25) by straight lines, respectively.

Further, the present invention provides

[9] Biphasic SSCP having a work time that is required for shape-forming in a range of 10 seconds to 600 seconds at a temperature in a range of 10 to 40° C., the work time being from the start of kneading a biphasic SSCP powder portion and a biphasic SSCP liquid portion to the setting of the resulting kneaded material, wherein the biphasic SSCP powder portion comprises TTCP and α-TCP;

the biphasic SSCP liquid portion comprises a phosphoric acid aqueous solution containing a calcium component; and the calcium component contained in the biphasic SSCP liquid portion comprises at least one selected from the group consisting of $Ca(OH)_2$, CaO, and $CaCO_3$, and wherein the biphasic SSCP is prepared by kneading the biphasic SSCP powder portion and the biphasic SSCP liquid portion.

Further, one of the present inventions provides

[10] The biphasic SSCP according to the above [9], wherein the biphasic SSCP contains a sodium citrate compound comprising at least one selected from the group consisting of monosodium citrate, disodium citrate, and trisodium citrate; and the sodium citrate compound is added to at least one of the biphasic SSCP powder portion and the biphasic SSCP liquid portion.

Further, one of the present inventions provides

[11] The biphasic SSCP according to the above [9] or [10], wherein the biphasic SSCP powder portion is a solid solution comprising TTCP and α-TCP, and the weight fraction of α-TCP in the solid solution is in a range of 10 to 90%.

Further, one of the present inventions provides

[12] The biphasic SSCP according to any of the above [9] to [11], wherein the biphasic SSCP liquid portion is a calcium phosphate aqueous solution, and the concentration of calcium in the aqueous solution is in a range of $1.0 \times 10^{-3}$ mol/L to 1.1 mol/L.

Further, one of the present inventions provides

[13] The biphasic SSCP according to any of the above [9] to [12], wherein the powder-liquid ratio of the biphasic SSCP powder portion to the biphasic SSCP liquid portion is in a range of 1.0 to 5.0 based on the weight of the powder portion to the weight of the liquid portion.

Further, one of the present inventions provides

[14] The biphasic SSCP according to any of the above [9] to [13], wherein the biphasic SSCP liquid portion is an aqueous solution containing 3 to 45 weight % of phosphoric acid.

Further, one of the present inventions provides

[15] The biphasic SSCP according to any of the above [9] to [14], wherein when the phosphorus concentration (mol/L) of the biphasic SSCP liquid portion is taken along the x-axis and the calcium concentration (mol/L) of the biphasic SSCP liquid portion is taken along the y-axis, the values (x, y) of the phosphorus concentration and the calcium concentration of the biphasic SSCP liquid portion are included in the range of a triangle obtained by connecting the three points of (2.96, 1.09), (0.592, 0.218), and (7.38, 0.25) by straight lines, respectively.

Further, the present invention provides

[16] A hard tissue regeneration material comprising the biphasic SSCP according to any of the above [9] to [15].

Further, one of the present inventions provides

[17] The hard tissue regeneration material according to the above [16], wherein the hard tissue regeneration material contains a shape forming agent, and the shape forming agent is in a range of 0.01 to 3.0 parts by weight based on 100 parts by weight of the biphasic SSCP.

Further, one of the present inventions provides

[18] The hard tissue regeneration material according to the above [16] or [17], wherein the hard tissue regeneration material contains at least one selected from the group consisting of a coloring agent, a preservative, a germicide, an osteoinductive factor, a blood product, a porogen, an antibiotic substance, a radiopaque agent, and a strength reinforcing fiber material.

Further, the present invention provides

[19] A hard tissue regeneration material kit comprising the biphasic SSCP powder portion and the biphasic SSCP liquid portion according to any of the above [9] to [15].

Further, the present invention provides

[20] A composition for relieving dentin hypersensitivity to teeth comprising the biphasic SSCP powder portion and the biphasic SSCP liquid portion according to any of the above [9] to [15].

Further, the present invention provides

[21] A composition for filling a dental caries portion comprising the biphasic SSCP powder portion and the biphasic SSCP liquid portion according to any of the above [9] to [15].

Further, the present invention provides

[22] A composition for accelerating remineralization to tooth enamel comprising the biphasic SSCP powder portion and the biphasic SSCP liquid portion according to any of the above [9] to [15].

Further, the present invention provides

[23] A dental pulp capping composition for covering an exposed portion of dental pulp comprising the biphasic SSCP powder portion and the biphasic SSCP liquid portion according to any of the above [9] to [15].

Further, the present invention provides

[24] A covering composition for covering tooth perforation comprising the biphasic SSCP powder portion and the biphasic SSCP liquid portion according to any of the above [9] to [15].

Further, the present invention provides

[25] A dental root canal filling composition comprising the biphasic SSCP powder portion and the biphasic SSCP liquid portion according to any of the above [9] to [15].

Advantageous Effects of Invention

According to the control method of the present invention, the work time that is required for shape-forming, from the start of kneading to the setting of a kneaded material, can be adjusted in a range of 10 seconds to 600 seconds by kneading the biphasic SSCP powder portion and the biphasic SSCP liquid portion at a temperature in a range of 10 to 40° C.

Thus, the kneaded material can be formed into a desired shape before the kneaded material sets.

Moreover, since the kneaded material can be set in a relatively short time according to the control method of the present invention, when the biphasic SSCP is applied to the application of hard tissue regeneration materials such as a bone graft material and a dental material, it is not necessary to keep patients waiting for a long time until the biphasic SSCP sets, and physical pain and mental anguish of the patients can be significantly reduced.

Further, when the biphasic SSCP powder portion and the biphasic SSCP liquid portion which constitute biphasic SSCP are kneaded, the setting will start at room temperature, and the biphasic SSCP sets after the lapse of a definite period of time to form a hard tissue regeneration material.

The hard tissue regeneration material is paste-like before it sets, and it is excellent in shape formability since it can easily form a certain shape.

By using the biphasic SSCP obtained by the present invention, a portion that has undergone bone grafting in the body of a patient who has undergone bone grafting can be restored to a level that cannot be practically distinguished from the existing bone of the patient.

Further, the biphasic SSCP of the present invention, which is used for the application of hard tissue regeneration materials such as a bone graft material and a dental material, is excellent in bioaffinity since the biphasic SSCP after setting has a hydrogen ion concentration (pH) in the range close to that of the body fluid.

Further, the biphasic SSCP of the present invention is excellent in safety and non-susceptibility to infection since the incorporation of impurities, germs, viruses, and the like can be prevented in the production process.

The biphasic SSCP according to the present invention is set by kneading and produces a HA crystal with low crystallinity in a relatively short time, which is the same as HA which is the main constituent of the mineral of bone and teeth. Since HA is generally supersaturated in the body fluid, HA does not naturally dissolve in the body fluid. Therefore, a product obtained from the biphasic SSCP does not dissolve in the body fluid.

On the other hand, since calcium phosphates, calcium citrate, and the like other than HA are undersaturated in the body fluid, they dissolve in a body.

Therefore, since the biphasic SSCP of the present invention sets through the work time that is set between 10 seconds and 600 seconds while keeping the formed shape thereof, it is not outflowed into and lost by the body fluid and can maintain the shape.

Further, since the biphasic SSCP after setting has sufficient strength and can maintain physical properties that can respond to external mechanical strength to bone defects from the early stage of grafting, it has a character that shows sufficient shape maintainability required for the activities of daily life.

Further, the hard tissue regeneration material using the biphasic SSCP of the present invention has a character that replaceable bone formation by osteoblast starting from the absorption by osteoclast is made while maintaining the shape formed first.

After the hard tissue regeneration material is replaced by new bone, the new bone is not recognized as foreign matter in a body, and the defects that have been recovered by the hard tissue regeneration material can be recovered to the state to the same degree as the healthy existing surrounding bone.

As described above, the hard tissue regeneration material using the biphasic SSCP of the present invention has excellent properties in that when it is used for the application of grafting and filling into bone defects, it has shape formability, sets in the body, and is absorbed and replaced by own bone while keeping the shape thereof.

DESCRIPTION OF EMBODIMENTS

Figure 1:
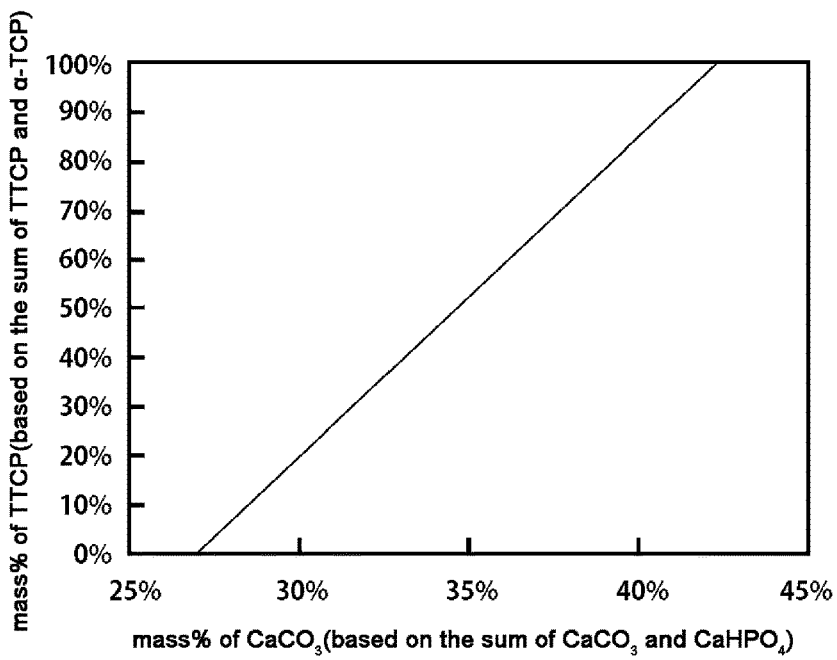
FIG. 1 is a graph showing the relationship between the mass % of $CaCO_3$ as a raw material and the mass % of TTCP contained in the resulting biphasic SSCP.

First, a biphasic SSCP powder portion will be described.

The biphasic SSCP powder portion comprises TTCP and α-TCP.

The biphasic SSCP powder portion which can be used includes a mixture of TTCP and α-TCP (in the present invention, referred to as a "TTCP/α-TCP mixture") and a solid solution of TTCP and α-TCP (in the present invention, referred to as a "TTCP/α-TCP solid solution").

The biphasic SSCP powder portion used in the present invention preferably comprises a TTCP/α-TCP solid solution from the point of view of supplying products having uniform physical properties.

Examples of the raw materials of the biphasic SSCP powder portion used in the present invention include $CaCO_3$ and DCPs.

Examples of the $CaCO_3$ which can be used include a naturally occurring product obtained by physically grinding natural materials such as limestone and a shell and selecting the particle size and a chemically synthesized product which is chemically synthesized.

The $CaCO_3$ used in the present invention is preferably a chemically synthesized product from the point of view of purity.

The DCPs mean dicalcium phosphates and may be at least one of DCPA and DCPD. Since the DCPA and DCPD are commercially available, commercially available products can be arbitrarily selected and used.

The $CaCO_3$ and DCPs used in the present invention are each preferably used in a powder state. Further, the shape of each powder is not particularly limited.

The shape of the powder may be spherical or fractural.

The $CaCO_3$ and DCPs used in the present invention are more preferably dried in advance.

Examples of the methods of drying each of the $CaCO_3$ and DCPs include a method of putting each of the $CaCO_3$ and DCPs in a general-purpose oven and heat-treating the same at a temperature of 100° C. or more.

The heating temperature of each of the $CaCO_3$ and DCPA is preferably in a range of 100 to 120° C.

Further, the heating time of each of the $CaCO_3$ and DCPA is preferably in a range of 1 to 10 hours, more preferably in a range of 2 to 3 hours.

Since the mixing weight ratio of the $CaCO_3$ to DCPs can be accurately measured by previously drying the $CaCO_3$ and DCPs used in the present invention, it is possible to provide the biphasic SSCP having homogeneous quality.

When the $CaCO_3$ and DCPs are dried, the $CaCO_3$ and DCPs may be independently dried, or the both may be mixed and then dried.

Note that, when the both are mixed and then dried, a small amount of each of the $CaCO_3$ and DCPs before drying is divided and measured for the difference between the weight before drying and the weight after drying, thereby capable of grasping the amount of water contained in each of the $CaCO_3$ and DCPs.

By taking the water content into consideration, the mixing ratio of the $CaCO_3$ to DCPs can be accurately calculated.

With respect to the mixing ratio of the $CaCO_3$ to DCPs used in the present invention, the weight % of the $CaCO_3$ is in a range of 26.9 to 42.3 weight % based on the sum of the weight of the $CaCO_3$ and the weight of DCPA.

When the weight % of the $CaCO_3$ is in a range of 26.9 to 42.3 weight %, a biphasic SSCP powder portion comprising a TTCP/α-TCP solid solution can be obtained.

The weight % of the $CaCO_3$ is preferably in a range of 30.0 to 40.0 weight %.

Further, the molar ratio of calcium (Ca) to phosphorus (P) contained in the TTCP/α-TCP solid solution obtained by the production method of the present invention can be set as desired in a range of more than 1.50 and less than 2.00 based on Ca/P.

The Ca/P represents the proportion in which the denominator represents the number of moles of phosphorus, and the numerator represents the number of moles of calcium.

When the mixing ratio of $CaCO_3$ to DCPA is changed, the mixing ratio of α-TCP to TTCP contained in the resulting TTCP/α-TCP solid solution will change. The relationship about this change is summarized in Table 1.

According to the present invention, a TTCP/α-TCP solid solution showing a desired value of Ca/P in a range of more than 1.50 and less than 2.00 can be obtained as shown in Table 1.

This range is preferably in a range of 1.52 to 1.97.

After the mixing step is completed, the liquid and the mixture of $CaCO_3$ and DCPs are separated by a method such as filtration in the case of a wet blending method.

In the filtration, a filtering medium such as filter paper and a filter cloth can be used.

Examples of the method of performing the filtration include a method in which a filtering medium is installed in a filtration container, the liquid and the mixture of $CaCO_3$ and DCPA are injected into the inner part of the filtration container, and the filtration container is decompressed from the opposite side of the place where the filtering medium of the filtration container is installed; and a method in which

TABLE 1

| Raw Material | | | | Molar Ratio | Composition of TTCP/α-TCP Solid Solution | | | |
|---|---|---|---|---|---|---|---|---|
| $CaCO_3$ mass % | $CaHPO_4$ mass % | $CaCO_3$ molar % | $CaHPO_4$ molar % | Ca/P | $Ca_3(PO_4)_2$ molar % | $Ca_4(PO_4)_2O$ molar % | $Ca_3(PO_4)_2$ mass % | $Ca_4(PO_4)_2O$ mass % |
| 26.9 | 73.1 | 33.3 | 66.7 | 1.5002 | 99.95 | 0.05 | 99.9 | 0.1 |
| 27.7 | 72.3 | 34.3 | 65.7 | 1.5211 | 95.8 | 4.2 | 95.1 | 4.9 |
| 28.5 | 71.5 | 35.2 | 64.8 | 1.5424 | 91.5 | 8.5 | 90.1 | 9.9 |
| 29.3 | 70.7 | 36.1 | 63.9 | 1.5642 | 87.2 | 12.8 | 85.2 | 14.8 |
| 30.1 | 69.9 | 37.0 | 63.0 | 1.5865 | 82.7 | 17.3 | 80.2 | 19.8 |
| 31.0 | 69.1 | 37.9 | 62.1 | 1.6093 | 78.1 | 21.9 | 75.2 | 24.8 |
| 31.8 | 68.2 | 38.8 | 61.2 | 1.6327 | 73.5 | 26.5 | 70.1 | 29.9 |
| 32.6 | 67.4 | 39.6 | 60.4 | 1.6566 | 68.7 | 31.3 | 65.0 | 35.0 |
| 33.4 | 66.6 | 40.5 | 59.5 | 1.6811 | 63.8 | 36.2 | 59.9 | 40.1 |
| 34.2 | 65.8 | 41.4 | 58.6 | 1.7062 | 58.8 | 41.2 | 54.7 | 45.3 |
| 35.0 | 65.0 | 42.3 | 57.7 | 1.7320 | 53.6 | 46.4 | 49.5 | 50.5 |
| 35.8 | 64.2 | 43.1 | 56.9 | 1.7584 | 48.3 | 51.7 | 44.2 | 55.8 |
| 36.6 | 63.4 | 44.0 | 56.0 | 1.7854 | 42.9 | 57.1 | 38.9 | 61.1 |
| 37.4 | 62.6 | 44.8 | 55.2 | 1.8132 | 37.4 | 62.6 | 33.6 | 66.4 |
| 38.2 | 61.8 | 45.7 | 54.3 | 1.8417 | 31.7 | 68.3 | 28.2 | 71.8 |
| 39.1 | 61.0 | 46.6 | 53.4 | 1.8709 | 25.8 | 74.2 | 22.8 | 77.2 |
| 39.9 | 60.1 | 47.4 | 52.6 | 1.9010 | 19.8 | 80.2 | 17.3 | 82.7 |
| 40.7 | 59.3 | 48.2 | 51.8 | 1.9318 | 13.6 | 86.4 | 11.8 | 88.2 |
| 41.5 | 58.5 | 49.1 | 50.9 | 1.9636 | 7.3 | 92.7 | 6.2 | 93.8 |
| 42.3 | 57.7 | 49.9 | 50.1 | 1.9962 | 0.8 | 99.2 | 0.7 | 99.3 |

FIG. 1 is a graph showing the relationship between the weight % of $CaCO_3$ as a raw material and the weight % of TTCP contained in the resulting biphasic SSCP powder portion.

When the weight % of the $CaCO_3$ is determined based on the sum of the weight of the $CaCO_3$ and the weight of the DCPA, the weight % of calcium contained in the resulting TTCP/α-TCP solid solution can be determined.

First, $CaCO_3$ and DCPs are mixed.

Examples of the methods of mixing the $CaCO_3$ and DCPs include putting the $CaCO_3$ and DCPs in a container, followed by a method of shaking the container, a method of rotating the container, and a method of installing a stirring blade in the container and rotating the stirring blade.

When the $CaCO_3$ and DCPs are mixed, both a dry blending method of mixing the both in a solid state and a wet blending method of charging a liquid and mixing the both in the liquid can be employed.

Since the frictional heat during the mixing of the $CaCO_3$ and DCPs is easily controlled and both can be mixed more uniformly, it is preferred to employ a wet blending method when the $CaCO_3$ and DCPs are mixed.

A liquid having a low solubility in the $CaCO_3$ and DCPs is preferably used as a liquid to be used in the wet blending method.

Examples of the liquid include an alcohol from the point of view of handleability.

The liquids can be used singly or in combination.

The mixing time of the $CaCO_3$ and DCPs, which changes depending on a mixed amount and the like, is generally in a range of 1 minute to 24 hours.

the filtration container has an airtight structure, and the inner part of the container is pressurized with a gas such as air and nitrogen.

Further, the filtration can also be performed by centrifugal force by preparing a rotatable filtering container, installing a bag-shaped filter cloth in the rotatable filtering container, and rotating the filtering container.

After performing the filtration, it is preferred to replace the liquid permeated the inner part of the mixture of $CaCO_3$ and DCPs with a volatile solvent such as alcohol.

The mixture can be dried in a short time by replacing the liquid with the volatile solvent.

Next, the mixture of $CaCO_3$ and DCPs is finely ground as necessary.

Examples of the equipment used in the step of grinding the mixture include a ball mill and a blender.

Since the ball mill, the blender, and the like are commercially available, these commercially available equipment can be arbitrarily selected and used.

Next, the mixture of $CaCO_3$ and DCPs is heated.

The mixture is housed in a container such as a crucible and heated using a heating means such as a heating furnace. The mixture may be heated in the presence of air or in the presence of inert gas, such as nitrogen and argon.

The heating temperature of the mixture is within a range of 1200 to 1600° C.

The temperature range is preferably in a range of 1300 to 1500° C., more preferably in a range of 1400 to 1600° C.

The heating time of the mixture is in a range of 1 to 24 hours.

The heating time is preferably in a range of 2 to 13 hours, more preferably in a range of 3 to 9 hours.

Further, the mixture is preferably heated to a temperature of more than 1200° C. in a range of 30 minutes to 2 hours from the start of heating.

After the completion of heating, the mixture is cooled.

Examples of the methods of cooling the mixture include a method of allowing the mixture to stand still under a condition of room temperature to slowly cool the same, a method of bringing the container housing the mixture into contact with a low-temperature medium to reduce the temperature, and a method of exposing the mixture to a low-temperature gas.

Usually, after the completion of heating, the mixture is air cooled for 5 minutes to 1 hour and then dried in a device such as a vacuum desiccator.

The TTCP/α-TCP solid solution comprising TTCP and α-TCP can be obtained by these steps.

Next, the resulting TTCP/α-TCP solid solution is ground.

Examples of the methods for grinding the TTCP/α-TCP solid solution include a method of using a commercially available grinding machine such as a ball mill and a blender as described above.

Further, the TTCP/α-TCP solid solution can also be put into a mortar and ground using a pestle or the like manually or mechanically.

The ground TTCP/α-TCP solid solution is sieved and separated into a powdered TTCP/α-TCP solid solution and an insufficiently ground TTCP/α-TCP solid solution.

The sieving of the ground TTCP/α-TCP solid solution can be performed by shaking the sieve with a shaking machine or the like.

The insufficiently ground TTCP/α-TCP solid solution is ground again using a grinding machine such as a ball mill and a blender.

A powdered TTCP/α-TCP solid solution having a desired average particle size can be obtained by repeating the grinding step and the sieve separation step.

Further, as a step of grinding the resulting TTCP/α-TCP solid solution, a wet grinding step may be employed, or the dry grinding step and the wet grinding step may be employed in combination, instead of the dry grinding step described above.

The wet grinding step can be performed, for example, by grinding the TTCP/α-TCP solid solution with a grinding machine such as a ball mill and a blender in the presence of a liquid such as a volatile solvent such as alcohol.

The ground TTCP/α-TCP solid solution and the liquid can be separated by the same operation as in the filtering step described above.

It is also possible to obtain the ground TTCP/α-TCP solid solution by a method of evaporating the liquid without performing a filtering step.

When the wet grinding step is performed, it is preferred to dry the powdered TTCP/α-TCP solid solution in order to prevent the liquid from remaining in the powdered TTCP/α-TCP solid solution finally obtained.

Examples of the methods of drying the powdered TTCP/α-TCP solid solution include a method of putting the solid solution in a general-purpose oven and heat-treating the same at a temperature equal to or more than the boiling point of the liquid.

The heating temperature of the powdered TTCP/α-TCP solid solution is preferably in a range of 70 to 100° C.

Further, the heating time of the powdered TTCP/α-TCP solid solution is preferably in a range of 1 to 72 hours, more preferably in a range of 12 to 36 hours.

The biphasic SSCP powder portion comprising the TTCP/α-TCP solid solution can be obtained by the steps described above.

The biphasic SSCP powder portion comprises TTCP and α-TCP, and the weight fraction of α-TCP in the biphasic SSCP powder portion is preferably in a range of 10 to 90%.

Further, the average particle size of the biphasic SSCP powder portion used in the present invention is preferably in a range of 1 to 100 μm, more preferably in a range of 5 to 30 μm.

When the average particle size is in a range of 1 to 100 μm, the biphasic SSCP powder portion and the biphasic SSCP liquid portion which are used in the present invention can be easily uniformly kneaded, and biphasic SSCP exhibiting stable physical properties will be obtained.

Further, examples of the shape of the biphasic SSCP powder portion include, but are not particularly limited to, at least one of an indefinite shape and a spherical shape.

Next, the difference between the biphasic SSCP powder portion used in the present invention and a TTCP/α-TCP mixture obtained by producing TTCP and α-TCP separately and mixing the both will be described.

In the case of the TTCP/α-TCP mixture, it is possible to separate TTCP and α-TCP by a physical means.

On the other hand, when the biphasic SSCP powder portion used in the present invention comprises a TTCP/α-TCP solid solution, it is practically impossible to separate TTCP and α-TCP from the biphasic SSCP powder portion by a physical means.

Figure 4:
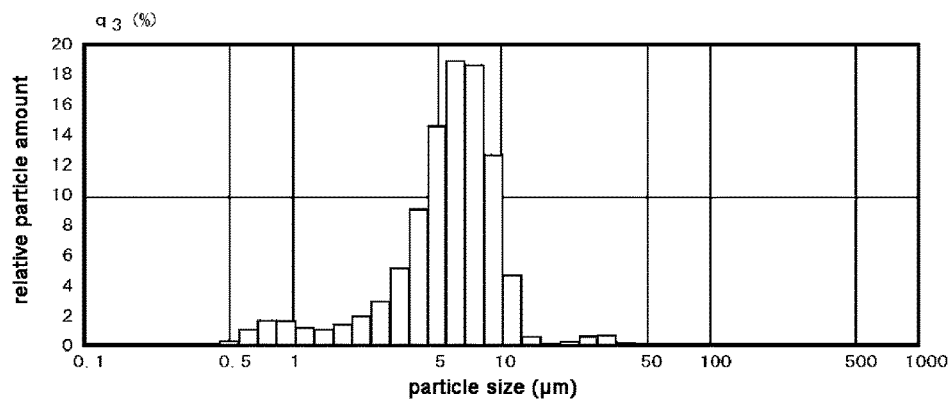
FIG. 4 is a graph showing the particle size distribution of the biphasic SSCP according to Reference Example 1.
Figure 5:
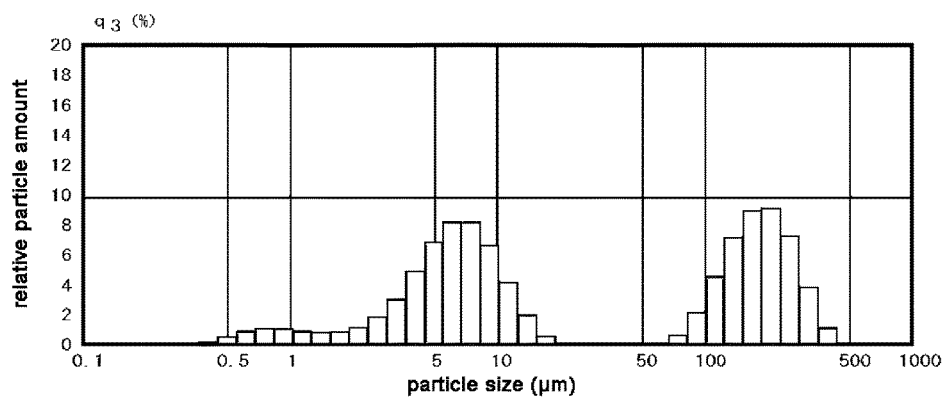
FIG. 5 is a graph showing the particle size distribution of a TTCP/$\alpha$-TCP mixture.

FIG. 4 is a graph showing the particle size distribution of the biphasic SSCP obtained by Reference Example 1 to be described below. Further, FIG. 5 is a graph showing the particle size distribution of a TTCP/α-TCP mixture.

A commercially available sample was used as the TTCP/α-TCP mixture. Further, a commercially available laser type particle size distribution analyzer or the like can be used for the measurement of particle size distribution.

When the biphasic SSCP powder portion used in the present invention is a TTCP/α-TCP solid solution, α-TCP and TTCP are uniformly produced as a solid solution in one step. Therefore, the particle size distribution of the biphasic SSCP powder portion is monomodal as shown in FIG. 4.

On the other hand, since the TTCP/α-TCP mixture is obtained by producing TTCP and α-TCP separately and mixing the both, the particle size distributions of TTCP and α-TCP are different. Therefore, when TTCP and α-TCP having different particle size distributions are mixed, the particle size distribution of the whole TTCP/α-TCP mixture will be bimodal.

Note that it is possible to bring the particle size distribution of the TTCP/α-TCP mixture having a bimodal particle size distribution at the beginning close to a monomodal distribution by grinding the TTCP/α-TCP mixture more finely.

However, in the case of the TTCP/α-TCP mixture, since the particles of TTCP and the particles of α-TCP are physically mixed, both can be separated utilizing the difference between the specific gravity of TTCP and that of α-TCP.

Specifically, since the specific gravity of TTCP is 3.06 g/cm$^3$ and the specific gravity of α-TCP is 2.86 g/cm$^3$, both can be separated by the difference of specific gravity using a liquid which has an intermediate specific gravity and dissolves neither TTCP nor α-TCP.

For example, 1,1,2,2-tetrabromoethane (specific gravity: 2.97 g/cm$^3$) can be used as the liquid described above.

The α-TCP having a lower specific gravity than that of the liquid moves to the upper layer in the liquid, and TTCP having a higher specific gravity moves to the lower layer.

On the other hand, since the biphasic SSCP powder portion is a uniform solid solution, it cannot be separated into TTCP and α-TCP even if it is dispersed in a liquid.

By this method, it can be easily determined whether a sample is the TTCP/α-TCP mixture or it is the TTCP/α-TCP solid solution.

The biphasic SSCP powder portion used in the present invention may be any of the TTCP/α-TCP mixture or the TTCP/α-TCP solid solution, but is preferably a solid solution comprising TTCP and α-TCP.

As shown in Table 1, the biphasic SSCP powder portion has a wide composition. The molar ratio of calcium to phosphorus thereof is preferably in a range of 1.52 to 1.97.

Next, the biphasic SSCP liquid portion used in the present invention will be described.

The biphasic SSCP liquid portion used in the present invention comprises a phosphoric acid aqueous solution containing a calcium component.

Further, the calcium component is at least one selected from the group consisting of $Ca(OH)_2$, $CaO$, and $CaCO_3$.

The calcium component is in a range of 1 to 99 weight % relative to the phosphoric acid aqueous solution, but in the biphasic SSCP liquid portion used in the present invention, the calcium component is preferably in an undersaturated state in the phosphoric acid aqueous solution.

It is preferred that the biphasic SSCP liquid portion is undersaturated with respect to the calcium phosphate compound.

Here, examples of the calcium phosphate compound include monocalcium phosphate monohydrate (MCPM, $Ca(H_2PO_4)H_2O$), monocalcium phosphate anhydrous (MCPA, $Ca(H_2PO_4)_2$), dicalcium phosphate dihydrate (DCPD, $CaHPO_4 2H_2O$), dicalcium phosphate anhydrous (DCPA, $CaHPO_4$), amorphous calcium phosphate (ACP, $Ca_3(PO_4)$), α-tricalcium phosphate (α-TCP, $α-Ca_3(PO_4)_2$), β-tricalcium phosphate (β-TCP, $β-Ca_3(PO_4)_2$), and tetracalcium phosphate (TTCP, $Ca_4(PO_4)_2$). These calcium phosphate compounds may be anhydrides or may contain crystal water.

The hydrogen ion concentration of the biphasic SSCP liquid portion is preferably in a range of 0.1 to 2.5.

Further, it is preferred that the calcium concentration of the biphasic SSCP liquid portion be in a range of $1.0 \times 10^{-3}$ mol/L to 1.1 mol/L, and it is more preferred that the phosphorus concentration of the aqueous solution be in a range of 0.5 mol/L to 8 mol/L.

An example of the methods for producing the biphasic SSCP liquid portion is as follows.

A $CaCO_3$ suspension in which particulate $CaCO_3$ is dispersed in water is produced. When phosphoric acid is added to the $CaCO_3$ suspension with stirring, the foaming by carbon dioxide will start. When the foaming is settled, a transparent biphasic SSCP liquid portion will be obtained as an aqueous solution.

The concentration of calcium and the concentration of phosphorus contained in the biphasic SSCP liquid portion can be controlled by changing the amount of $CaCO_3$ and the amount of phosphoric acid to be used, respectively.

Next, a kneaded material obtained by kneading the biphasic SSCP powder portion and the biphasic SSCP liquid portion will be described.

When the biphasic SSCP powder portion and the biphasic SSCP liquid portion are kneaded, a paste-like or clay-like kneaded material can be obtained.

The paste-like or clay-like kneaded material can be formed into any desired shape by filling or overfilling the defects of bone, teeth, and the like with the kneaded material using a device such as a spatula.

Further, the kneaded material can also be injected into the desired place utilizing a syringe or the like.

In the present invention, the work time of the kneaded material can be controlled in a range of 10 seconds to 600 seconds.

Here, the work time means a time in which a kneaded material of the biphasic SSCP powder portion and the biphasic SSCP liquid portion can be shaped, or a time in which the kneaded material can be formed into an arbitrary shape at will without adversely affecting the setting process of the biphasic SSCP or the strength of the set material of the biphasic SSCP.

In order to control the work time, the hydrogen ion concentration (pH) of the biphasic SSCP liquid portion and the calcium concentration and phosphorus concentration of the biphasic SSCP liquid portion may be changed. Thus, since various compositions of the biphasic SSCP liquid portion can be utilized, the work time until the biphasic SSCP sets can be freely controlled in a range of 10 seconds to 600 seconds.

When the biphasic SSCP liquid portion to be used is diluted with water, the calcium concentration and the phosphorus concentration will be reduced to slow the reaction between the phosphorus component and the calcium component, thus increasing the work time.

Conversely, the higher the calcium concentration and the phosphorus concentration of the biphasic SSCP liquid portion to be used, the shorter the work time.

When the biphasic SSCP powder portion and the biphasic SSCP liquid portion are kneaded, the kneaded material will set at room temperature through the work time described above.

Here, the room temperature means a range of 25° C. plus/minus 15° C.

Further, the setting time means the time required for setting the kneaded material of the biphasic SSCP powder portion and the biphasic SSCP liquid portion so that the kneading may be completed.

Whether the kneaded material has set or not can be determined by the fact that the kneaded material does not deform even when it is pushed with a device such as a spatula.

Further, when the surface of the kneaded material is pushed using a needle device such as a Vicat needle or a Gilmore needle, the time point when the indentation on the surface of the kneaded material is not changed can also be determined as the time point when the kneaded material has set.

In the present invention, the work time of the kneaded material of the biphasic SSCP powder portion and the biphasic SSCP liquid portion is the sum of the allowed time for injection and the allowed time for shape forming shown by the kneaded material.

The biphasic SSCP shows sufficient work time and then sets relatively rapidly.

The setting time comes after the work time. Therefore, when the setting time of the kneaded material is intended to be reduced, the work time may be reduced as described above, and when the setting time of the kneaded material is intended to be increased, the work time may be increased.

In the case of the present invention, since the kneaded material can be used to be easily formed into a certain shape, the biphasic SSCP before the kneaded material sets has shape formability.

The setting of the kneaded material advances with the lapse of time. Since the biphasic SSCP after the kneaded material has set has a strength that can sufficiently respond to surgical operation such as suture, it has shape maintainability.

The biphasic SSCP after setting is suitable for the application of a hard tissue regeneration material.

Next, in the present invention, a sodium citrate compound can be added to at least one of the biphasic SSCP powder portion and the biphasic SSCP liquid portion to be used.

Here, the sodium citrate compound means at least one selected from the group consisting of monosodium citrate, disodium citrate, and trisodium citrate.

The surface of the biphasic SSCP powder portion is covered with a sodium citrate compound by kneading the biphasic SSCP powder portion, the biphasic SSCP liquid portion, and the sodium citrate compound.

The biphasic SSCP powder portion comes to have charge by the covering, and the particles of the biphasic SSCP powder portion electrostatically repel one another. Therefore, the kneading operation of the biphasic SSCP powder portion and the biphasic SSCP liquid portion is smooth and facilitated, and the kneading is achieved using a small amount of the biphasic SSCP liquid portion, thus improving operability and physical properties.

The sodium citrate compound added to the biphasic SSCP powder portion has a character that since the particles of the powder portion electrostatically repel one another in the kneading with the biphasic SSCP liquid portion, the kneading is achieved using a small amount of liquid.

Further, when the biphasic SSCP is used for the application of hard tissue regeneration materials such as a bone graft material and a dental material, the sodium citrate compound contained in the biphasic SSCP is specifically decomposed by an enzyme and nonspecifically decomposed by hydrolysis in the body and detoxicated.

Therefore, the sodium citrate compound may hardly make harmful effect to a body even if the biphasic SSCP contains the sodium citrate compound.

Further, the sodium citrate compound is effective in retarding the conversion rate of the biphasic SSCP powder portion and the biphasic SSCP liquid portion to HA. Therefore, when the biphasic SSCP powder portion and the biphasic SSCP liquid portion are kneaded, the time to the setting can be retarded by using the sodium citrate compound.

At least one of the biphasic SSCP powder portion and the biphasic SSCP liquid portion preferably contains the sodium citrate compound in a range of 0.5 to 5 mol/L.

This range is more preferably in a range of 1 to 4 mol/L.

Further, the biphasic SSCP liquid portion used in the present invention is an aqueous solution containing phosphoric acid, and the concentration of phosphoric acid in the biphasic SSCP liquid portion is preferably in a range of 3 to 45 weight %.

If the concentration of phosphoric acid in the biphasic SSCP liquid portion is less than 3 weight %, the resulting hard tissue regeneration material tends to require longer time for setting, and if the concentration of phosphoric acid in the biphasic SSCP liquid portion is more than 45 weights, the kneading of the biphasic SSCP liquid portion and the biphasic SSCP powder portion tends to be difficult.

With respect to the mixing ratio of the biphasic SSCP powder portion to the biphasic SSCP liquid portion, the setting time of a kneaded material of the biphasic SSCP powder portion and the biphasic SSCP liquid portion and the properties before setting of the kneaded material can be controlled by adjusting the weight of the biphasic SSCP liquid portion in a range of 0.1 to 10 times based on the unit weight of the biphasic SSCP powder portion.

The hard tissue regeneration material using the biphasic SSCP powder portion obtained by the production method of the present invention has a character that the work time and setting time can be adjusted. Therefore, the setting time in conformity with clinical requirements can be set.

Further, since the hard tissue regeneration material before setting has a paste-like or clay-like shape, it can be reliably formed into the shape of a bone defect.

Further, the resulting hard tissue regeneration material has a character that since, in the body, the absorption by osteoclast advances and the replacement to new bone advances by the action of osteoblast or the like, the hard tissue regeneration material is replaced to inherent bone in a short period of time while keeping a state where the hard tissue regeneration material is bonded to the surrounding existing bone.

Further, a shape forming agent can be added to at least one of the biphasic SSCP powder portion and the biphasic SSCP liquid portion.

Examples of the shape forming agent include carboxymethyl cellulose, hydroxymethyl cellulose, hydroxyethyl cellulose, hydroxypropyl cellulose, polyvinyl pyrrolidone, a carboxyvinyl polymer, sodium alginate, gellant gum, xanthan gum, sodium polyacrylate, pectin, tragacanth gum, gum arabic, guar gum, karaya gum, locust bean gum, tamarind gum, psyllium seed gum, polyvinyl alcohol, sodium chondroitin sulfate, and a methoxyethylene-maleic anhydride copolymer.

Preferred examples of the shape forming agent include carboxymethyl cellulose, hydroxymethyl cellulose, hydroxyethyl cellulose, hydroxypropyl cellulose, polyvinyl pyrrolidone, a carboxyvinyl polymer, sodium alginate, gellant gum, and xanthan gum.

The shape forming agents can be used singly or in combination.

The shape forming agent is preferably added in a range of 0.01 to 3.0 weights, more preferably 0.1 to 3.0 weight %, further preferably 0.5 to 1.0 weight %, based on the total weight of the biphasic SSCP powder portion and the biphasic SSCP liquid portion.

One or two or more of a coloring agent, a preservative, a germicide, an osteoinductive factor, a blood product, a porogen, an antibiotic agent, a radiopaque agent, a strength reinforcing fiber material, and the like can also be added as necessary to at least one of the biphasic SSCP powder portion and the biphasic SSCP liquid portion.

Examples of the coloring agent include an inorganic pigment.

Examples of the preservative include para-hydroxybenzoate such as sodium benzoate, methylparaben, ethylparaben, and butylparaben, and ethylenediaminetetraacetate.

Examples of the germicide include cetylpyridinium chloride, benzethonium chloride, benzalkonium chloride, and chlorhexidine.

Examples of the osteoinductive factor include dexamethasone, ascorbic acid-2-phosphate, 3-glycerophosphate, and bone morphogenetic protein.

Examples of the blood product include erythropoietin, a parenteral iron preparation, hemin, hematoporphyrin, and derivatives thereof.

Examples of the porogen include ethanol, glycerin, and ethylene glycol.

Examples of the antibiotic agent include mitomycin, adriamycin, doxorubicin, actinomycin, daunorubicin, idarubicin, pirarubicin, aclarubicin, epirubicin, peplomycin, and zinostatin stimalamer.

Examples of the radiopaque agent include ZnO, zinc-containing aluminoborate glass, and alkaline earth metal aluminosilicate glass.

Examples of the strength reinforcing fiber material include silica glass fiber, alumina fiber, and carbon fiber.

According to the present invention, the biphasic SSCP, in which the work time that is required for shape-forming, from the start of kneading the biphasic SSCP powder portion and the biphasic SSCP liquid portion to the setting of the resulting kneaded material, is in a range of 10 seconds to 600 seconds at a temperature in a range of 10 to 40° C., can be used for the application of a hard tissue regeneration material and the like.

Specifically, it is also possible to provide a hard tissue regeneration material kit comprising the biphasic SSCP powder portion and the biphasic SSCP liquid portion.

The hard tissue regeneration material kit comprises the biphasic SSCP powder portion and the biphasic SSCP liquid portion, and it is preferred that the hard tissue regeneration material kit comprise a sodium citrate compound in addition to the biphasic SSCP powder portion and the biphasic SSCP liquid portion.

Further, it is more preferred that the hydrogen ion concentration of the biphasic SSCP liquid portion be in a pH range of 1.0 to 6.5.

The hard tissue regeneration material kit preferably comprises a container for putting the biphasic SSCP powder portion therein, a container for putting the biphasic SSCP liquid portion therein, a plate made of an inorganic material such as glass, a synthetic resin material such as polyethylene, polypropylene, and polyethylene terephthalate, or a metallic material for kneading the biphasic SSCP powder portion and the biphasic SSCP liquid portion, and a stirring rod made of at least one of the inorganic material, the synthetic resin material, and the metallic material.

The sodium citrate compound may be previously added to at least one of the biphasic SSCP powder portion and the biphasic SSCP liquid portion.

Further, the sodium citrate compound may be put into a container in order to be mixed with at least one of the biphasic SSCP powder portion and the biphasic SSCP liquid portion and provided as a solid such as powder or a liquid such as an aqueous solution.

Next, application examples to dental materials using biphasic SSCP prepared by combining the biphasic SSCP powder portion and the biphasic SSCP liquid portion will be described.

[Composition for Relieving Dentin Hypersensitivity to Teeth]

The composition comprising the biphasic SSCP powder portion and the biphasic SSCP liquid portion can be used as a composition for relieving dentin hypersensitivity to teeth.

The composition prepared by kneading the biphasic SSCP powder portion and the biphasic SSCP liquid portion can be used for the application of applying the composition to the tooth surface in which the symptom of dentin hypersensitivity has occurred.

The composition for relieving dentin hypersensitivity to teeth can be set on the tooth surface to form a set material to block fine pores communicating with the nerves exposed to the tooth surface.

Since the same component as a biomaterial is used in the set material, the set material does not cause an allergic reaction to a human. This point is the same also in the case of the following application examples.

Further, since the set material does not dissolve in human body fluid, it can be prevented from outflowing from the tooth surface.

Further, since a protective layer formed on the tooth surface by the set material is integrated with the tooth surface, the symptom of dentin hypersensitivity to teeth can be relieved over a long period of time without exfoliation, wear, and detachment by the friction of daily chewing motion, toothbrushing, and the like.

Further, the symptom of dentin hypersensitivity can be relieved by applying the kneaded composition for several minutes to the affected tooth surface in which the symptom of dentin hypersensitivity has occurred, followed by water washing.

[Composition for Filling Dental Caries Portion]

A composition comprising the biphasic SSCP powder portion and the biphasic SSCP liquid portion can be used as a composition for filling a cavity portion from which a dental caries portion has been removed. Further, the composition can be used also as a composition for suppressing the progress of dental caries.

When the enamel layer on the tooth surface is eroded by the activity of a germ leading to dental caries such as *Streptococcus mutans*, the crystal structure of HA in the enamel layer is partially broken, which prevents light from travelling in a straight line, causing a phenomenon called white spot in which the eroded portion looks whitish.

The composition prepared by kneading the biphasic SSCP powder portion and the biphasic SSCP liquid portion can be used for the application of filling or coating the tooth surface in the early dental caries with the composition.

The composition for preventing the progress of dental caries can be set on the tooth surface to form a HA crystal to regenerate the eroded enamel layer.

By applying the composition for preventing the progress of dental caries to the tooth surface, the progress of dental caries can be suppressed as well as the enamel layer of HA in the eroded tooth surface is regenerated, thereby capable of always maintaining white beautiful teeth.

Further, it is also possible to apply the kneaded composition for several minutes to the early dental caries portion of the white spot followed by water washing.

[Composition for Accelerating Remineralization to Tooth Enamel]

The composition comprising the biphasic SSCP powder portion and the biphasic SSCP liquid portion can be used for the application of accelerating the remineralization of the tooth surface.

The application example of the composition for accelerating remineralization to tooth enamel will be described using gum as an example.

The gum in which the biphasic SSCP powder portion is dispersed can be obtained, for example, by kneading a base resin of the gum such as polyvinyl acetate with the biphasic SSCP powder portion and extruding the kneaded material into a plate shape.

Further, the gum containing the biphasic SSCP liquid portion can be obtained, for example, by kneading a base resin of the gum such as polyvinyl acetate with the biphasic SSCP liquid portion and extruding the kneaded material into a plate shape.

By chewing in a mouth both the gum in which the biphasic SSCP powder portion is dispersed and the gum containing the biphasic SSCP liquid portion at the same time, the biphasic SSCP powder portion reacts with the biphasic SSCP liquid portion to form a set material.

Since the tooth surface is coated with the set material by chewing the gum for accelerating remineralization in a mouth, the remineralization of the tooth surface is accelerated, and the gum for accelerating remineralization can be used for the applications of relieving the symptom of dentin hypersensitivity to teeth, suppressing the progress of dental caries, and regenerating the enamel layer on the tooth surface.

Next, the application example of the composition for accelerating remineralization to tooth enamel will be described using a tooth paste as an example.

A tooth paste in which the biphasic SSCP powder portion is dispersed can be produced, for example, by the following steps.

A tooth paste is kneaded with the biphasic SSCP powder portion to produce a tooth paste containing the biphasic SSCP powder portion.

Similarly, a tooth paste is kneaded with the biphasic SSCP liquid portion to produce a tooth paste containing the biphasic SSCP liquid portion.

A tube for tooth paste has two inner parts separated from each other. One of the inner parts is filled with the tooth paste containing the biphasic SSCP powder portion, and the other is filled with the tooth paste containing the biphasic SSCP liquid portion. When pressure is applied to the tube for tooth paste, each of the tooth paste containing the biphasic SSCP powder portion and the tooth paste containing the biphasic SSCP liquid portion is extruded from the tube for tooth paste and is brought into contact with each other to be mixed at the outlet of the tube for tooth paste.

If the nozzle of the outlet part of the tube for tooth paste has a helical structure, each of the tooth paste containing the biphasic SSCP powder portion and the tooth paste containing the biphasic SSCP liquid portion will be mixed more uniformly.

The tooth paste containing the biphasic SSCP powder portion and the tooth paste containing the biphasic SSCP liquid portion extruded from the tube for tooth paste are kneaded on the teeth of a user with a toothbrush.

The biphasic SSCP powder portion reacts with the biphasic SSCP liquid portion to form a set material, which sets on the tooth surface.

Since the tooth surface is coated with the set material, the remineralization of the tooth surface is accelerated, and the tooth paste for accelerating remineralization can be used for the applications of relieving the symptom of dentin hypersensitivity, suppressing the progress of dental caries, and regenerating the enamel layer on the tooth surface.

Next, the application example of the composition for accelerating remineralization to tooth enamel will be described using mouthwash as an example.

A mouth is washed with a dispersion prepared by dispersing a kneaded material of the biphasic SSCP powder portion and the biphasic SSCP liquid portion in a mouthwash liquid.

The biphasic SSCP powder portion reacts with the biphasic SSCP liquid portion to form a set material, which sets on the tooth surface.

Since the set material adheres to the tooth surface, the remineralization of the tooth surface is accelerated, and the mouthwash for accelerating remineralization can be used for the applications of relieving the symptom of dentin hypersensitivity, suppressing the progress of dental caries, and regenerating the enamel layer on the tooth surface.

[Dental Pulp Capping Composition for Covering an Exposed Portion of Dental Pulp]

There will be no problem if only a portion in which dental caries has progressed can be cut off from a tooth of a patient with progressed dental caries, but the cut portion may reach the dental pulp in the inner part of the tooth in the process of operation for cutting off the portion in which dental caries has progressed.

When dental pulp is exposed by the operation, pulpectomy needs to be performed in order to reduce the pain of the tooth of the patient.

However, since dental pulp plays a role of growing and maturing teeth, if pulpectomy is performed to low-aged patients, a problem will occur in that teeth of the patient do not sufficiently grow.

The biphasic SSCP prepared by kneading the biphasic SSCP powder portion and the biphasic SSCP liquid portion can be set in an exposed portion of dental pulp to cover the exposed portion of dental pulp. Since the covering eliminates the necessity of performing pulpectomy, the problem of tooth growth stop caused by the absence of dental pulp can be solved.

Further, when a conventional dental pulp capping material is used, there has been a problem in that the dental pulp capping material gives large stimulation to the teeth of a patient when it is brought into contact with the dental pulp of the patient.

On the other hand, since the biphasic SSCP has properties of forming HA which has almost the same composition as that of the teeth of a patient, the patient hardly feels pain even if it is brought into contact with the dental pulp. Therefore, the pain of the teeth of the patient can be reduced.

[Covering Composition for Covering Tooth Perforation]

When the dental root of a patient is perforated, the perforated portion will reach the periodontal tissues. For the purpose of preventing the infection to the exposed part of the periodontal tissues located in the surroundings of the perforation, the perforation can be covered with the biphasic SSCP prepared by kneading the biphasic SSCP powder portion and the biphasic SSCP liquid portion.

Since the dentin of the perforation mainly contains HA as the main component of the mineral portion and a set material of the biphasic SSCP also substantially comprises HA, the infection can be prevented by covering the perforation with the biphasic SSCP.

Further, the biphasic SSCP acts as a good covering composition since it has good bioaffinity and biocompatibility also with the periodontal tissues.

[Dental Root Canal Filling Composition]

After removing the dentin and nerve in the inner part of a tooth in which a germ has infected by a symptom such as dental caries, a cavity called a root canal is produced.

The dental root canal filling composition can be used for the application of filling the inner part of the cavity.

A paste-like composition obtained by kneading the biphasic SSCP powder portion and the biphasic SSCP liquid portion is loaded into a syringe and extruded into the inner part of the cavity with a plunger. Thus, the composition can be filled into the cavity in a shape corresponding to the shape of the cavity.

The dental root canal filling composition sets in the inner part of the root canal and forms a set material. The main component of the set material is HA, and the dentin forming a root canal wall also comprises HA as the main constituent. Therefore, the set material and the root canal can be bonded to each other to obtain good compatibility and sealing.

Further, even if the composition overflows into the periodontal tissues from the apical foramen which is the outlet of the root canal, the set material has bone replaceability and thus has good bioaffinity and biocompatibility with the periodontal tissues. Therefore, the composition acts as a good root canal filling composition.

Hereinafter, the present invention will be described in detail with reference to Examples. Note that the present invention is not limited at all by the following Examples.

Reference Example 1

Method for Producing TTCP/α-TCP Solid Solution $CaCO_3$ and DCPA are put in a general-purpose oven and heated for 2 to 3 hours at a temperature of 105° C. to dry the $CaCO_3$ and DCPA.

Next, the dried $CaCO_3$ powder and DCPA powder are allowed to stand still in a vacuum desiccator and cooled.

The mixing ratio of the TTCP/α-TCP to be obtained can be adjusted by adjusting the mixing weight ratio of $CaCO_3$ to DCPA as shown in Table 1 described above. In the case of Example 1, a case of using 349 g of $CaCO_3$ and 651 g of DCPA will be described.

In this case, the weight % of the $CaCO_3$ based on the sum of the weight of the $CaCO_3$ and the weight of the DCPA is 34.9 weight %.

The $CaCO_3$ and DCPA are put in a 4000 mL graduated beaker (252 mm in height and 161 mm in diameter).

Next, 3000 mL of distilled water is poured into the graduated beaker, and then a dispersion of the mixture is stirred for 6 to 7 hours at rate of about 300 rpm using an overhead stirrer equipped with a large anchor type stirring rod having a diameter of 150 mm.

After the completion of mixing, the dispersion of the mixture is filtered using a filter comprising a side-arm Erlenmeyer flask equipped with a funnel in the upper part thereof with Whatman filter paper No. 1 being placed in the funnel and decompressing the inner part of the side-arm Erlenmeyer flask.

The resulting mixture is rinsed with 200 mL of ethanol, and then the mixture is allowed to stand still in a vacuum desiccator and dried.

The dried mixture is finely ground using a blender.

Next, six to nine alumina crucibles (conical crucibles each having a capacity of 250 mL) are prepared, and 160 g of the resulting ground powder is put in each crucible before the crucibles are placed in a heating furnace.

The temperature in the heating furnace is set so as to be slowly increased from room temperature and reach 1500° C. in 60 minutes, and the temperature is maintained for 6 hours at 1500° C.

After the lapse of 6 hours, the crucible is removed from the heating furnace and arranged on a brick. The crucible is arranged on a brick and air cooled for about 15 minutes to quickly reduce the temperature, and the crucible is then allowed to stand still in a vacuum desiccator and cooled.

The contents of two crucibles among the above crucibles are manually triturated using a mortar and a pestle.

A coarse powder and a small block among the contents of the crucibles are put in a blender and ground for 60 seconds.

The contents of the blender are removed and transferred to a stainless steel sieve with 8 inches in diameter having an opening width of 28 μm, and the sieve is put in a sieve shaking machine. The contents in the sieve shaking machine are sieved in about 10 minutes.

The powder remaining on the sieve is again put in the blender, ground for 60 seconds, and then put in the sieve, which is shaken again with the sieve shaking machine for 10 minutes.

This step is further repeated twice.

After repeating the grinding step using a blender and the sieving step a total of three times, the resulting powder is mixed with the manually ground powder.

A biphasic SSCP powder portion comprising a TTCP/α-TCP solid solution is obtained by the steps described above.

The resulting biphasic SSCP powder portion has a Ca/P (molar ratio) of 1.73 and contains TTCP and α-TCP in an amount of 50 weight %, respectively.

Figure 3:
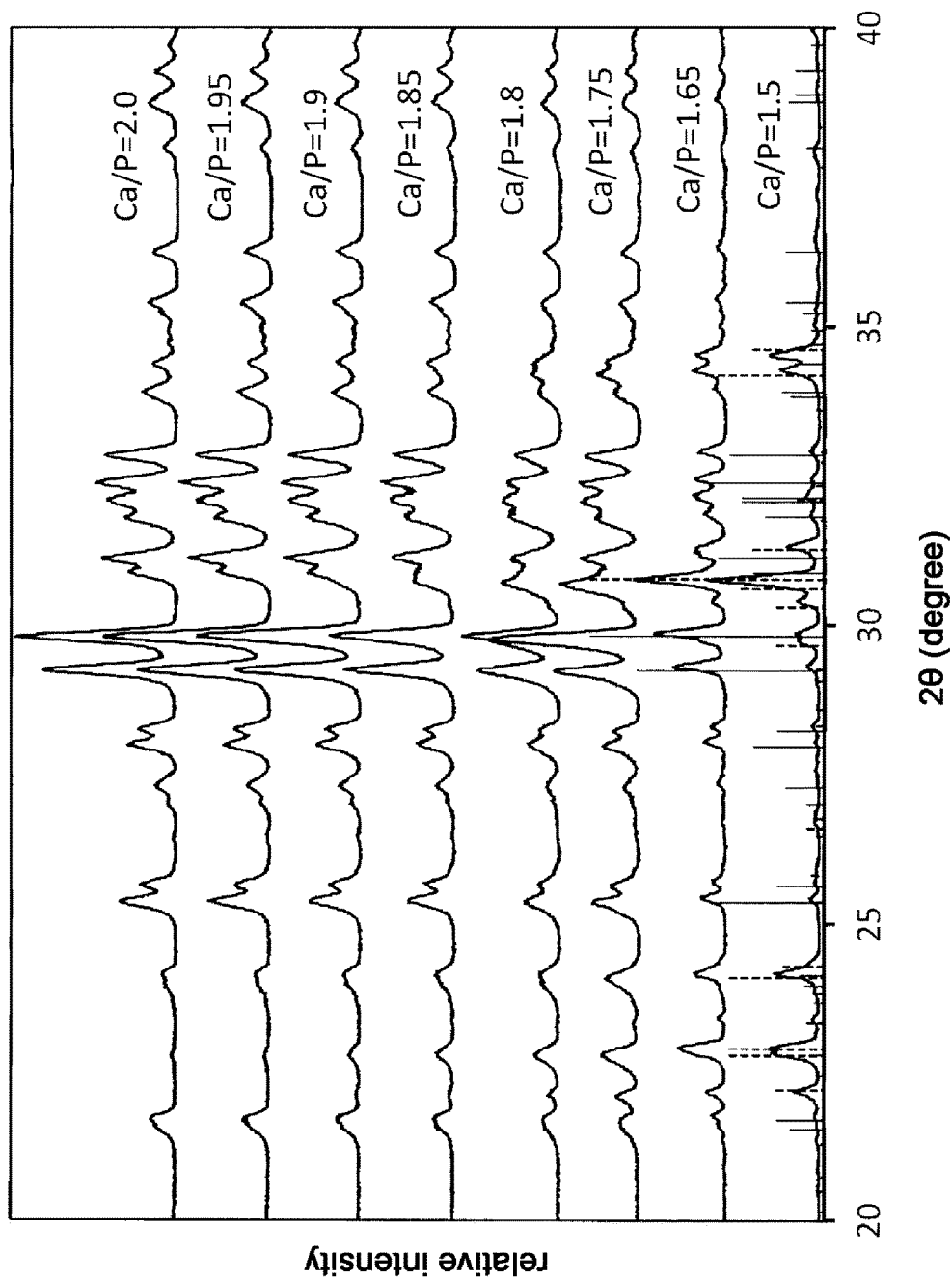
FIG. 3 shows the results of measurement of the X-ray diffraction of the resulting biphasic SSCP powder portion.

FIG. 3 shows the results of measurement of X-ray diffraction of the resulting biphasic SSCP powder portion. FIG. 3 shows the results of measurement of X-ray diffraction in the case of changing the Ca/P molar ratio in the biphasic SSCP powder portion obtained by completely the same operation as in the case of Example 1. The biphasic SSCP powder portion having a Ca/P molar ratio of 1.50 comprises α-TCP free particles. Further, the biphasic SSCP powder portion having a Ca/P molar ratio of 2.00 comprises TTCP free particles.

Reference Example 2

In the case of Reference Example 1, the resulting TTCP/α-TCP solid solution was ground by a dry grinding step to obtain a uniform powder.

On the other hand, Reference Example 2 is different from Reference Example 1 in that the TTCP/α-TCP solid solution was ground by a wet grinding step to obtain a uniform powder.

By the same operation as in the case of Reference Example 1, a coarse powder and a small block among the contents of the crucibles are put in a blender (manufactured by Waring Corp., a heavy-duty blender for laboratories, model number: 38BL52 (LBC10)) and ground for 20 seconds.

The contents of the blender are removed, transferred to a stainless steel sieve with 8 inches in diameter having an opening width of 420 μm, and manually sieved.

The grinding step using the blender and the sieving step are repeated until a sufficient amount of powder is obtained.

Next, 100 g of the powder passed through the sieve is put in an agate jar having a capacity of 350 mL in which 240 agate balls each having a diameter of 10 mm are contained.

Ethanol (90%) in an amount of 120 g is poured into the agate jar.

The agate jar is attached to a planetary ball mill, which is operated for 24 hours at 200 rpm.

After operating the planetary ball mill for 24 hours, the agate jar is opened and the ethanol therein is evaporated.

Next, the ground powder is recovered, put in a convection oven, and maintained at 70° C. for 24 hours for drying.

The biphasic SSCP powder portion comprising a TTCP/α-TCP solid solution is obtained by the steps described above.

Example 1

A biphasic SSCP liquid portion was prepared by adding 3.3 g of distilled water and CaO (available from Wako Pure Chemical Industries, Ltd., hereinafter the same) to 10 g of a phosphoric acid aqueous solution having a hydrogen ion concentration of pH 2.1 so that, in the biphasic SSCP liquid portion, the concentration of phosphorus was 2.96 mol/L and the concentration of calcium was 1.09 mol/L.

Further, trisodium citrate was added to the biphasic SSCP liquid portion in such a proportion that 1 mol of trisodium citrate and the biphasic SSCP liquid portion were combined into a total volume of 1 L.

Next, a biphasic SSCP powder portion having a molar ratio of calcium to phosphorus (Ca/P) of 1.81 obtained by the same production method as in Reference Example 1 was weighed in an amount of 3.0 g and kneaded with 1.0 g of the biphasic SSCP liquid portion using a spatula.

Note that, in the present invention, the powder-liquid ratio means the weight ratio of powder to liquid in which the weight of a liquid agent is taken as the denominator while the weight of powder is taken as the numerator.

The resulting kneaded material was shapeable for 10 seconds to 220 seconds after the start of kneading, and the work time of the resulting kneaded material was between 10 seconds and 220 seconds based on the time point of the start of kneading.

The mixture became not deformable 4.2 minutes (a range of plus/minus 30 seconds) after the start of kneading even when the kneaded material was pushed with a spatula.

Example 2

Eighty-five weight % phosphoric acid aqueous solution was diluted with distilled water to prepare 43 weight % phosphoric acid aqueous solution.

A biphasic SSCP liquid portion was prepared by dissolving 0.014 g of CaO in the 43 weights phosphoric acid aqueous solution in such a proportion that they were mixed to form a total volume of 1 ml.

Further, trisodium citrate was added to the biphasic SSCP liquid portion in such a proportion that 2 mol of trisodium citrate and the biphasic SSCP liquid portion were combined into a total volume of 1 L.

Next, a biphasic SSCP powder portion having a molar ratio of calcium to phosphorus (Ca/P) of 1.81 obtained by the same production method as in Reference Example 1 was weighed in an amount of 3.0 g and kneaded with 1.0 g of the biphasic SSCP liquid portion using a spatula.

The resulting kneaded material was shapeable for 10 seconds to 270 seconds after the start of kneading, and the work time of the resulting kneaded material was between 10 seconds and 280 seconds based on the time point of the start of kneading.

The kneadability was slightly poor because the kneaded material had a slightly low water content, but the kneaded material showed no depression in 5 minutes after the start of kneading even if it was pushed with a spatula. The mixture was not deformable in 5 minutes 30 seconds after the start of kneading even if it was pushed with a spatula.

Example 3

A biphasic SSCP liquid portion was obtained by dissolving 0.014 g of CaO in 85 weight % phosphoric acid aqueous solution and distilled water in such a proportion that they were mixed to form a total volume of 1 ml. In the biphasic SSCP liquid portion, the concentration of phosphorus was 7.38 mol/L, and the concentration of calcium was 0.25 mol/L.

Further, trisodium citrate was added to the biphasic SSCP liquid portion in such a proportion that 2.5 mol of trisodium citrate and the biphasic SSCP liquid portion were combined into a total volume of 1 L.

Next, a biphasic SSCP powder portion having a molar ratio of calcium to phosphorus (Ca/P) of 1.81 obtained by the same production method as in Reference Example 1 was weighed in an amount of 3.0 g and kneaded with 1.0 g of the biphasic SSCP liquid portion using a spatula.

The resulting kneaded material was shapeable for 10 seconds to 300 seconds after the start of kneading, and the work time of the resulting kneaded material was between 10 seconds and 320 seconds based on the time point of the start of kneading.

The mixture became not deformable 5.8 minutes (a range of plus/minus 12 seconds) after the start of kneading even when the kneaded material was pushed with a spatula.

Example 4

A biphasic SSCP liquid portion was obtained by dissolving 0.0504 g of CaO in 85 weights phosphoric acid aqueous solution and distilled water in such a proportion that they were mixed to form a total volume of 1 ml. In the biphasic SSCP liquid portion, the concentration of phosphorus was 3.69 mol/L, and the concentration of calcium was 0.90 mol/L.

Further, trisodium citrate was added to the biphasic SSCP liquid portion in such a proportion that 2 mol of trisodium citrate and the biphasic SSCP liquid portion were combined into a total volume of 1 L.

Next, a biphasic SSCP powder portion having a molar ratio of calcium to phosphorus (Ca/P) of 1.81 obtained by the same production method as in Reference Example 1 was weighed in an amount of 3.0 g and kneaded with 1.0 g of the biphasic SSCP liquid portion using a spatula.

The kneaded material was very soft liquid, and after the start of kneading, it became injectable in 10 seconds and shapeable in 2 minutes. The work time of the resulting kneaded material was between 120 seconds and 340 seconds.

The kneaded material showed no depression in 6 minutes after the start of kneading even if it was pushed with a spatula. The mixture was not deformable in 6 minutes and 30 seconds after the start of kneading even if it was pushed with a spatula.

Example 5

A biphasic SSCP liquid portion was obtained by dissolving CaO in 85 weight % phosphoric acid aqueous solution and distilled water in such a proportion that they were mixed to form a total volume of 1 ml. In the biphasic SSCP liquid portion, the concentration of phosphorus was 1.97 mol/L, and the concentration of calcium was 0.726 mol/L.

Further, trisodium citrate was added to the biphasic SSCP liquid portion in such a proportion that 1 mol of trisodium citrate and the biphasic SSCP liquid portion were combined into a total volume of 1 L.

Next, a biphasic SSCP powder portion having a molar ratio of calcium to phosphorus (Ca/P) of 1.81 obtained by the same production method as in Reference Example 1 was weighed in an amount of 3.0 g and kneaded with 1.0 g of the biphasic SSCP liquid portion using a spatula.

The resulting kneaded material was shapeable for 10 seconds to 180 seconds after the start of kneading, and the work time of the resulting kneaded material was between 10 seconds and 180 seconds based on the time point of the start of kneading.

The mixture was not deformable in 3.5 minutes (within a range of plus/minus 24 seconds) after the start of kneading even if it was pushed with a spatula.

[Measurement of DTS]

The measurement of diametral tensile strength (DTS) was made using Instron tester 5500 model (manufactured by United Calibration Corporation, Canada) according to ADA ("American Dental Association") specification No. 9 and ADA specification No. 27 of ISO-test procedure 4049 (1988). The diameter and the height of a test piece were first measured with a micrometer.

The test piece was sandwiched between iron plates each having a wet paper layer and crushed by applying pressure at a rate of 10 mm/min. The average value of the results of measurement of five test pieces was 4.7 MPa (within a range of plus/minus 0.4 Mpa).

Example 6

A biphasic SSCP liquid portion was obtained by dissolving CaO in 85 weight % phosphoric acid aqueous solution and distilled water in such a proportion that they were mixed to form a total volume of 1 ml. In the biphasic SSCP liquid portion, the concentration of phosphorus was 1.47 mol/L, and the concentration of calcium was 0.448 mol/L.

Further, trisodium citrate was added to the biphasic SSCP liquid portion in such a proportion that 1 mol of trisodium citrate and the biphasic SSCP liquid portion were combined into a total volume of 1 L.

Next, a biphasic SSCP powder portion having a molar ratio of calcium to phosphorus (Ca/P) of 1.81 obtained by the same production method as in Reference Example 1 was weighed in an amount of 3.0 g and kneaded with 1.0 g of the biphasic SSCP liquid portion using a spatula.

The resulting kneaded material was shapeable for 10 seconds to 270 seconds after the start of kneading, and the work time of the resulting kneaded material was between 10 seconds and 280 seconds based on the time point of the start of kneading.

The mixture was not deformable in 5.3 minutes (within a range of plus/minus 12 seconds) after the start of kneading even if it was pushed with a spatula. Further, when DST was measured in the same manner as in the case of Example 5, the measured value was 5.3 MPa (within a range of plus/minus 0.3 MPa).

Example 7

A biphasic SSCP liquid portion was obtained by dissolving CaO in 85 weight % phosphoric acid aqueous solution and distilled water in such a proportion that they were mixed to form a total volume of 1 ml. In the biphasic SSCP liquid portion, the concentration of phosphorus was 1.10 mol/L, and the concentration of calcium was 0.336 mol/L.

Further, trisodium citrate was added to the biphasic SSCP liquid portion in such a proportion that 1 mol of trisodium citrate and the biphasic SSCP liquid portion were combined into a total volume of 1 L.

Next, a biphasic SSCP powder portion having a molar ratio of calcium to phosphorus (Ca/P) of 1.81 obtained by the same production method as in Reference Example 1 was weighed in an amount of 3.0 g and kneaded with 1.0 g of the biphasic SSCP liquid portion using a spatula.

The resulting kneaded material was shapeable for 10 seconds to 350 seconds after the start of kneading, and the work time of the resulting kneaded material was between 10 seconds and 340 seconds based on the time point of the start of kneading.

The mixture was not deformable in 6.2 minutes (within a range of plus/minus 18 seconds) after the start of kneading even if it was pushed with a spatula. Further, when DST was measured in the same manner as in the case of Example 5, the measured value was 4.6 MPa (within a range of plus/minus 0.5 MPa).

Example 8

A biphasic SSCP liquid portion was prepared by adding 3.3 g of distilled water and CaO to 10 g of a phosphoric acid aqueous solution having a hydrogen ion concentration of pH 1.23 so that, in the biphasic SSCP liquid portion, the concentration of phosphorus was 5.09 mol/L and the concentration of calcium was 0.630 mol/L.

Further, a biphasic SSCP liquid portion was prepared by adding citric acid to the phosphoric acid aqueous solution in such a proportion that 3 mol of citric acid and the phosphoric acid aqueous solution were combined into a total volume of 1 L.

Next, a biphasic SSCP powder portion having a molar ratio of calcium to phosphorus (Ca/P) of 1.81 obtained by the same production method as in Reference Example 1 was weighed in an amount of 3.0 g and kneaded with 1.0 g of the biphasic SSCP liquid portion using a spatula.

The mixture became not deformable 9.5 minutes (a range of plus/minus 30 seconds) after the start of kneading even when the kneaded material was pushed with a spatula.

Example 9

A biphasic SSCP liquid portion was prepared by adding 10 g of distilled water and CaO to 10 g of a phosphoric acid aqueous solution having a hydrogen ion concentration of pH 1.23 so that, in the biphasic SSCP liquid portion, the concentration of phosphorus was 3.39 mol/L and the concentration of calcium was 0.420 mol/L.

Next, a biphasic SSCP powder portion having a molar ratio of calcium to phosphorus (Ca/P) of 1.81 obtained by the same production method as in Reference Example 1 was weighed in an amount of 3.0 g and kneaded with 1.0 g of the biphasic SSCP liquid portion using a spatula.

The mixture became not deformable and shapeable 10.5 minutes (a range of plus/minus 18 seconds) after the start of kneading even when the kneaded material was pushed with a spatula. The work time of this kneaded material was between 10 seconds and 600 seconds.

Further, when DST was measured in the same manner as in the case of Example 5, the measured value was 4.0 MPa (within a range of plus/minus 0.6 MPa).

Comparative Example 1

To 10 g of a phosphoric acid aqueous solution having a hydrogen ion concentration of pH 2.1, was added 10 g of distilled water to prepare a dilute phosphoric acid aqueous solution.

Further, a biphasic SSCP liquid portion was prepared by adding citric acid to the phosphoric acid aqueous solution in such a proportion that 1 mol of citric acid and the phosphoric acid aqueous solution were combined into a total volume of 1 L.

Next, a biphasic SSCP powder portion having a molar ratio of calcium to phosphorus (Ca/P) of 1.81 obtained by the same production method as in Reference Example 1 was weighed in an amount of 0.3 g and kneaded with 0.3 g of the biphasic SSCP liquid portion using a spatula.

The kneaded material was not shapeable immediately after kneading, but showed no depression 5 minutes and 30 seconds after the start of kneading even when the kneaded material was pushed with a spatula. The mixture was not deformable in 6 minutes after the start of kneading even if it was pushed with a spatula.

However, when citric acid is used, the kneaded material is set in a short time after the start of kneading, but the resulting set material has small tensile strength as described in Comparative Example 16 to be described below. Further, the set material is not sufficiently converted to HA in 24 hours after the start of kneading.

Comparative Example 2

To 10 g of a phosphoric acid aqueous solution having a hydrogen ion concentration of pH 2.1, was added 10 g of distilled water to prepare a dilute phosphoric acid aqueous solution.

Further, a biphasic SSCP liquid portion was prepared by adding citric acid to the phosphoric acid aqueous solution in such a proportion that 2 mol of citric acid and the phosphoric acid aqueous solution were combined into a total volume of 1 L.

Next, a biphasic SSCP powder portion having a molar ratio of calcium to phosphorus (Ca/P) of 1.81 obtained by the same production method as in Reference Example 1 was weighed in an amount of 0.3 g and kneaded with 0.3 g of the biphasic SSCP liquid portion using a spatula.

The kneaded material was obtained without any problem in kneading and showed no depression 3 minutes and 30 seconds after the start of kneading even when the kneaded material was pushed with a spatula. The mixture became not deformable 4 minutes after the start of kneading even if it was pushed with a spatula.

However, when citric acid is used, the kneaded material is set in a short time after the start of kneading, but the resulting set material has small tensile strength as described in Comparative Example 16 to be described below. Further, the set material is not sufficiently converted to HA in 24 hours after the start of kneading.

Comparative Example 3

To 10 g of a phosphoric acid aqueous solution having a hydrogen ion concentration of pH 2.1, was added 10 g of distilled water to prepare a dilute phosphoric acid aqueous solution.

Further, a biphasic SSCP liquid portion was prepared by adding citric acid to the phosphoric acid aqueous solution in such a proportion that 3 mol of citric acid and the phosphoric acid aqueous solution were combined into a total volume of 1 L.

Next, a biphasic SSCP powder portion having a molar ratio of calcium to phosphorus (Ca/P) of 1.81 obtained by the same production method as in Reference Example 1 was weighed in an amount of 0.3 g and kneaded with 0.3 g of the biphasic SSCP liquid portion using a spatula.

The kneaded material was obtained without any problem in kneading and showed no depression 1 minute after the start of kneading even when the kneaded material was pushed with a spatula. The mixture became not deformable 1 minute and 30 seconds after the start of kneading even when it was pushed with a spatula.

However, when citric acid is used, the kneaded material sets in a short time after the start of kneading, but the resulting set material has low tensile strength as described in Comparative Example 16 to be described below. Further, the set material is not sufficiently converted to HA in 24 hours after the start of kneading.

Comparative Example 4

To 10 g of a phosphoric acid aqueous solution having a hydrogen ion concentration of pH 2.1, was added 10 g of distilled water to prepare a dilute biphasic SSCP liquid portion. In the case of Comparative Example 4, citric acid was not used.

Next, a biphasic SSCP powder portion having a molar ratio of calcium to phosphorus (Ca/P) of 1.81 obtained by the same production method as in Reference Example 1 was weighed in an amount of 0.3 g and kneaded with 0.3 g of the biphasic SSCP liquid portion using a spatula.

However, when citric acid is used, the kneaded material sets in a short time after the start of kneading, but the resulting set material has low tensile strength as described in Comparative Example 16 to be described below. Further, the set material is not sufficiently converted to HA in 24 hours after the start of kneading.

Comparative Example 5

Eighty-five weight % phosphoric acid aqueous solution was diluted with distilled water to prepare a phosphoric acid aqueous solution.

Further, a biphasic SSCP liquid portion was prepared by adding trisodium citrate to the phosphoric acid aqueous solution in such a proportion that 1 mol of trisodium citrate and the phosphoric acid aqueous solution were combined into a total volume of 1 L.

The concentration of phosphorus in the biphasic SSCP liquid portion is 0.922 mol/L, and the biphasic SSCP liquid portion does not contain calcium.

Next, a biphasic SSCP powder portion having a molar ratio of calcium to phosphorus (Ca/P) of 1.81 obtained by the same production method as in Reference Example 1 was weighed in an amount of 3.0 g and kneaded with 1.0 g of the biphasic SSCP liquid portion using a spatula.

The kneaded material did not set within 10 minutes after the start of kneading.

The mixture was not deformable at a time point of 15.2 minutes (within a range of plus/minus 36 seconds) after the start of kneading even if it was pushed with a spatula.

Comparative Example 6

A biphasic SSCP liquid portion comprising 85 weight % phosphoric acid aqueous solutions was prepared.

Next, a biphasic SSCP powder portion having a molar ratio of calcium to phosphorus (Ca/P) of 1.81 obtained by the same production method as in Reference Example 1 was weighed in an amount of 0.3 g and kneaded with 0.3 g of the biphasic SSCP liquid portion using a spatula.

A kneaded material was not able to be obtained by kneading since the biphasic SSCP adhered to the spatula.

Comparative Example 7

Distilled water was added to 85 weight % phosphoric acid aqueous solution to prepare a biphasic SSCP liquid portion comprising 43 weight % phosphoric acid aqueous solution.

Next, a biphasic SSCP powder portion having a molar ratio of calcium to phosphorus (Ca/P) of 1.81 obtained by the same production method as in Reference Example 1 was weighed in an amount of 0.3 g and kneaded with 0.3 g of the biphasic SSCP liquid portion using a spatula.

A kneaded material was not able to be obtained by kneading since the biphasic SSCP adhered to the spatula.

Comparative Example 8

Distilled water was added to 85 weight % phosphoric acid aqueous solution to prepare a biphasic SSCP liquid portion comprising 21 weight % phosphoric acid aqueous solution.

Next, a biphasic SSCP powder portion having a molar ratio of calcium to phosphorus (Ca/P) of 1.81 obtained by the same production method as in Reference Example 1 was weighed in an amount of 0.3 g and kneaded with 0.3 g of the biphasic SSCP liquid portion using a spatula.

A kneaded material was able to be obtained by kneading, but the kneaded material was not shapeable since the water content was low.

Comparative Example 9

Distilled water was added to 85 weight % phosphoric acid aqueous solution to prepare a biphasic SSCP liquid portion comprising 10 weight % phosphoric acid aqueous solution.

Next, a biphasic SSCP powder portion having a molar ratio of calcium to phosphorus (Ca/P) of 1.81 obtained by the same production method as in Reference Example 1 was weighed in an amount of 0.3 g and kneaded with 0.3 g of the biphasic SSCP liquid portion using a spatula.

A kneaded material was able to be obtained by kneading, but the kneaded material was not shapeable. The kneaded material showed no depression in 16 minutes after the start of kneading even if it was pushed with a spatula.

Comparative Example 10

Distilled water was added to 85 weight % phosphoric acid aqueous solution to prepare a biphasic SSCP liquid portion comprising 5 weight % phosphoric acid aqueous solution.

Next, a biphasic SSCP powder portion having a molar ratio of calcium to phosphorus (Ca/P) of 1.81 obtained by the same production method as in Reference Example 1 was weighed in an amount of 0.3 g and kneaded with 0.3 g of the biphasic SSCP liquid portion using a spatula.

A kneaded material was able to be obtained by kneading, but the kneaded material was not shapeable. The kneaded material showed no depression in 20 minutes after the start of kneading even if it was pushed with a spatula.

Comparative Example 11

Distilled water was added to 85 weight % phosphoric acid aqueous solution to prepare a biphasic SSCP liquid portion comprising 2.5 weights phosphoric acid aqueous solution.

Next, a biphasic SSCP powder portion having a molar ratio of calcium to phosphorus (Ca/P) of 1.81 obtained by the same production method as in Reference Example 1 was weighed in an amount of 0.3 g and kneaded with 0.3 g of the biphasic SSCP liquid portion using a spatula.

A kneaded material was able to be obtained by kneading, but the kneaded material did not set.

Comparative Example 12

Distilled water was added to 85 weight % phosphoric acid aqueous solution to prepare a biphasic SSCP liquid portion comprising 1.25 weight % phosphoric acid aqueous solution.

Next, a biphasic SSCP powder portion having a molar ratio of calcium to phosphorus (Ca/P) of 1.81 obtained by the same production method as in Reference Example 1 was weighed in an amount of 0.3 g and kneaded with 0.3 g of the biphasic SSCP liquid portion using a spatula.

A kneaded material was able to be obtained by kneading, but the kneaded material did not set.

Comparative Example 13

Distilled water was added to 85 weight % phosphoric acid aqueous solution to prepare 2.5 weight % phosphoric acid aqueous solution.

Further, a biphasic SSCP liquid portion was prepared by adding trisodium citrate to the phosphoric acid aqueous solution in such a proportion that 1 mol of trisodium citrate and the phosphoric acid aqueous solution were combined into a total volume of 1 L.

Next, a biphasic SSCP powder portion having a molar ratio of calcium to phosphorus (Ca/P) of 1.81 obtained by the same production method as in Reference Example 1 was weighed in an amount of 0.3 g and kneaded with 0.3 g of the biphasic SSCP liquid portion using a spatula.

The kneaded material was easily obtained by kneading and shapeable, but showed depression in 25 minutes after the start of kneading when the kneaded material was pushed with a spatula.

Comparative Example 14

A biphasic SSCP liquid portion was prepared by adding trisodium citrate to the 85 weight % phosphoric acid aqueous solution in such a proportion that 3 mol of trisodium citrate and the 85 weight % phosphoric acid aqueous solution were combined into a total volume of 1 L.

Next, a biphasic SSCP powder portion having a molar ratio of calcium to phosphorus (Ca/P) of 1.81 obtained by the same production method as in Reference Example 1 was weighed in an amount of 0.3 g and kneaded with 0.3 g of the biphasic SSCP liquid portion using a spatula.

The kneaded material was easily obtained by kneading and shapeable, but showed depression in 15 minutes after the start of kneading when the kneaded material was pushed with a spatula.

Figure 2:
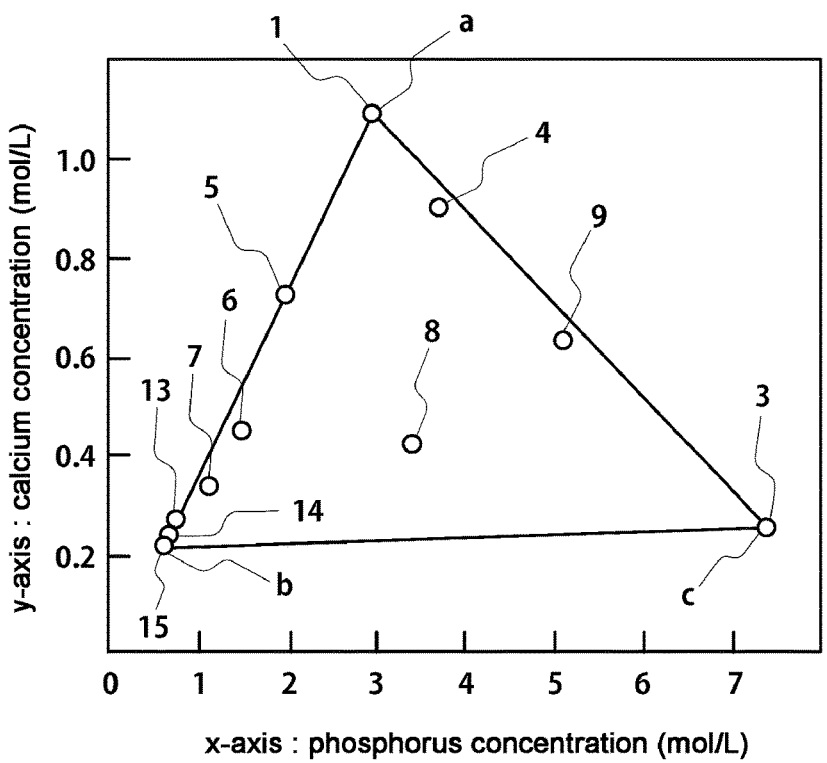
FIG. 2 is a graph showing the biphasic SSCP liquid portions used in Examples by taking the phosphorus concentration (mol/L) along the horizontal axis and the calcium concentration (mol/L) along the vertical axis.

FIG. 2 is a graph showing the biphasic SSCP liquid portions used in Examples 1, 3 to 9, and 13 to 15 corresponding to reference numerals 1, 3 to 9, and 13 to 15, respectively, by taking the phosphorus concentration (mol/L) along the horizontal axis and the calcium concentration (mol/L) along the vertical axis.

In FIG. 2, when the phosphorus concentration (mol/L) of the biphasic SSCP liquid portion is taken along the x-axis and the calcium concentration (mol/L) of the biphasic SSCP liquid portion is taken along the y-axis, the values (x, y) of the phosphorus concentration and the calcium concentration of the biphasic SSCP liquid portion are preferably included in the range of a triangle (including straight lines) obtained by connecting the three points of reference character a (2.96, 1.09), reference character b (0.592, 0.218), and reference character c (7.38, 0.25) by straight lines, respectively.

When the calcium concentration and the phosphorus concentration of the biphasic SSCP liquid portion to be used in the present invention are within the above range, the work time when the biphasic SSCP powder portion and the biphasic SSCP liquid portion are kneaded will be in a range of 10 seconds to 600 seconds at room temperature, and a hard tissue regeneration material that is easily shaped will be obtained.

The set material of the biphasic SSCP is a calcium-deficient apatite having the range of Ca deficiency.

In the present invention, the biphasic SSCP liquid portion shown in FIG. 2 provides particularly satisfactory operability. A hard tissue regeneration material good in kneadability can be provided by using a sodium citrate compound in combination with the biphasic SSCP liquid portion.

Further, the biphasic SSCP has a character that the hydrogen ion concentration, phosphorus concentration, and calcium concentration can be changed in a wide range, and the work time and setting time can be freely controlled in a range of 10 seconds to 600 seconds.

Example 10

X-Ray Analysis Results of Biphasic SSCP

The biphasic SSCP liquid portion used in Example 1 was diluted by adding 3.0 g of distilled water to 1.0 g of the biphasic SSCP liquid portion.

A plurality of kneaded materials was obtained by kneading 0.18 g of the biphasic SSCP powder portion used in Example 1 and 0.06 g of the dilute biphasic SSCP liquid portion for 30 seconds at a room temperature of 23±1° C. and a relative humidity of 50±10%. Immediately after kneading for 30 seconds, all the kneaded materials were stored under the conditions of a temperature of 23° C. and a relative humidity of 100%.

A set material was removed in 4 hours, 8 hours, 24 hours, and 72 hours, respectively, after the start of storage, and the reaction was stopped by replacing the solution by acetone. The X-ray diffraction test was performed in a state where the set material was sufficiently dried.

Figure 6:
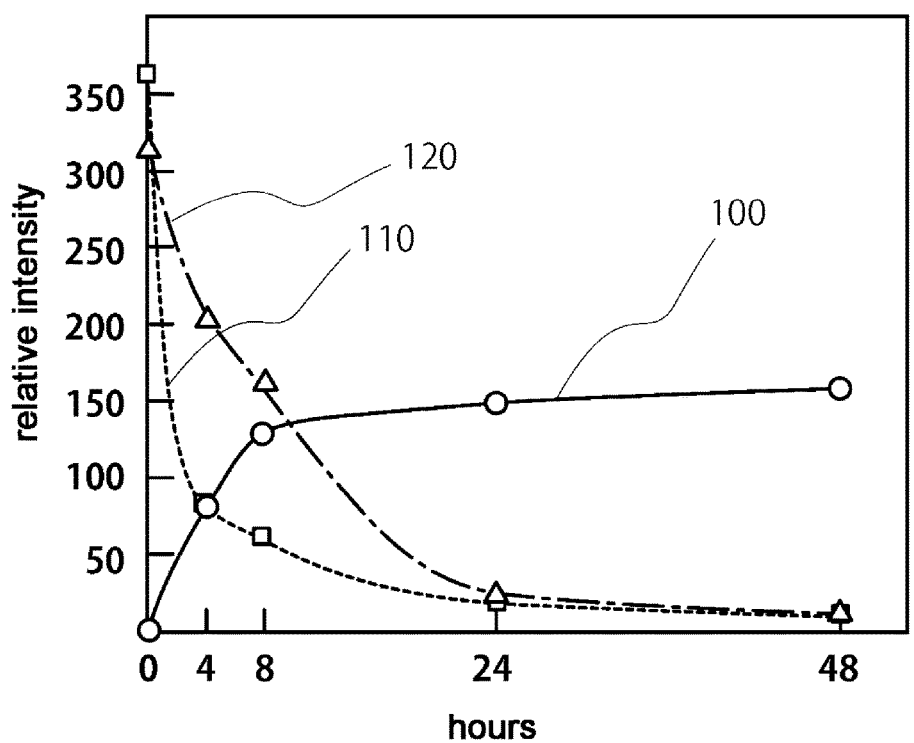
FIG. 6 is a graph showing the change with time of the content of TTCP, $\alpha$-TCP, and HA in SSCP.

FIG. 6 is a graph showing the change with time of the content of TTCP, α-TCP, and HA in biphasic SSCP. In FIG. 6, reference numeral 100 represents HA, reference numeral 110 represents TTCP, and reference numeral 120 represents α-TCP.

In the X-ray diffraction test, TTCP was specified by the peaks appearing at a 2θ value of near 29.8 and near 29.3.

Similarly, α-TCP was specified by the peaks appearing at a 2θ value of near 30.8 and near 22.9. Similarly, HA was specified by the peaks appearing at a 2θ value of near 31.8 and near 25.9.

These values are summarized in Table 2.

Note that 2θ represents the Bragg angle of a lattice plane of a crystal in the X-ray analysis test. The unit of 2θ is the angle (degree).

TABLE 2

| SSCP | Angle degree 2θ | Hour (h) | | | | |
|---|---|---|---|---|---|---|
| | | 0 | 4 | 8 | 24 | 48 |
| | | Peak Intensity (Relative Intensity) | | | | |
| TTCP | 29.88 | 619 | 124 | 60 | 16 | 6 |
| | 29.32 | 363 | 83 | 63 | 18 | 11 |
| α-TCP | 30.8 | 314 | 202 | 162 | 18 | 13 |
| | 22.98 | 145 | 142 | 65 | 30 | 25 |
| HA | 31.8 | 126 | 115 | 150 | 245 | 277 |
| | 25.9 | 0 | 80 | 129 | 148 | 159 |

In FIG. 6, TTCP was specified by the peak appearing at a 2θ value of near 29.3; α-TCP was specified by the peak appearing at a 2θ value of near 30.8; and HA was specified by the peak appearing at a 2θ value of near 25.9.

Each peak intensity (relative intensity) was measured in 4 hours, 8 hours, 24 hours, and 72 hours after the start of storage and recorded in FIG. 6.

The extent of decrease of TTCP and α-TCP with time and the extent of increase of HA with time can be estimated by pursuing the change with time of the peak intensity of TTCP, the peak intensity of α-TCP, and the peak intensity of HA in the X-ray diffraction test.

FIG. 6 shows that the biphasic SSCP used in Example 10 has completed the reaction in about 24 hours after the completion of kneading.

Example 11

Physical Properties Test of Biphasic SSCP

The biphasic SSCP used in Example 11 is completely the same as that used in Example 10.

A kneaded material was obtained by kneading 0.18 g of the biphasic SSCP powder portion used in Example 1 and 0.06 g of the dilute biphasic SSCP liquid portion for 2 minutes and 30 seconds at a room temperature of 23±1° C. and a relative humidity of 50±10%, and then the kneaded material was charged into a mold for preparing a DTS sample. The kneaded material charged into the mold for preparing a DTS sample was stored for 4 hours under the conditions of a temperature of 37° C. and a relative humidity of 100%.

Next, a set material was removed from the mold for preparing a DTS sample and stored for 20 hours at 37° C. in 15 ml of distilled water.

The set material was removed from the distilled water after the lapse of 24 hours from the start of kneading, and the reaction was stopped by replacing water contained in the set material with acetone. Then, DTS (diametral tensile strength) of the set material was measured.

The results are shown in Table 7.

Figure 49:
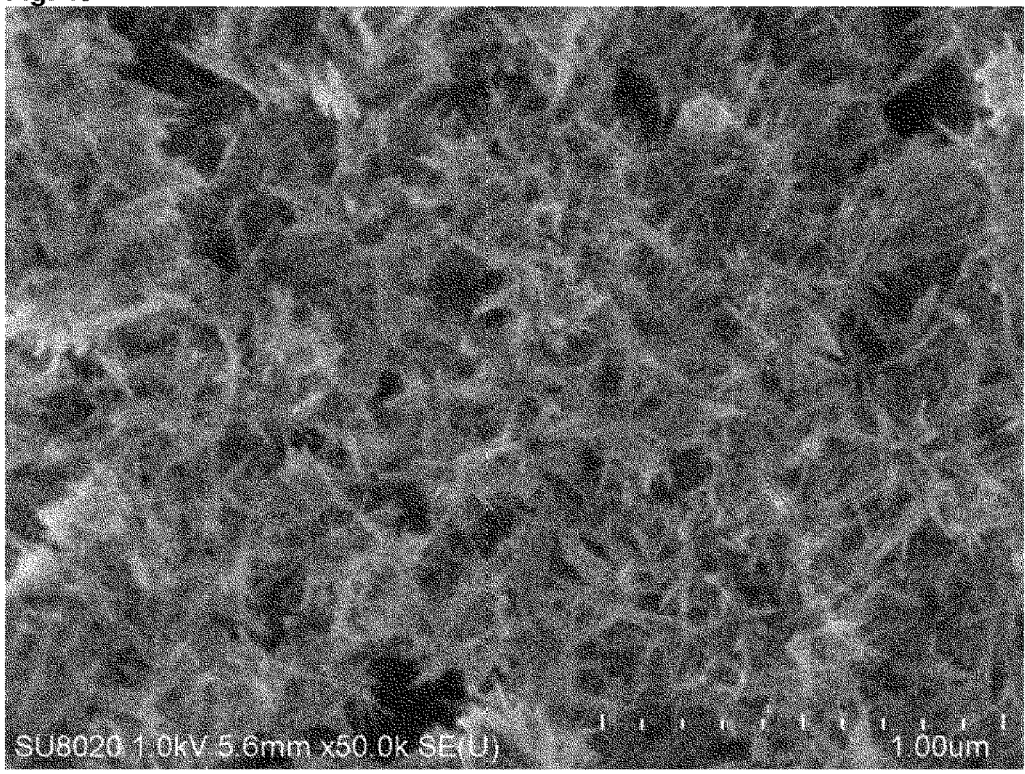
FIG. 49 is a photograph substituted for a drawing of the surface of a set material enlarged by 50000 times with an electron microscope, after storing a set material obtained by the same operation as in Example 11 for 24 hours at 37° C. in distilled water.

FIG. 49 is a photograph substituted for a drawing of a set material enlarged by 50000 times with an electron microscope, after storing a set material removed from the mold for preparing a DTS sample for 24 hours at 37° C. in distilled water.

Figure 50:
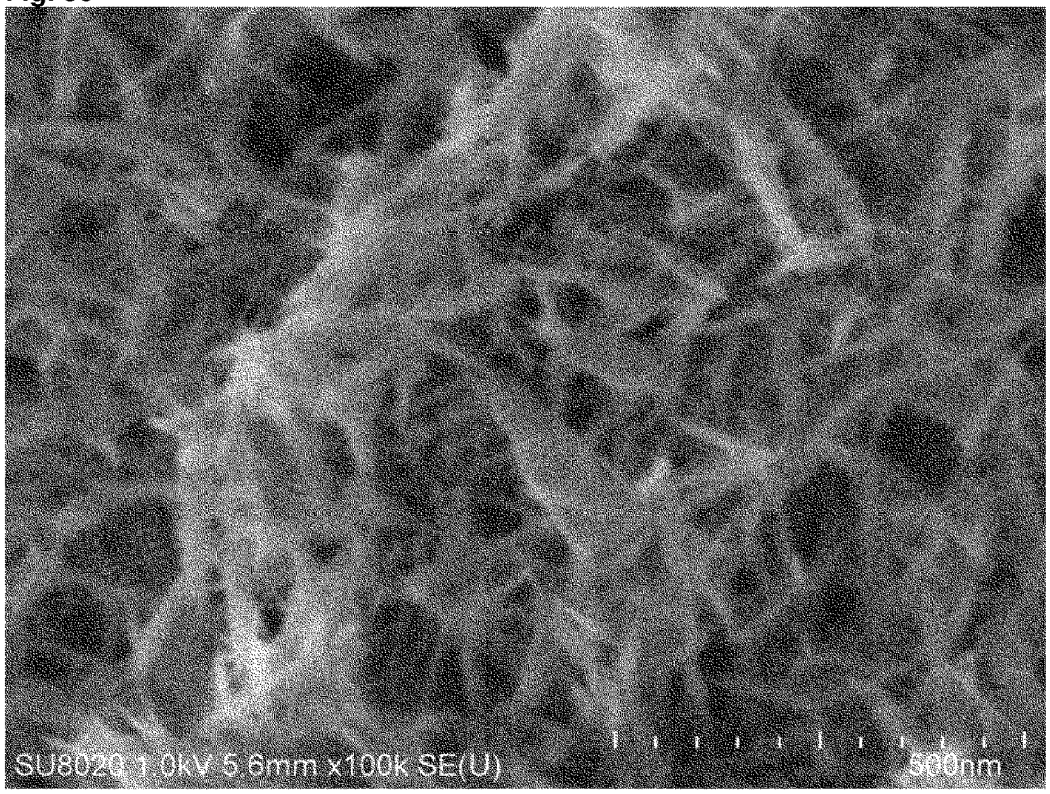
FIG. 50 is a photograph substituted for a drawing of the surface of a set material enlarged by 100000 times with an electron microscope, after storing a set material obtained by the same operation as in Example 11 for 24 hours at 37° C. in distilled water.

FIG. 50 is a photograph substituted for a drawing of a set material enlarged by 100000 times with an electron microscope, after storing a set material removed from the mold for preparing a DTS sample for 24 hours at 37° C. in distilled water.

FIG. 49 and FIG. 50 clearly show that the biphasic SSCP obtained by the present invention is formed from dense short fiber-like HA crystals.

39

The dense short fiber-like crystal comprising the biphasic SSCP has properties that it is relatively easily absorbed by osteoclast and replaced to existing bone by the action of osteoblast while maintaining the shape of the biphasic SSCP.

Example 12

Measurement of Work Time of Biphasic SSCP

The biphasic SSCP used in Example 12 is completely the same as that used in Example 10.

A kneaded material was obtained by kneading 0.18 g of the biphasic SSCP powder portion used in Example 1 and 0.06 g of the dilute biphasic SSCP liquid portion for 2 minutes and 30 seconds at a room temperature of 23±1° C. and a relative humidity of 50±10%, and the kneaded material was charged into a measuring mold.

The tip of a Gilmore needle was dropped to the surface of the kneaded material in the measuring mold from a height about 5 mm above the surface of the kneaded material at intervals of 15 seconds starting from 2 minutes after the start of kneading to measure the degree of setting of the biphasic SSCP used in Example 12 from the degree of deformation of the kneaded material.

Figure 7:
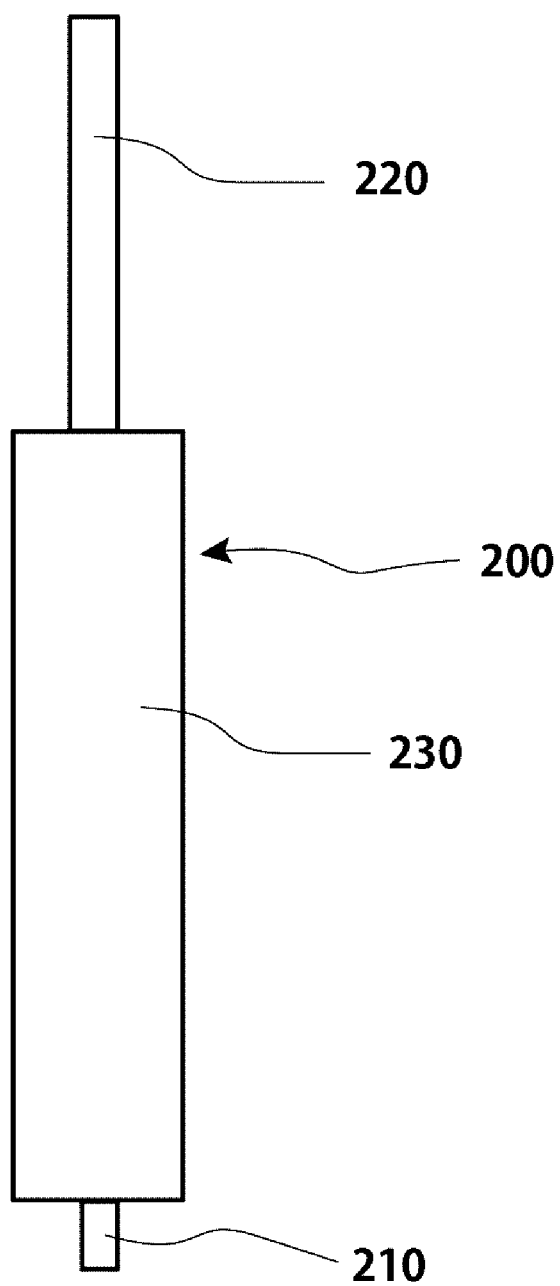
FIG. 7 FIG. 7 is a schematic diagram showing the state where a Gilmore needle is observed in the perpendicular direction to the longitudinal direction of the Gilmore needle.
Figure 8:
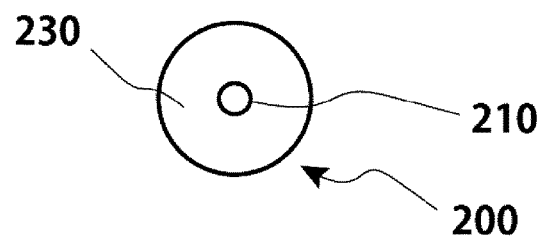
FIG. 8 is a schematic diagram showing the state where a Gilmore needle is observed from the tip of the Gilmore needle.

FIG. 7 and FIG. 8 are schematic diagrams of a Gilmore needle used in the present invention. FIG. 7 is a schematic diagram showing the state where a Gilmore needle 200 is observed in the perpendicular direction to the longitudinal direction of the Gilmore needle 200, and FIG. 8 is a schematic diagram showing the state where a Gilmore needle 200 is observed from the tip 210 of the Gilmore needle.

The length from the tip 210 of the Gilmore needle used in the present invention to the rear end 220 of the Gilmore needle is 185 mm. Further, the diameter of the body 230 of the Gilmore needle is 24.5 mm, and the diameter of the tip 210 of the Gilmore needle is 2.12 mm.

The biphasic SSCP used in Example 12 had a viscosity that was injectable with a syringe for 2 minutes and 15 seconds from the time when 30 seconds elapsed from the start of kneading at room temperature in a range of 23±1° C. The biphasic SSCP was in a kneadable state for 4 minutes to 4 minutes and 45 seconds from the time when 30 seconds elapsed from the start of kneading, and the indentation of the Gilmore needle was observed on the surface of the set material.

From 5 minutes and 15 seconds on from the start of kneading, the indentations of the Gilmore needle observed on the surface of the set materials were in the same degree, and the set materials could not be shaped.

After the lapse of 6 minutes from the start of kneading, a gloss that shows the fact that the surface has got wet with a liquid disappeared from the surface of the set material. Further, when the set material was tapped with a spatula, a tap tone similar to that in the case of tapping metal, which was definitely different from the tap tone of the material before setting, was able to be identified.

As described above, the setting of the biphasic SSCP was identified after the lapse of 6 minutes from the time when 30 seconds elapsed from the start of kneading.

Example 13

Measurement of Work Time of Biphasic SSCP

The biphasic SSCP liquid portion used in Example 1 was diluted by adding 3.0 g of distilled water to 1.0 g of the biphasic SSCP liquid portion.

A kneaded material was obtained by kneading 0.18 g of the biphasic SSCP powder portion used in Example 1, 0.75 weight % of PVP (polyvinyl pyrrolidone) based on biphasic SSCP, and 0.06 g of the dilute biphasic SSCP liquid portion for 30 seconds at a room temperature of 23±1° C. and a relative humidity of 50±10%.

In the same manner as in the case of Example 12, the tip of a Gilmore needle was dropped to the surface of the kneaded material in the measuring mold from a height 5 mm above the surface of the kneaded material at intervals of 15 seconds starting from 2 minutes after the start of kneading to measure the degree of setting of the biphasic SSCP used in Example 13 from the degree of deformation of the kneaded material.

This experiment was repeated 4 times. The results are shown in Table 3.

TABLE 3

| | Allowed Time For Injection | Allowed Time For Shape Forming | Setting Time |
|---|---|---|---|
| 1st Time | 2 minutes 15 seconds | 5 minutes 15 seconds | 6 minutes 0 seconds |
| 2nd Time | 2 minutes 15 seconds | 5 minutes 15 seconds | 6 minutes 0 seconds |
| 3rd Time | 2 minutes 15 seconds | 5 minutes 30 seconds | 6 minutes 15 seconds |
| 4th Time | 2 minutes 15 seconds | 5 minutes 15 seconds | 6 minutes 0 seconds |
| Average | 2 minutes 15 seconds | 5 minutes 18 seconds | 6 minutes 3 seconds |

As seen from Table 3, the kneaded material of the biphasic SSCP maintained an injectable state where the kneaded material can be injected into arbitrary places with a syringe or the like for 2 minutes and 15 seconds on average from the time when 30 seconds elapsed from the start of kneading.

Here, the injectable state means a state where the kneaded material has fluidity, which means that the kneaded material does not have a definite shape. When the biphasic SSCP according to the present invention is in an injectable state, the biphasic SSCP can be injected into arbitrary places with a syringe or the like.

Further, the kneaded material maintained a shapeable state for 5 minutes and 18 seconds on average from the time when 30 seconds elapsed from the start of kneading.

Here, the shapeable state means that the kneaded material is deformable and has a definite shape.

As shown in Table 3, the allowed time for injection is for 2 minutes and 15 seconds from the time when 30 seconds elapsed from the start of kneading, and the allowed time for shape forming is for about 3 minutes after the allowed time for injection of 2 minutes and 15 seconds from the time when 30 seconds elapsed from the start of kneading. In the present invention, the sum of the allowed time for injection and the allowed time for shape forming is the work time.

The end point of the average work time in Example 13 was 5 minutes and 18 seconds.

The kneaded material set at a stage when 6 minutes and 3 seconds on average elapsed from the time when 30 seconds have elapsed from the start of kneading.

The biphasic SSCP according to Example 13 can be filled into the defects of teeth and bone with enough time since the biphasic SSCP has time to show a shapeable state of about 3 minutes.

Further, since the biphasic SSCP according to Example 13 sets in a short time, the skin near the defects of teeth and bone can be sutured as necessary after the defects of teeth and bone are filled with the biphasic SSCP. Thus, the operation can be completed in a short time.

Example 14

Measurement of Work Time of Biphasic SSCP

The biphasic SSCP liquid portion used in Example 1 was diluted by adding 3.5 g of distilled water to 1.0 g of the biphasic SSCP liquid portion.

Except the above, the experiment was performed in completely the same manner as in the case of Example 13. The results are shown in Table 4.

TABLE 4

|  | Allowed Time For Injection | Allowed Time For Shape Forming | Setting Time |
| --- | --- | --- | --- |
| 1st Time | 2 minutes 15 seconds | 6 minutes 0 seconds | 6 minutes 45 seconds |
| 2nd Time | 2 minutes 30 seconds | 6 minutes 15 seconds | 7 minutes 0 seconds |
| 3rd Time | 2 minutes 30 seconds | 6 minutes 15 seconds | 7 minutes 0 seconds |
| 4th Time | 2 minutes 30 seconds | 6 minutes 15 seconds | 7 minutes 0 seconds |
| Average | 2 minutes 26 seconds | 6 minutes 11 seconds | 6 minutes 56 seconds |

As shown in Table 4, the allowed time for injection is for 2 minutes and 26 seconds on average, and the allowed time for shape forming is for about 4 minutes from the allowed time for injection of 2 minutes and 26 seconds.

The end point of the average work time in Example 14 was 6 minutes and 11 seconds.

Example 15

Measurement of Work Time of Biphasic SSCP

The biphasic SSCP liquid portion used in Example 1 was diluted by adding 4.0 g of distilled water to 1.0 g of the biphasic SSCP liquid portion.

Except the above, the experiment was performed in completely the same manner as in the case of Example 13. The results are shown in Table 5.

TABLE 5

|  | Allowed Time For Injection | Allowed Time For Shape Forming | Setting Time |
| --- | --- | --- | --- |
| 1st Time | 3 minutes 0 seconds | 7 minutes 15 seconds | 8 minutes 0 seconds |
| 2nd Time | 3 minutes 0 seconds | 7 minutes 15 seconds | 8 minutes 0 seconds |
| 3rd Time | 3 minutes 15 seconds | 7 minutes 30 seconds | 8 minutes 0 seconds |
| 4th Time | 2 minutes 45 seconds | 7 minutes 30 seconds | 8 minutes 15 seconds |
| Average | 3 minutes 0 seconds | 7 minutes 22 seconds | 8 minutes 3 seconds |

As shown in Table 5, the allowed time for injection is for 3 minutes and 0 seconds on average, and the allowed time for shape forming is for 4 minutes or more starting from the allowed time for injection of 3 minutes and 0 seconds.

The end point of the average work time in Example 15 was 7 minutes and 22 seconds.

Comparative Example 15

Measurement of Work Time of Biphasic SSCP

A 1 mol/L citric acid aqueous solution was used instead of the biphasic SSCP liquid portion used in Example 1. Note that the citric acid aqueous solution was used without dilution.

Except the above, the experiment was performed in completely the same manner as in the case of Example 13. The results are shown in Table 6.

TABLE 6

|  | Allowed Time For Injection | Allowed Time For Shape Forming | Setting Time |
| --- | --- | --- | --- |
| 1st Time | 5 minutes 30 seconds | 6 minutes 45 seconds | 7 minutes 15 seconds |
| 2nd Time | 6 minutes 0 seconds | 7 minutes 0 seconds | 7 minutes 30 seconds |
| 3rd Time | 5 minutes 30 seconds | 7 minutes 0 seconds | 7 minutes 30 seconds |
| Average | 5 minutes 40 seconds | 6 minutes 55 seconds | 7 minutes 25 seconds |

The kneaded material according to Comparative Example 15 was not integrated even when it was kneaded, and the kneading was difficult.

In the same manner as in the case of Example 12, the tip of a Gilmore needle was dropped to the surface of the kneaded material in the measuring mold from a height 5 mm above the surface of the kneaded material at intervals of 15 seconds starting from 2 minutes after the start of kneading to measure the degree of setting of the biphasic SSCP used in Comparative Example 15 from the degree of deformation of the kneaded material.

The kneaded material of the biphasic SSCP has fluidity until 5 minutes and 40 seconds on average have elapsed from the time when 30 seconds elapsed from the start of kneading. Therefore, even when an indentation is formed with the Gilmore needle, the indentation will be buried since the kneaded material has fluidity. However, the kneaded material was clay like and not able to be injected with a syringe.

The kneaded material was deformable until 6 minutes and 55 seconds on average elapsed from the time when 30 seconds elapsed from the start of kneading.

The kneaded material was not deformable in 7 minutes and 25 seconds on average from the time when 30 seconds elapsed from the start of kneading.

However, even when a set material formed from the kneaded material was tapped with a spatula at the time when 10 minutes elapsed from the time when 30 seconds elapsed from the start of kneading, a tap tone similar to that in the case of tapping metal was not able to be heard.

In the case of the citric acid-containing biphasic SSCP used in Comparative Example 15, the kneaded material loses fluidity when 5 minutes and 40 seconds on average elapsed from the time when 30 seconds elapsed from the start of kneading. The time from the time when fluidity is lost to the time when the kneaded material is not deformable is 1 minute and 15 seconds on average. Thus, it was found that the operation of filling the defects of teeth and bone with the citric acid-containing biphasic SSCP was extremely limited.

Example 16

Physical Properties Test of Biphasic SSCP

Instead of the biphasic SSCP powder portion used in the case of Example 11, was used a mixture of an α-TCP powder and a TTCP powder, in which the α-TCP powder and the TTCP powder were mixed so that the same molar ratio as that of the biphasic SSCP powder portion used in Example 11 was obtained.

Except the above, the test was performed in completely the same manner as in the case of Example 11.

The results of DTS of the resulting set material are shown in Table 8.

Comparative Example 16

Physical Properties Test of Biphasic SSCP

A 1 mol/L citric acid aqueous solution was used instead of the biphasic SSCP liquid portion used in Example 1. Note that the citric acid aqueous solution was used without dilution.

Except the above, the test was performed in the same manner as in the case of Example 11.

Next, the DTS test was performed under the completely same conditions as in the case of Example 11. The results are shown in Table 9.

It was found that when a set material was obtained by using citric acid, the strength of the set material was significantly reduced as compared with the results of a set material in which citric acid was not used.

Next, the kneaded material was stored by the same operation as in Example 10. A set material was removed after the lapse of 24 hours from the start of storage, and the reaction was stopped by replacing the solution by acetone. The X-ray diffraction test was performed in a state where the set material was sufficiently dried.

The results are shown in Table 10.

It can be seen that when citric acid is used, the peak intensity (relative intensity) of HA at the time when 24 hours elapsed after the start of storage is 43, which is ⅓ or less as compared with that in the case of Example 10.

As shown in Comparative Example 16, it was found that when citric acid was used, the biphasic SSCP was not replaced by existing bone in a short time.

TABLE 7

|  | Diameter (mm) | Thickness (mm) | Load (N) | MPa |
|---|---|---|---|---|
| 1st Time | 6.03 | 3.07 | 113.70 | 3.91 |
| 2nd Time | 6.00 | 3.10 | 113.70 | 3.89 |
| 3rd Time | 6.03 | 3.08 | 127.00 | 4.36 |
| 4th Time | 6.03 | 3.08 | 136.00 | 4.66 |
| 5th Time | 6.02 | 3.13 | 124.50 | 4.21 |
| Average | 6.02 | 3.09 | 122.98 | 4.21 |
| Standard Deviation | 0.01 | 0.02 | 9.49 | 0.32 |

TABLE 8

|  | Diameter (mm) | Thickness (mm) | Load (N) | MPa |
|---|---|---|---|---|
| 1st Time | 6.03 | 3.08 | 86.50 | 2.97 |
| 2nd Time | 6.05 | 3.06 | 96.20 | 3.31 |
| 3rd Time | 6.04 | 3.10 | 85.20 | 2.90 |
| 4th Time | 6.04 | 3.07 | 105.50 | 3.62 |
| 5th Time | 5.99 | 3.08 | 86.00 | 2.97 |
| Average | 6.03 | 3.08 | 91.88 | 3.15 |
| Standard Deviation | 0.02 | 0.01 | 8.84 | 0.31 |

TABLE 9

|  | Diameter (mm) | Thickness (mm) | Load (N) | MPa |
|---|---|---|---|---|
| 1st Time | 6.02 | 3.03 | 27.00 | 0.94 |
| 2nd Time | 6.00 | 3.05 | 31.00 | 1.08 |
| 3rd Time | 6.00 | 3.04 | 27.00 | 0.94 |
| 4th Time | 5.99 | 3.01 | 31.50 | 1.11 |
| 5th Time | 6.02 | 3.00 | 24.20 | 0.85 |
| Average | 6.01 | 3.03 | 28.14 | 0.99 |
| Standard Deviation | 0.01 | 0.02 | 3.07 | 0.11 |

TABLE 10

| SSCP | Angle degree 2θ | Hour (h) 24 Peak Intensity (Relative Intensity) |
|---|---|---|
| TTCP | 29.88 | 266 |
|  | 29.32 | 212 |
| α-TCP | 30.8 | 391 |
|  | 22.98 | 213 |
| HA | 31.8 | 108 |
|  | 25.9 | 43 |

Example 17

Bone Formation by Biphasic SSCP Using Mouse

The skin part covering the skull of a mouse was cut to expose the skull. A hole having a diameter of 4 mm was formed in the skull using a surgery drill.

The diameter of the hole was set to 4 mm because 4 mm is the value of the critical gap in which spontaneous closure by bone cannot be expected.

Figure 51:
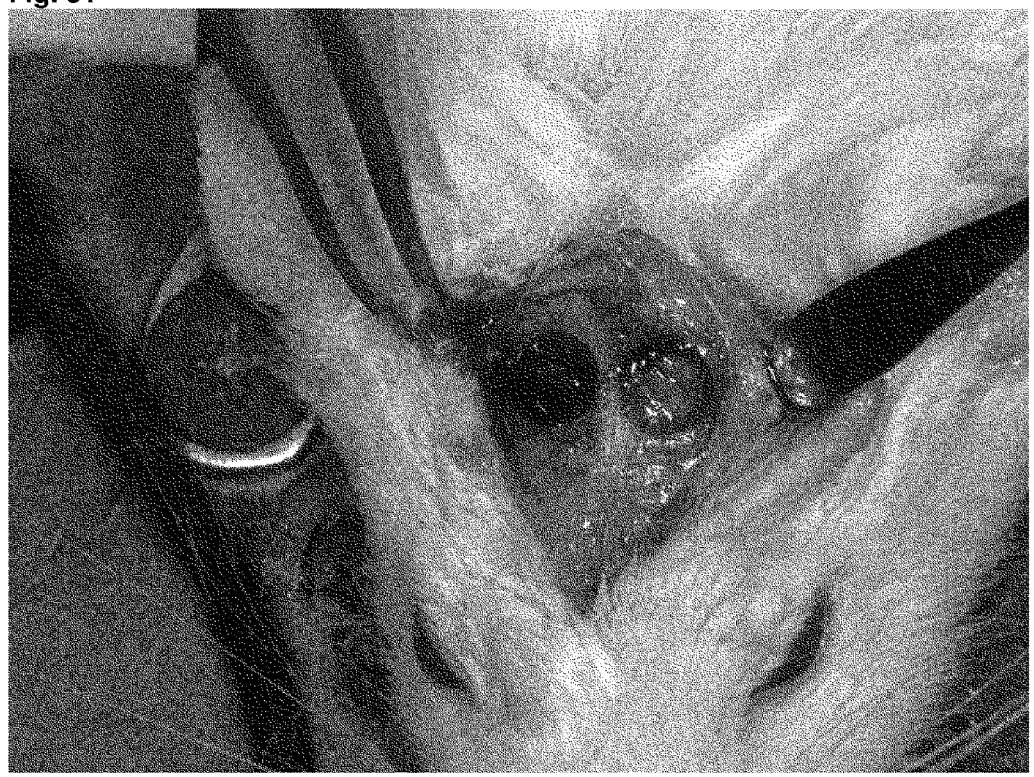
FIG. 51 is a photograph substituted for a drawing showing the state where a hole is formed in the skull of a mouse.
Figure 52:
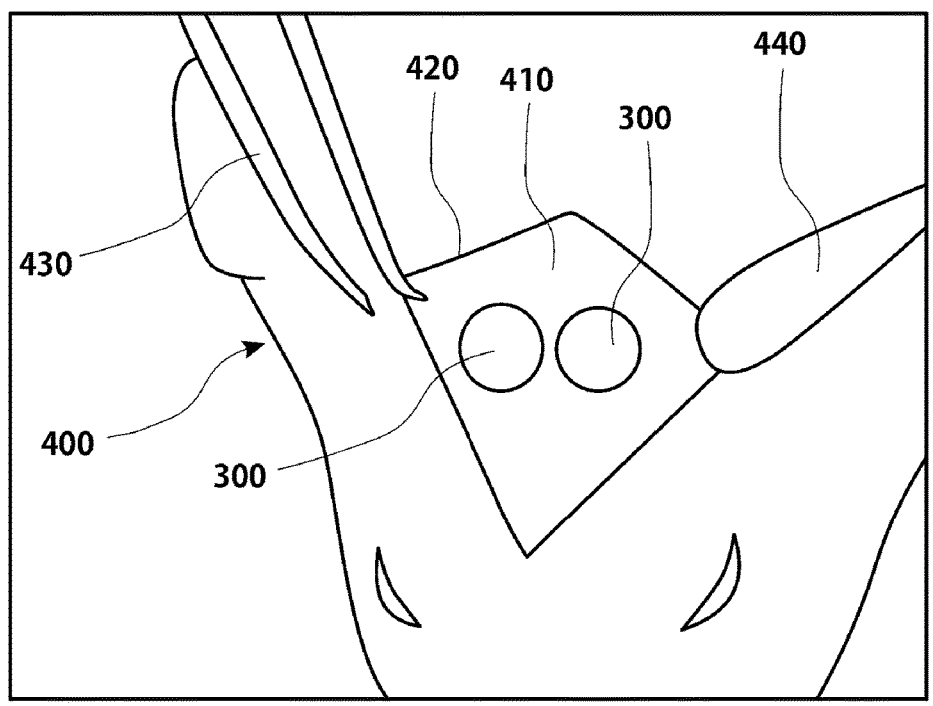
FIG. 52 is a schematic diagram showing the state where a hole is formed in the skull of a mouse.

FIG. 51 is a photograph substituted for a drawing showing the state where a hole is formed in the skull of a mouse. Further, FIG. 52 is a schematic diagram showing the state where a hole is formed in the skull of a mouse.

A hole 300 is formed in the skull 410 of a mouse 400. An operative wound 420 of the mouse 400 is extended by forceps 430 and a hook 440.

Next, the hole 300 was filled with a kneaded material 450 of the biphasic SSCP used in Example 10.

Figure 53:
FIG. 53 is a photograph substituted for a drawing showing the state where a hole formed in the skull of a mouse is filled with biphasic SSCP.

FIG. 53 is a photograph substituted for a drawing showing the state where a hole formed in the skull of a mouse is filled with biphasic SSCP. Further, FIG. 54 is a schematic diagram showing the state where a hole formed in the skull of a mouse is filled with biphasic SSCP.

Figure 54:
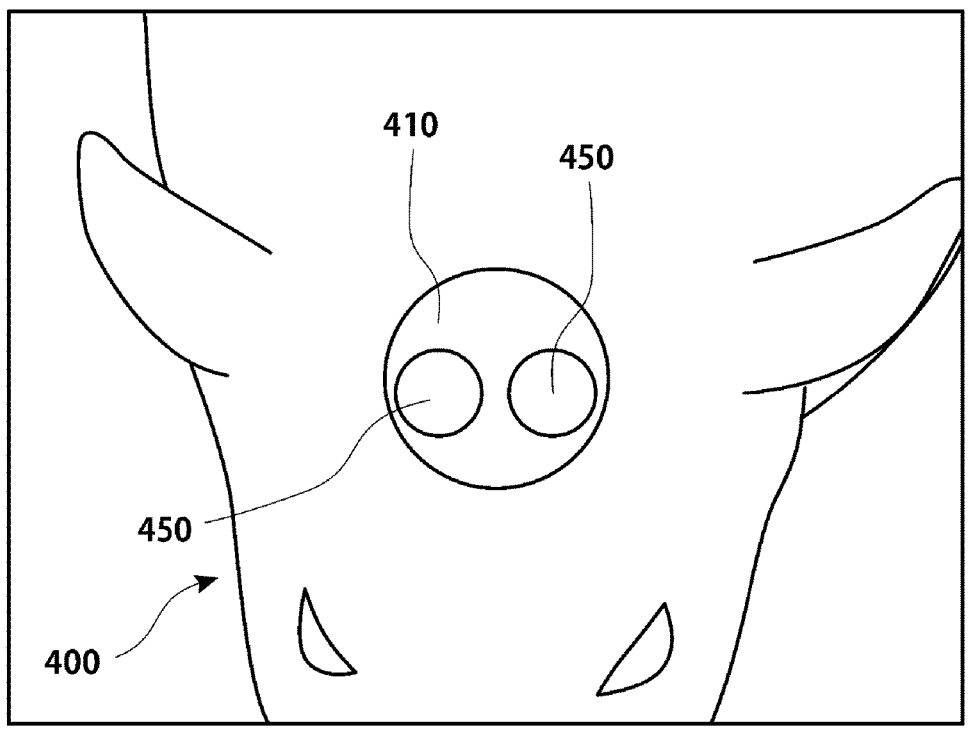
FIG. 54 is a schematic diagram showing the state where a hole formed in the skull of a mouse is filled with biphasic SSCP.

As shown in FIG. 53 and FIG. 54, the hole 300 formed in the skull 410 of the mouse 400 is filled with the kneaded material 450 of the biphasic SSCP.

Subsequently, the skin part was reconstituted to cover the hole.

The hole was photographed immediately after filling, 3 weeks after filling, and 8 weeks after filling with the biphasic SSCP, respectively.

Figure 9:
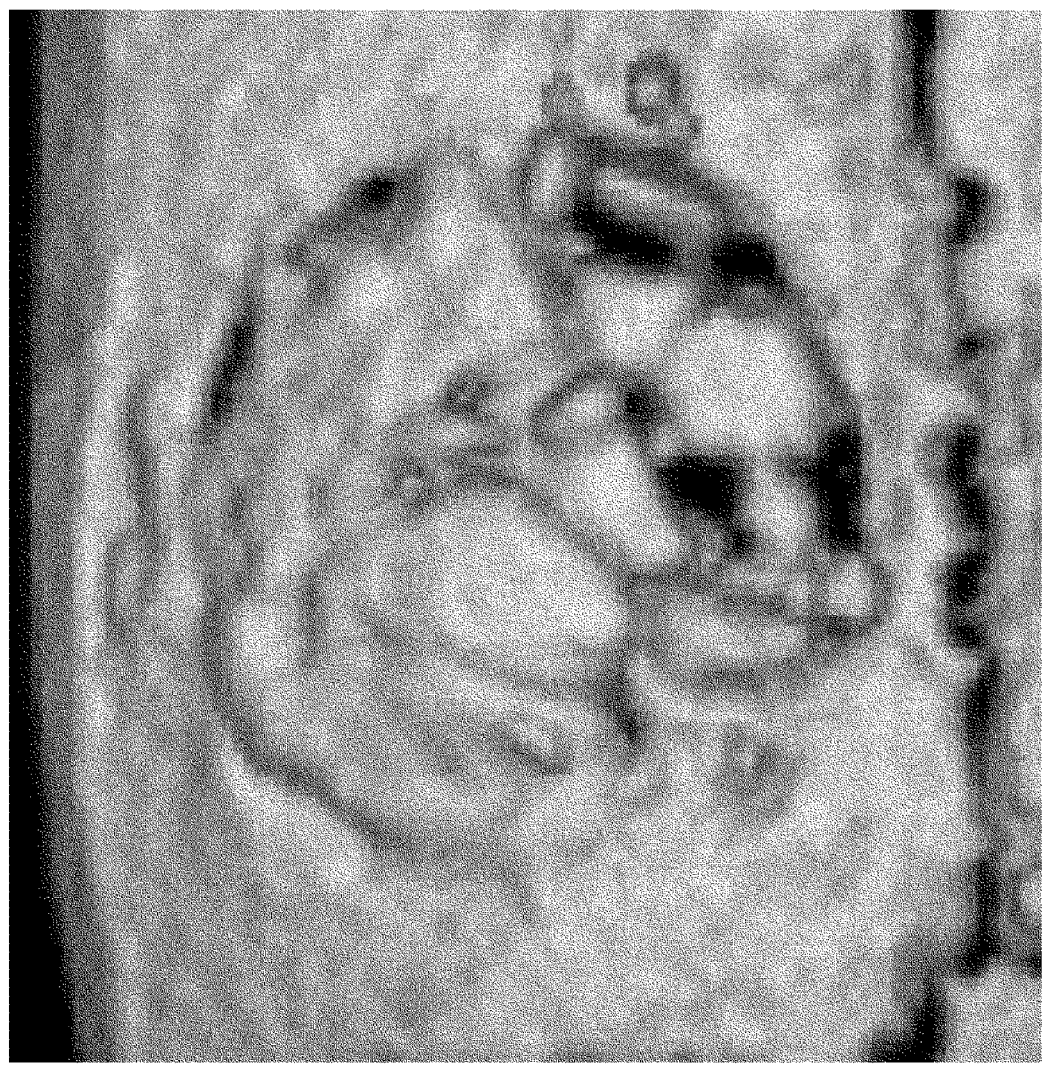
FIG. 9 is a photograph substituted for a drawing showing the state immediately after filling a hole formed in the skull of a mouse with biphasic SSCP.
Figure 10:
FIG. 10 is a photograph substituted for a drawing showing the state 3 weeks after filling a hole formed in the skull of a mouse with biphasic SSCP.
Figure 11:
FIG. 11 is a photograph substituted for a drawing showing the state 8 weeks after filling a hole formed in the skull of a mouse with biphasic SSCP.

These photographs substituted for drawings are shown in FIGS. 9 to 11, respectively.

Three different mice were evaluated for the bone coverage in 8 weeks after filling with the biphasic SSCP. The results are shown in Table 11.

Table 11 shows the ratio of the osteoconduction length formed in the hole relative to the bone defect width in the section of the hole as the bone coverage in percentage (%).

Table 12 shows how much bone covering proceeds when the hole is not filled with the biphasic SSCP, and shows the ratio of the osteoconduction length formed in the hole relative to the bone defect width in the section of the hole as the bone coverage in percentage (%).

TABLE 11

| Number OF Times | Bone Defect Width | Osteoconduction Length | Bone Coverage In Percentage % |
|---|---|---|---|
| | Relative Value | | |
| 1st Time | 314 | 256 | 81.5 |
| 2nd Time | 229 | 196 | 85.5 |
| 3rd Time | 226 | 107 | 47.3 |
| Average Value | | | 71.4 |

TABLE 12

| Number OF Times | Bone Defect Width | Osteoconduction Length | Bone Coverage In Percentage % |
|---|---|---|---|
| | Relative Value | | |
| 1st Time | 377 | 20 | 5.3 |

When the biphasic SSCP according to the present invention is used, osteoconductive bone formation is made in 70 percent or more toward the inner part of the hole from the surrounding existing bone forming the inner wall surface of the hole in 8 weeks after filling with the biphasic SSCP.

Next, in 8 weeks after filling, the skull of a mouse was sectioned, and the tissue including the section of the hole was stained by the TB (Toluidine Blue) staining method.

Figure 12:
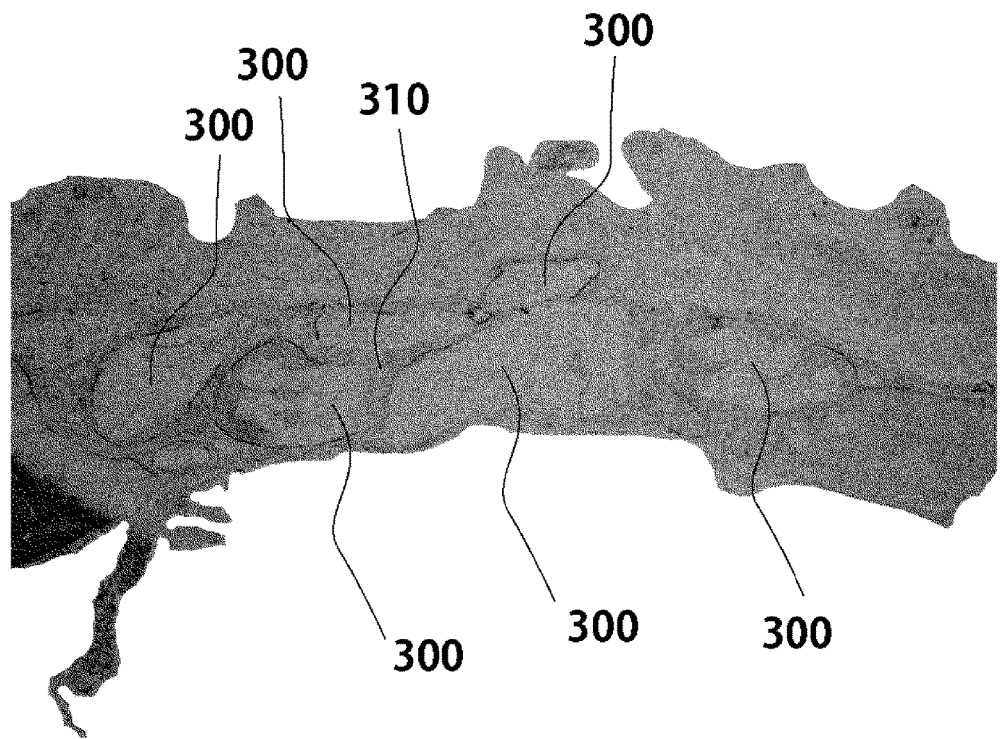
FIG. 12 is a photograph substituted for a drawing showing an enlarged section of tissue including a hole, which is stained by the TB staining method.

FIG. 12 is a photograph substituted for a drawing showing an enlarged section of tissue including a hole, which is stained by the TB staining method.

Similarly, the tissue including the section of the hole was stained by the HE (Hematoxylin and eosin) staining method.

Figure 13:
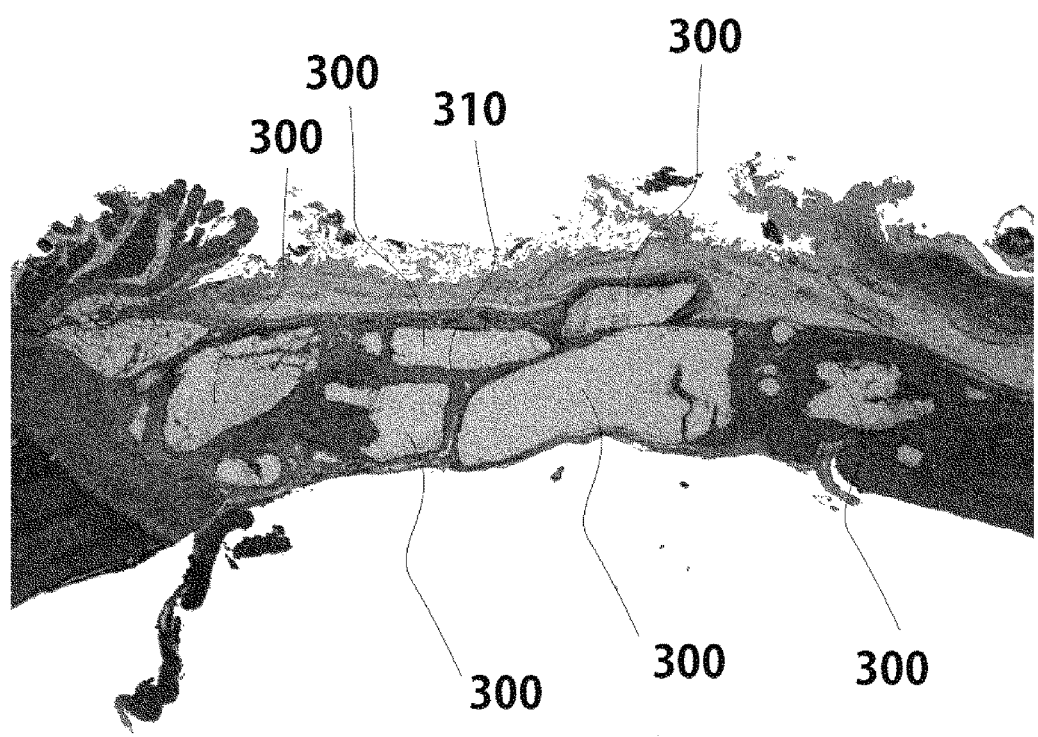
FIG. 13 is a photograph substituted for a drawing showing an enlarged section of tissue including a hole, which is stained by the HE staining method.

FIG. 13 is a photograph substituted for a drawing showing an enlarged section of tissue including a hole, which is stained by the HE staining method.

Reference numeral 300 and reference numeral 310 in FIG. 12 and FIG. 13 show a hole part and woven bone, respectively. Since the hole 300 has been subjected to deliming treatment with formic acid, it looks whiter than the surrounding tissue.

As seen from FIG. 12 and FIG. 13, it can be verified that the woven bone 310 is formed in the hole 300.

Example 18

Bone Formation by Biphasic SSCP Using Mouse

The experiment was performed in completely the same manner as in the case of Example 17 except that the mice were replaced with different individuals.

The hole formed in the skull of a mouse was photographed immediately after filling, 3 weeks after filling, and 8 weeks after filling.

Figure 14:
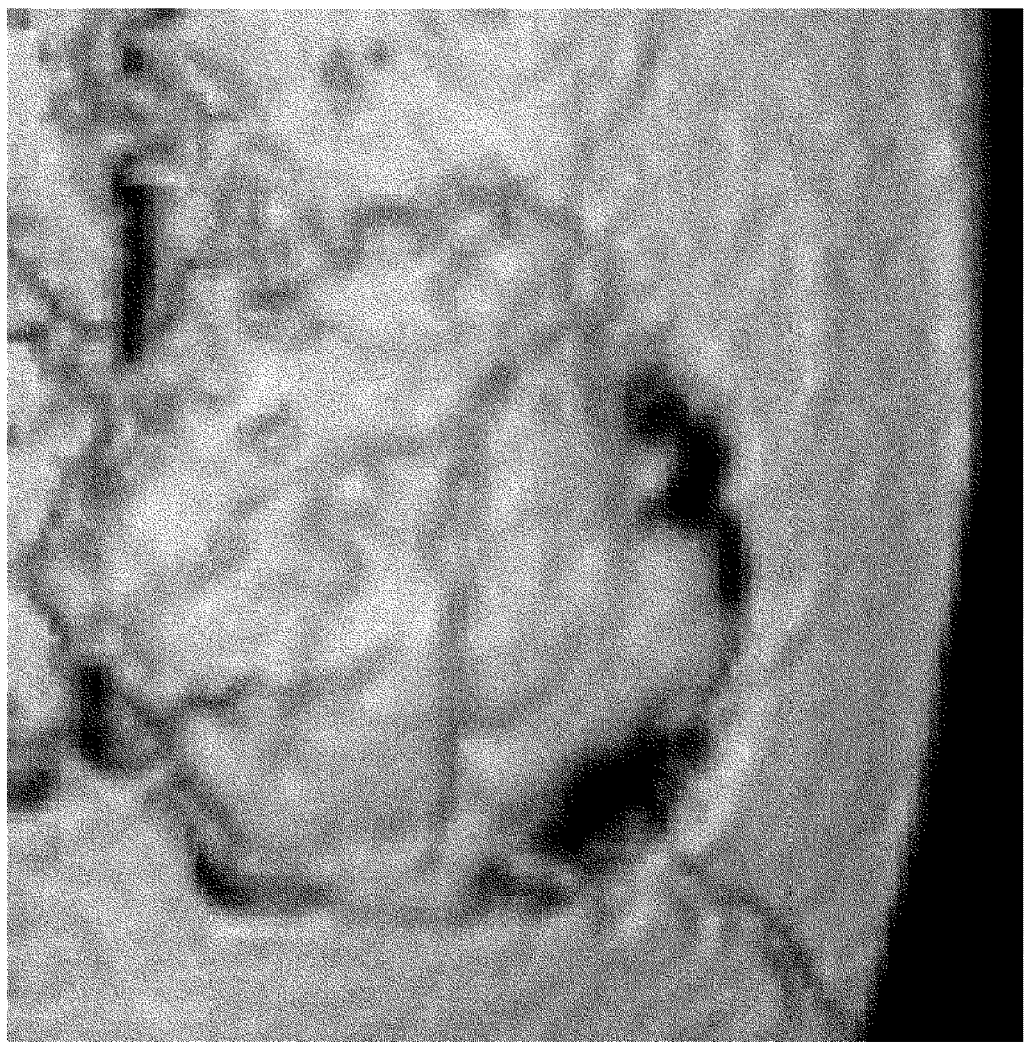
FIG. 14 is a photograph substituted for a drawing showing the state immediately after filling a hole formed in the skull of a mouse with biphasic SSCP.
Figure 15:
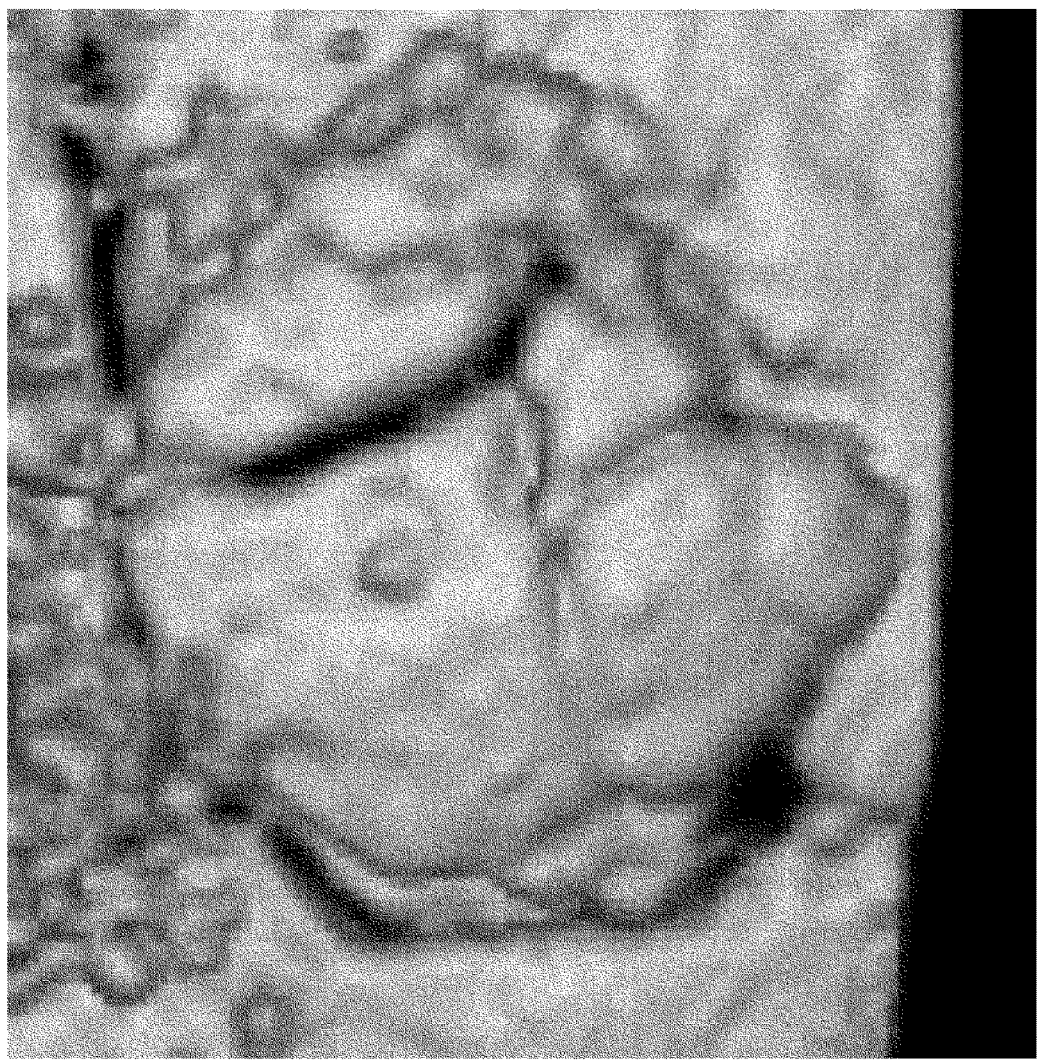
FIG. 15 is a photograph substituted for a drawing showing the state 3 weeks after filling a hole formed in the skull of a mouse with biphasic SSCP.
Figure 16:
FIG. 16 is a photograph substituted for a drawing showing the state 8 weeks after filling a hole formed in the skull of a mouse with biphasic SSCP.

These photographs substituted for drawings are shown in FIGS. 14 to 16, respectively.

Figure 17:
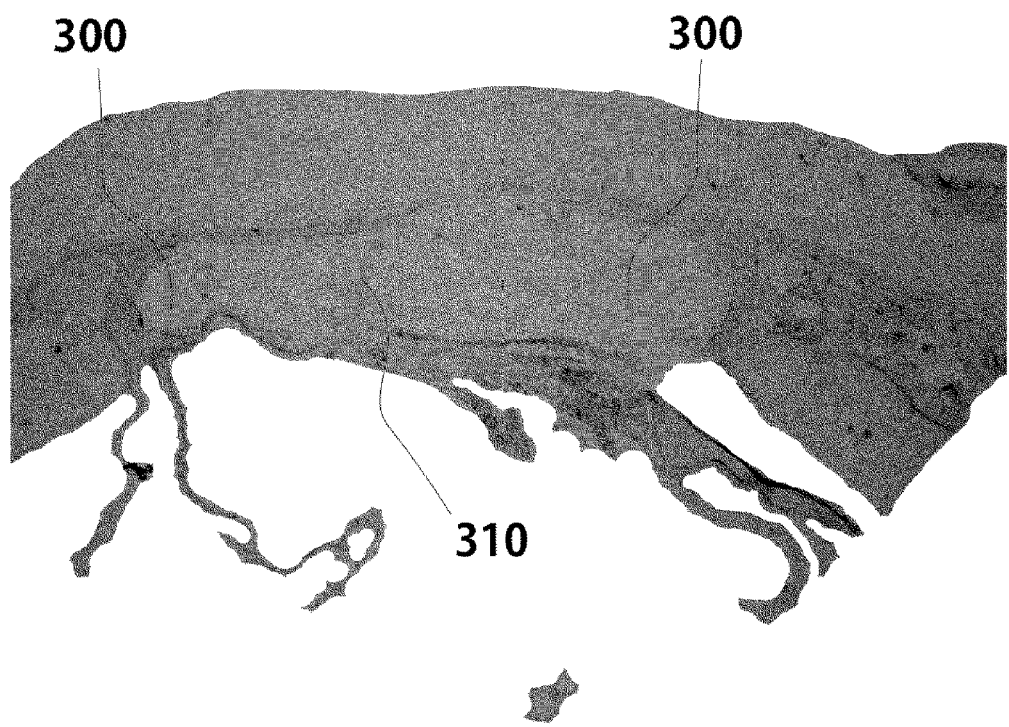
FIG. 17 is a photograph substituted for a drawing showing an enlarged section of tissue including a hole, which is stained by the TB staining method.

FIG. 17 is a photograph substituted for a drawing showing an enlarged section of tissue including a hole, which is stained by the TB staining method.

Figure 18:
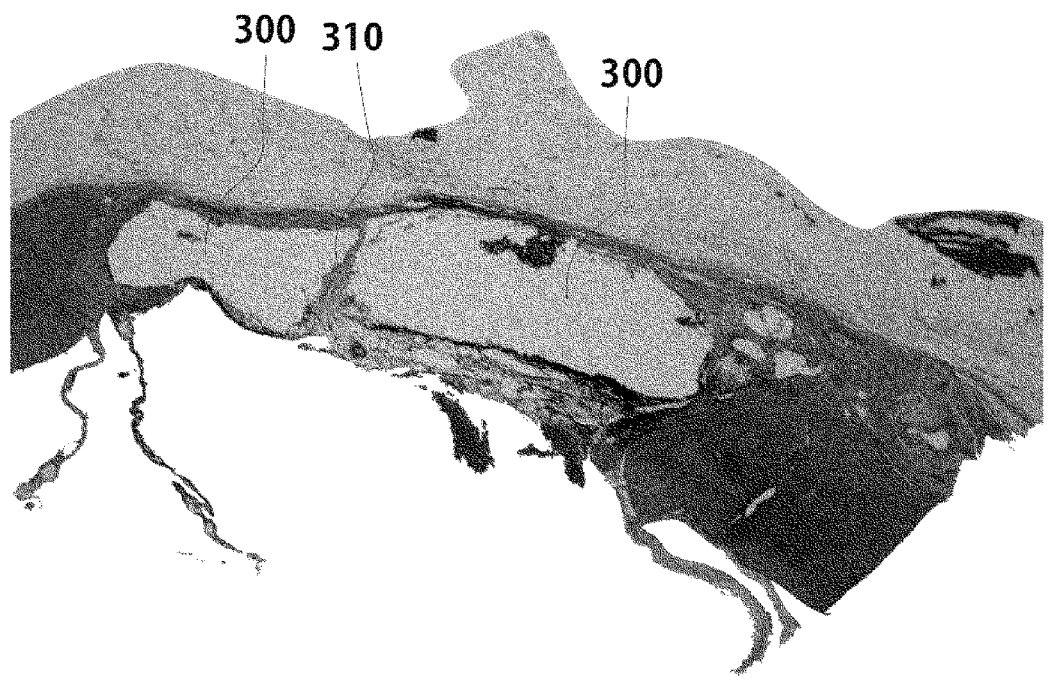
FIG. 18 is a photograph substituted for a drawing showing an enlarged section of tissue including a hole, which is stained by the HE staining method.

FIG. 18 is an enlarged photograph substituted for a drawing showing an enlarged section of tissue including a hole, which is stained by the HE staining method.

As seen from FIG. 17 and FIG. 18, it can be verified that the woven bone 310 is formed in the hole 300.

Example 19

Bone Formation by Biphasic SSCP Using Mouse

Instead of the biphasic SSCP powder portion used in the case of Example 17, was used a mixture of an α-TCP powder and a TTCP powder, in which the α-TCP powder and the TTCP powder were mixed so that the same molar ratio as that of the biphasic SSCP powder portion used in Example 16 was obtained.

Except the above, the experiment was performed in completely the same manner as in the case of Example 17.

The hole formed in the skull of a mouse was photographed immediately after filling, 3 weeks after filling, and 8 weeks after filling.

Figure 19:
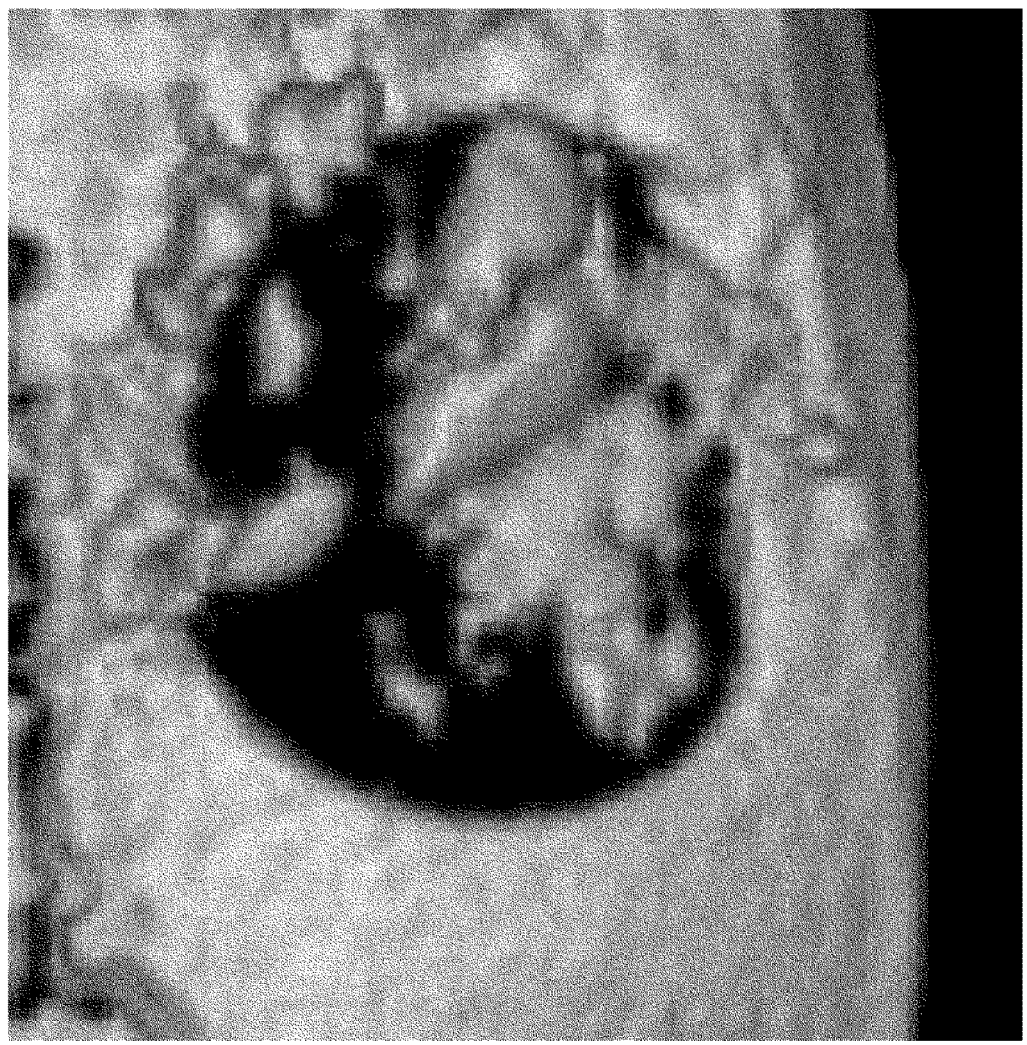
FIG. 19 is a photograph substituted for a drawing showing the state immediately after filling a hole formed in the skull of a mouse with biphasic SSCP.
Figure 20:
FIG. 20 is a photograph substituted for a drawing showing the state 3 weeks after filling a hole formed in the skull of a mouse with biphasic SSCP.
Figure 21:
FIG. 21 is a photograph substituted for a drawing showing the state 8 weeks after filling a hole formed in the skull of a mouse with biphasic SSCP.

These photographs substituted for drawings are shown in FIGS. 19 to 21, respectively.

Three different mice were evaluated for the degree of the bone formation in 8 weeks after filling with the biphasic SSCP. The results are shown in Table 13.

Table 13 shows the ratio of the osteoconduction length formed in the hole relative to the bone defect width in the section of the hole as the bone coverage in percentage (%).

TABLE 13

| Number OF Times | Bone Defect Width | Osteoconduction Length | Bone Coverage In Percentage % |
|---|---|---|---|
| | Relative Value | | |
| 1st Time | 200 | 120 | 60 |
| 2nd Time | 146 | 109 | 74.7 |
| 3rd Time | 204 | 150 | 73.5 |
| Average Value | | | 69.4 |

When the biphasic SSCP according to the present invention is used, osteoconductive bone formation is made in about 70 percent toward the inner part of the hole from the surrounding existing bone forming the inner wall surface of the hole in 8 weeks after filling with the biphasic SSCP.

Figure 22:
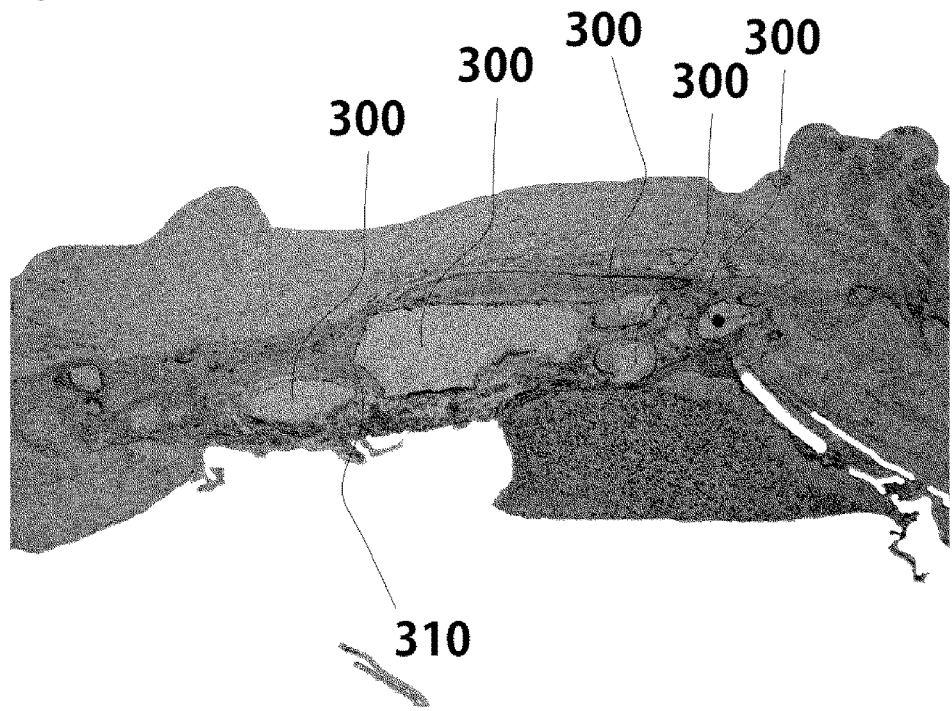
FIG. 22 is a photograph substituted for a drawing showing an enlarged section of tissue including a hole, which is stained by the TB staining method.

FIG. 22 is a photograph substituted for a drawing showing an enlarged section of tissue including a hole, which is stained by the TB staining method.

Figure 23:
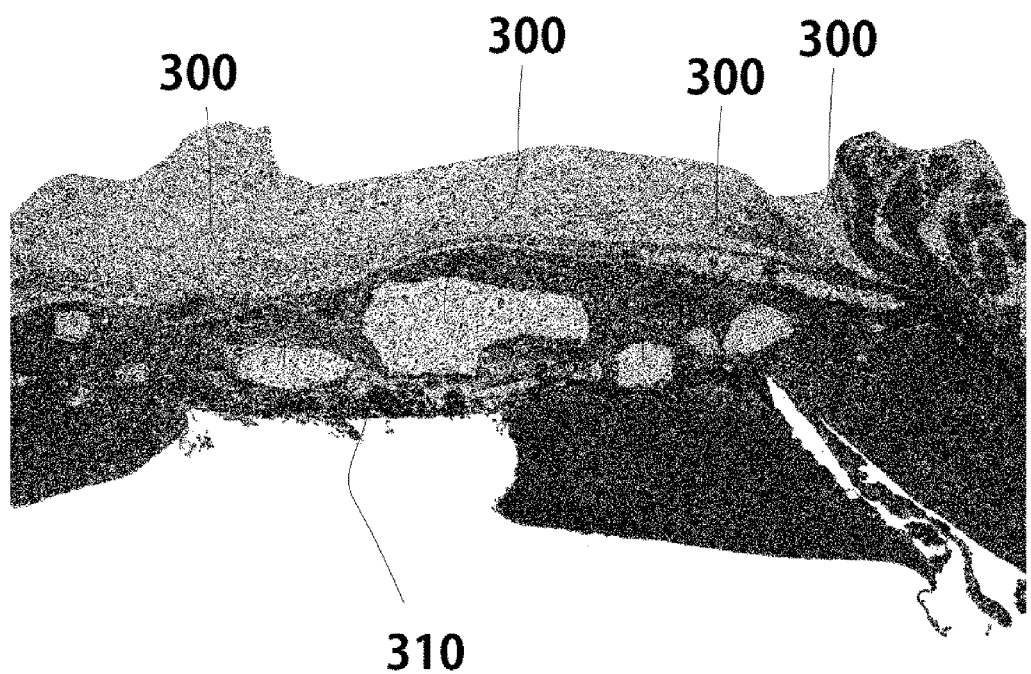
FIG. 23 is a photograph substituted for a drawing showing an enlarged section of tissue including a hole, which is stained by the HE staining method.

FIG. 23 is a photograph substituted for a drawing showing an enlarged section of tissue including a hole, which is stained by the HE staining method.

As seen from FIG. 22 and FIG. 23, it can be verified that the woven bone 310 is formed in the hole 300.

Example 20

Bone Formation by Biphasic SSCP Using Mouse

The experiment was performed in completely the same manner as in the case of Example 19 except that the mice were replaced with different individuals.

The hole formed in the skull of a mouse was photographed immediately after filling, 3 weeks after filling, and 8 weeks after filling.

Figure 24:
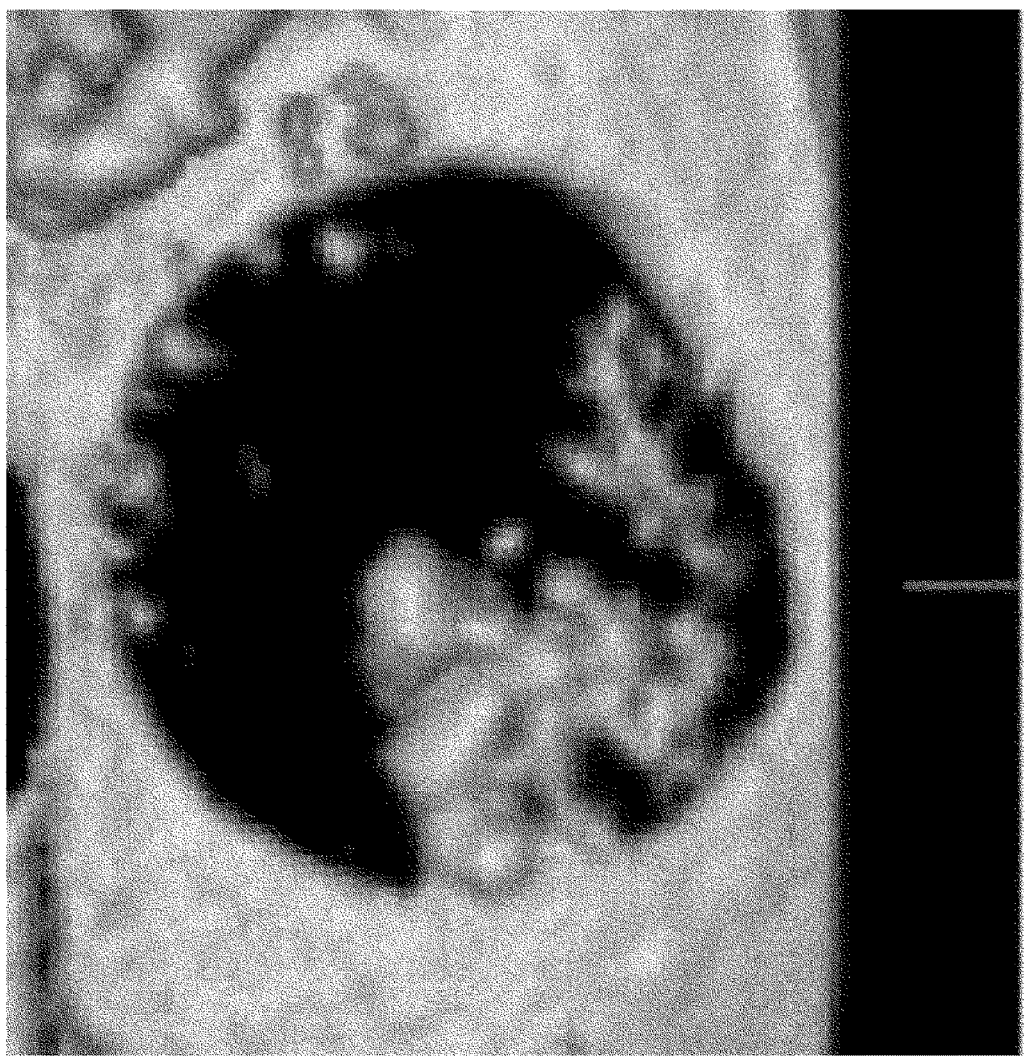
FIG. 24 is a photograph substituted for a drawing showing the state immediately after filling a hole formed in the skull of a mouse with biphasic SSCP.
Figure 25:
FIG. 25 is a photograph substituted for a drawing showing the state 3 weeks after filling a hole formed in the skull of a mouse with biphasic SSCP.
Figure 26:
FIG. 26 is a photograph substituted for a drawing showing the state 8 weeks after filling a hole formed in the skull of a mouse with biphasic SSCP.

These photographs substituted for drawings are shown in FIGS. 24 to 26, respectively.

Figure 27:
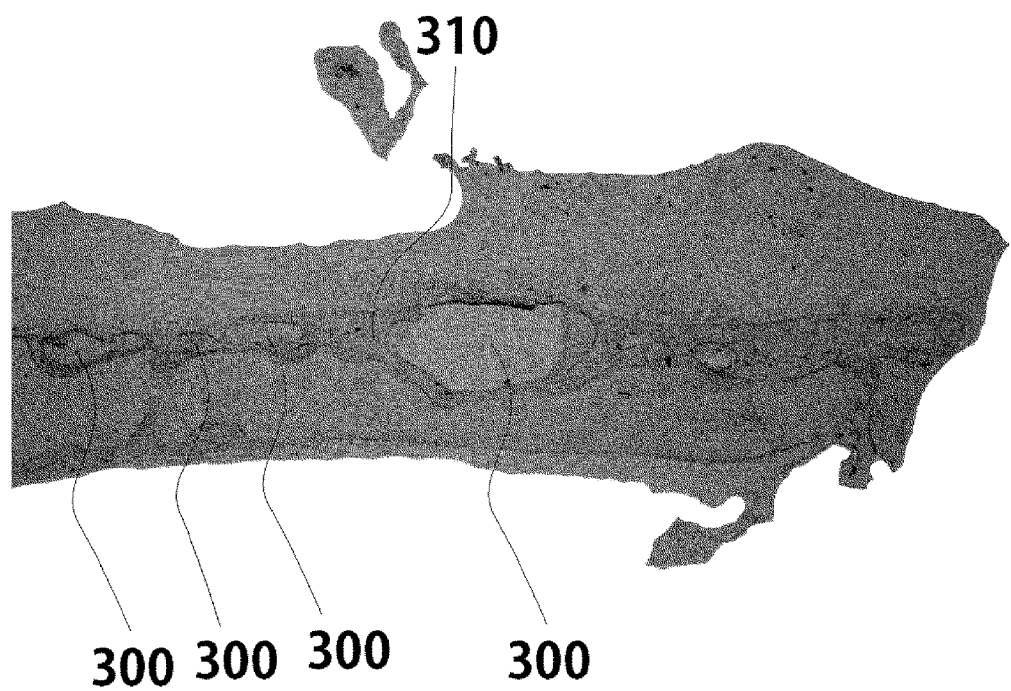
FIG. 27 is a photograph substituted for a drawing showing an enlarged section of tissue including a hole, which is stained by the TB staining method.

FIG. 27 is a photograph substituted for a drawing showing an enlarged section of tissue including a hole, which is stained by the TB staining method.

Figure 28:
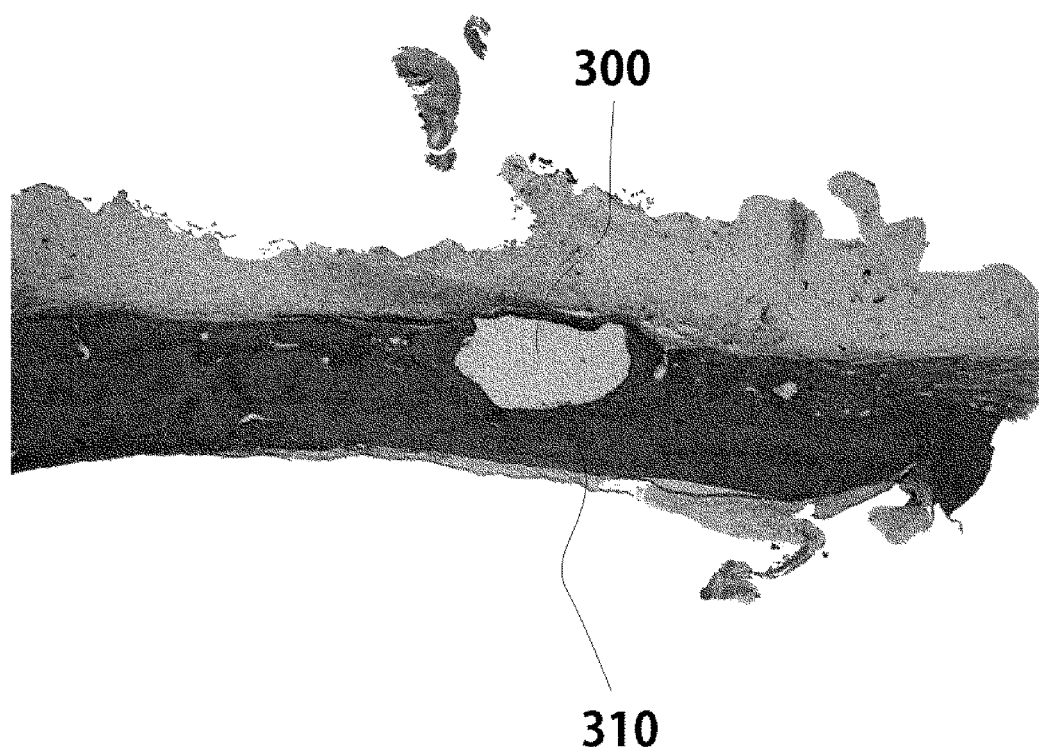
FIG. 28 is a photograph substituted for a drawing showing an enlarged section of tissue including a hole, which is stained by the HE staining method.

FIG. 28 is an enlarged photograph substituted for a drawing showing an enlarged section of tissue including a hole, which is stained by the HE staining method.

As seen from FIG. 27 and FIG. 28, it can be verified that the woven bone 310 is formed in the hole 300.

Comparative Example 17

Bone Formation by Biphasic SSCP Using Mouse

The experiment was performed in completely the same manner as in the case of Example 17 except that commercially available Biopex (registered trademark, available from Taisho Pharmaceutical Co., Ltd.) was used instead of the biphasic SSCP used in Example 17.

The hole formed in the skull of a mouse was photographed immediately after filling, 3 weeks after filling, and 8 weeks after filling.

Figure 29:
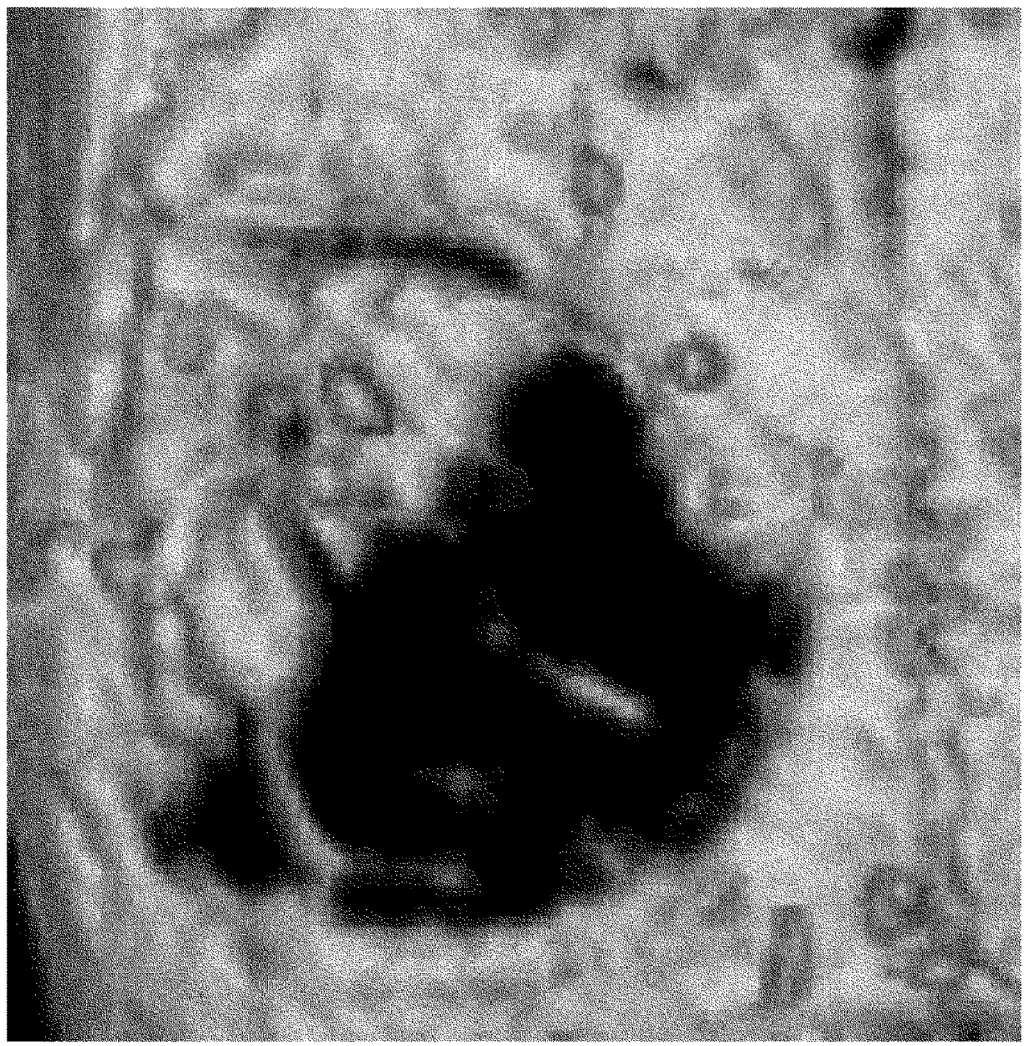
FIG. 29 is a photograph substituted for a drawing showing the state immediately after filling a hole formed in the skull of a mouse with commercially available material.
Figure 30:
FIG. 30 is a photograph substituted for a drawing showing the state 3 weeks after filling a hole formed in the skull of a mouse with commercially available material.
Figure 31:
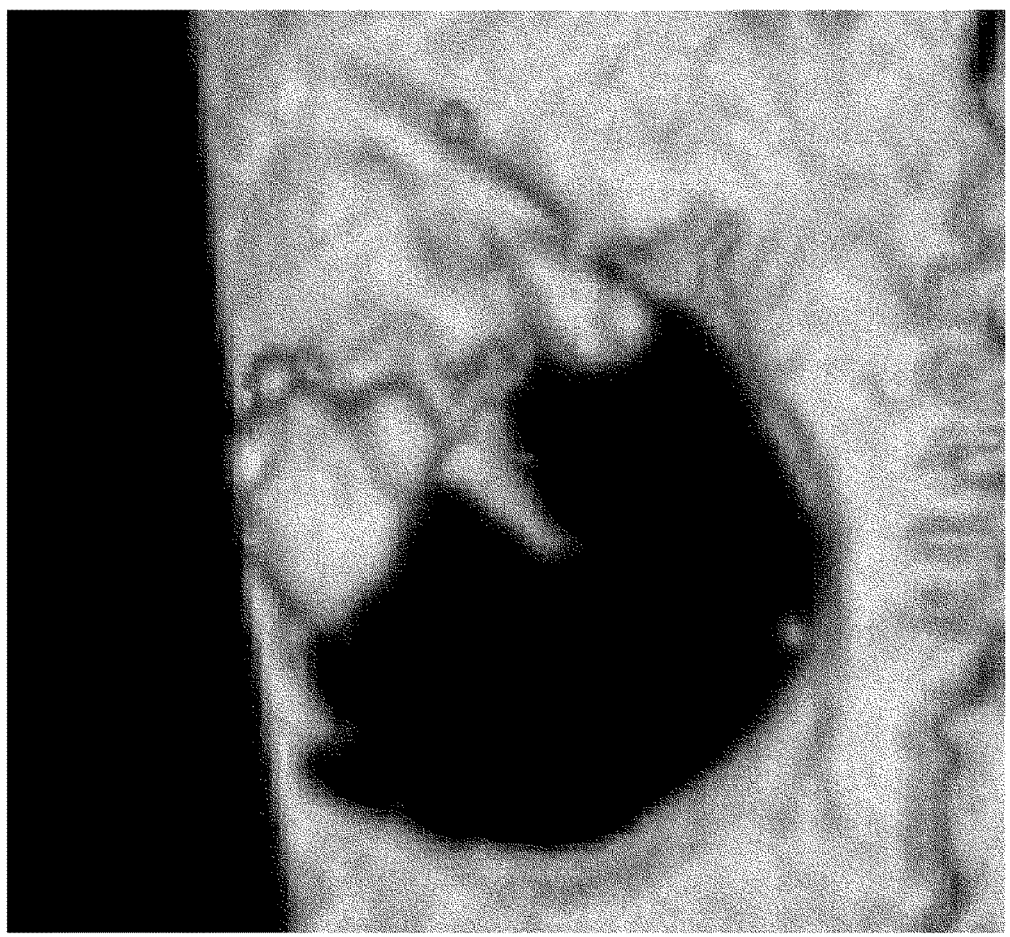
FIG. 31 is a photograph substituted for a drawing showing the state 8 weeks after filling a hole formed in the skull of a mouse with commercially available material.

These photographs substituted for drawings are shown in FIGS. 29 to 31, respectively.

Three different mice were evaluated for the degree of the bone formation in 8 weeks after filling with the biphasic SSCP. The results are shown in Table 14.

Table 14 shows the ratio of the osteoconduction length formed in the hole relative to the bone defect width in the section of the hole as the bone coverage in percentage (%).

TABLE 14

| Number OF Times | Bone Defect Width | Osteoconduction Length | Bone Coverage In Percentage % |
|---|---|---|---|
| | Relative Value | | |
| 1st Time | 292 | 45 | 15.4 |
| 2nd Time | 238 | 62 | 26 |
| 3rd Time | 200 | 110 | 55 |
| Average Value | | | 32.1 |

It was found that when the commercially available product was used, the bone formed in the hole in 8 weeks after filling with the biphasic SSCP was about 30 percent.

Figure 32:
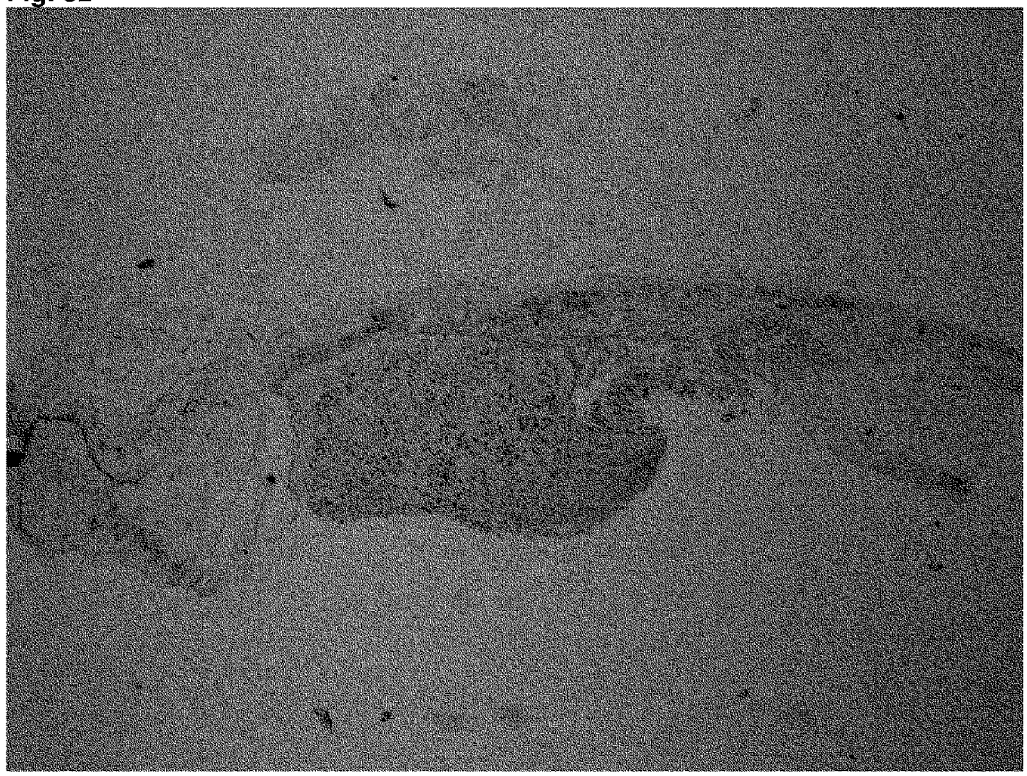
FIG. 32 is a photograph substituted for a drawing showing an enlarged section of tissue including a hole, which is stained by the TB staining method.

FIG. 32 is a photograph substituted for a drawing showing an enlarged section of tissue including a hole, which is stained by the TB staining method.

Figure 33:
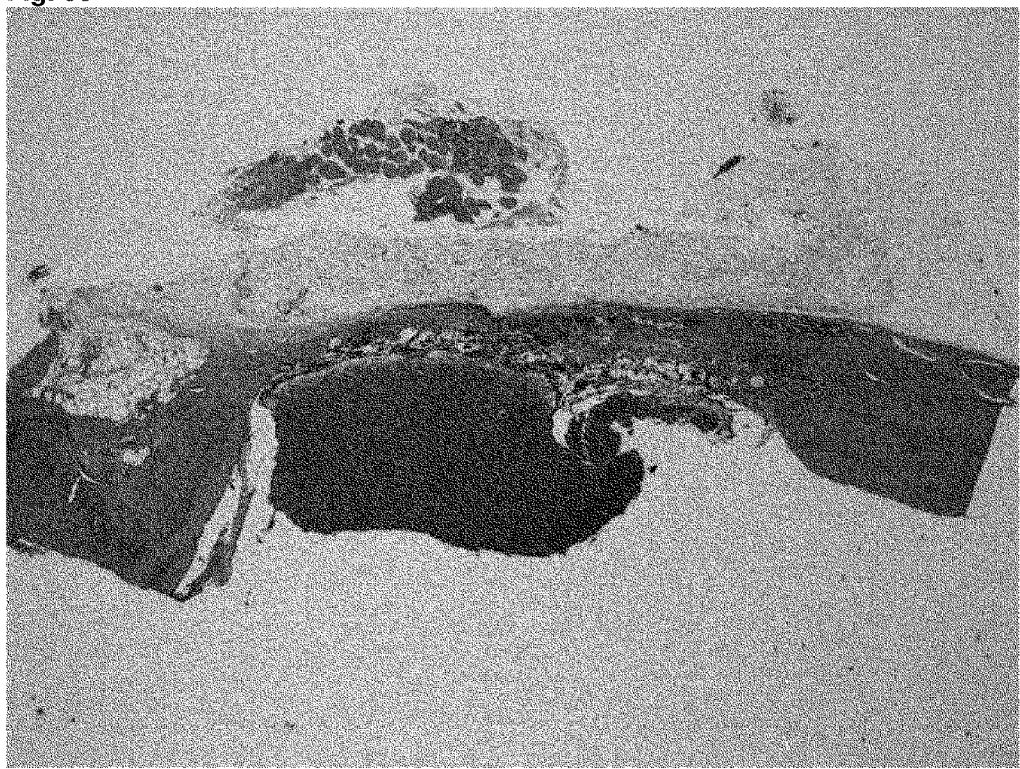
FIG. 33 is a photograph substituted for a drawing showing an enlarged section of tissue including a hole, which is stained by the HE staining method.

FIG. 33 is an enlarged photograph substituted for a drawing showing an enlarged section of tissue including a hole, which is stained by the HE staining method.

In the case where the commercially available product was used, definite formation of woven bone surrounding the hole was not able to be verified.

Comparative Example 18

Bone Formation by Biphasic SSCP Using Mouse

The experiment was performed in completely the same manner as in the case of Comparative Example 17 except that the mice were replaced with different individuals.

The hole formed in the skull of a mouse was photographed immediately after filling, 3 weeks after filling, and 8 weeks after filling.

Figure 34:
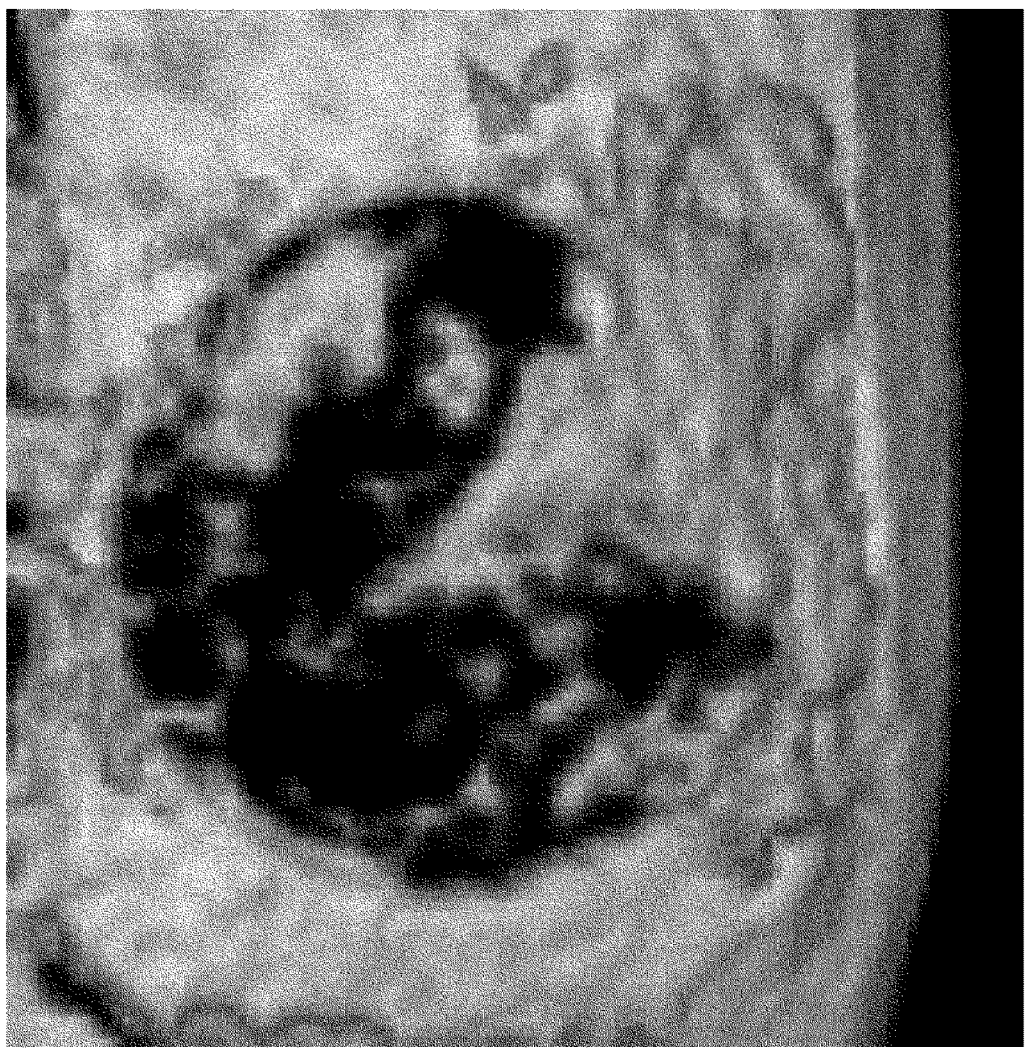
FIG. 34 is a photograph substituted for a drawing showing the state immediately after filling a hole formed in the skull of a mouse with commercially available material.
Figure 35:
FIG. 35 is a photograph substituted for a drawing showing the state 3 weeks after filling a hole formed in the skull of a mouse with commercially available material.
Figure 36:
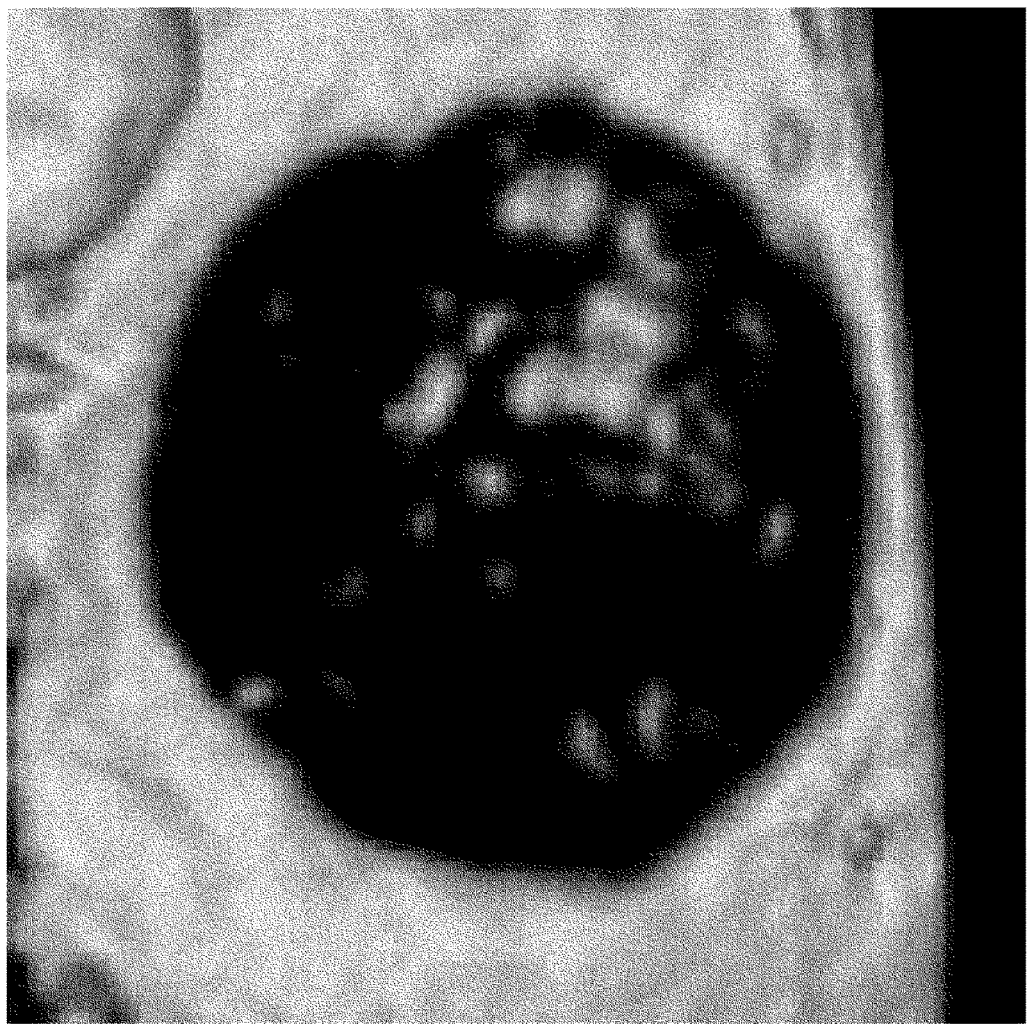
FIG. 36 is a photograph substituted for a drawing showing the state 8 weeks after filling a hole formed in the skull of a mouse with commercially available material.

These photographs substituted for drawings are shown in FIGS. 34 to 36, respectively.

Figure 37:
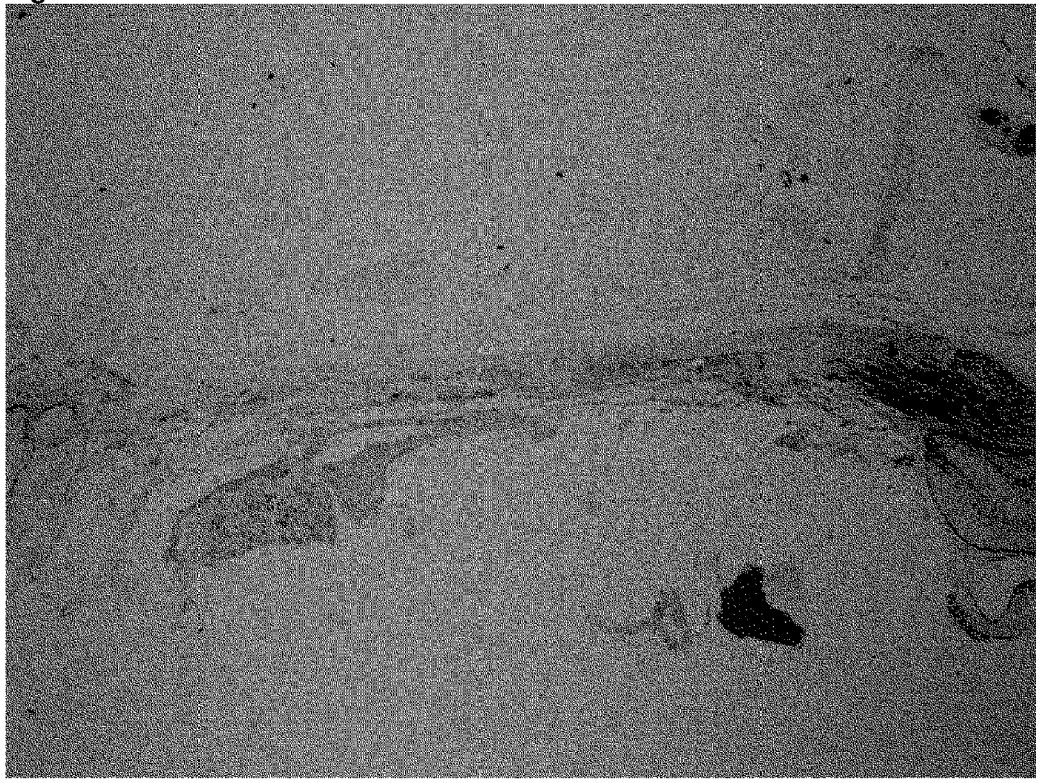
FIG. 37 is a photograph substituted for a drawing showing an enlarged section of tissue including a hole, which is stained by the TB staining method.

FIG. 37 is a photograph substituted for a drawing showing an enlarged section of tissue including a hole, which is stained by the TB staining method.

Figure 38:
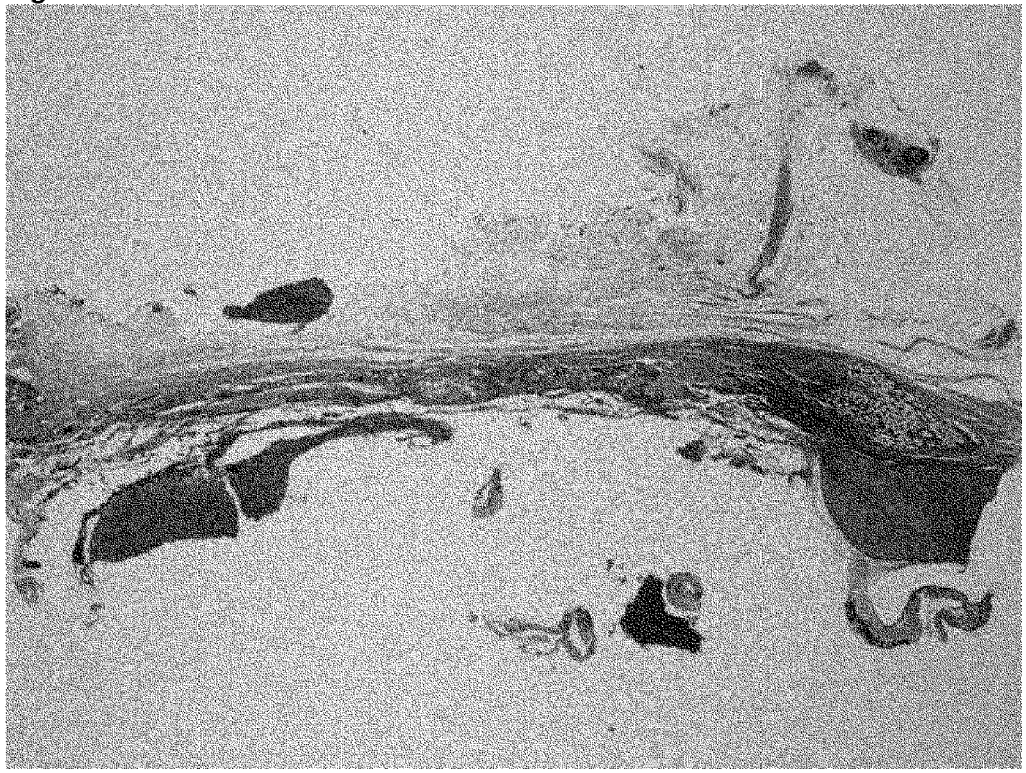
FIG. 38 is a photograph substituted for a drawing showing an enlarged section of tissue including a hole, which is stained by the HE staining method.

FIG. 38 is an enlarged photograph substituted for a drawing showing an enlarged section of tissue including a hole, which is stained by the HE staining method.

In the case where the commercially available product was used, definite formation of woven bone surrounding the hole was not able to be verified.

Comparative Example 19

Bone Formation by Biphasic SSCP Using Mouse

The experiment was performed in completely the same manner as in the case of Example 17 except that commercially available BoneSource (trade name, available from Stryker Corporation) was used instead of the biphasic SSCP used in Example 17.

The hole formed in the skull of a mouse was photographed immediately after filling, 3 weeks after filling, and 8 weeks after filling.

Figure 39:
FIG. 39 is a photograph substituted for a drawing showing the state immediately after filling a hole formed in the skull of a mouse with commercially available material.
Figure 40:
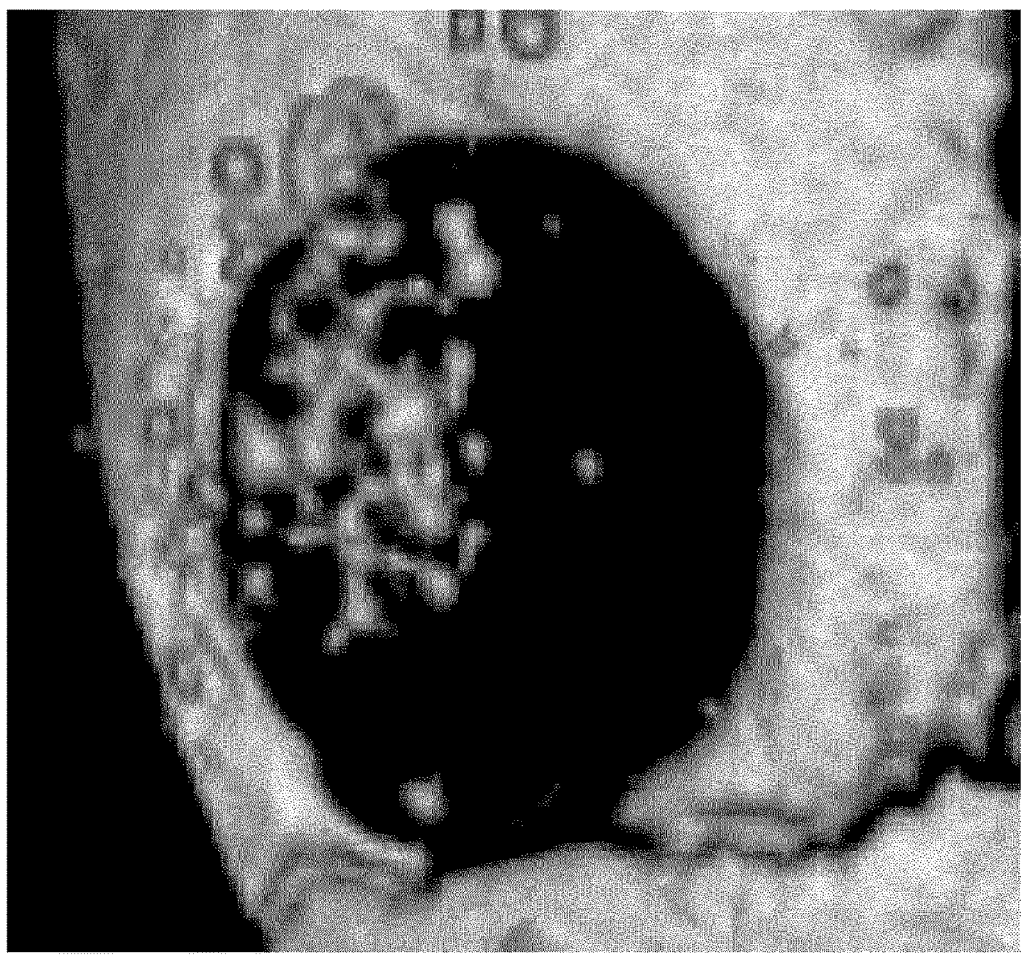
FIG. 40 is a photograph substituted for a drawing showing the state 3 weeks after filling a hole formed in the skull of a mouse with commercially available material.
Figure 41:
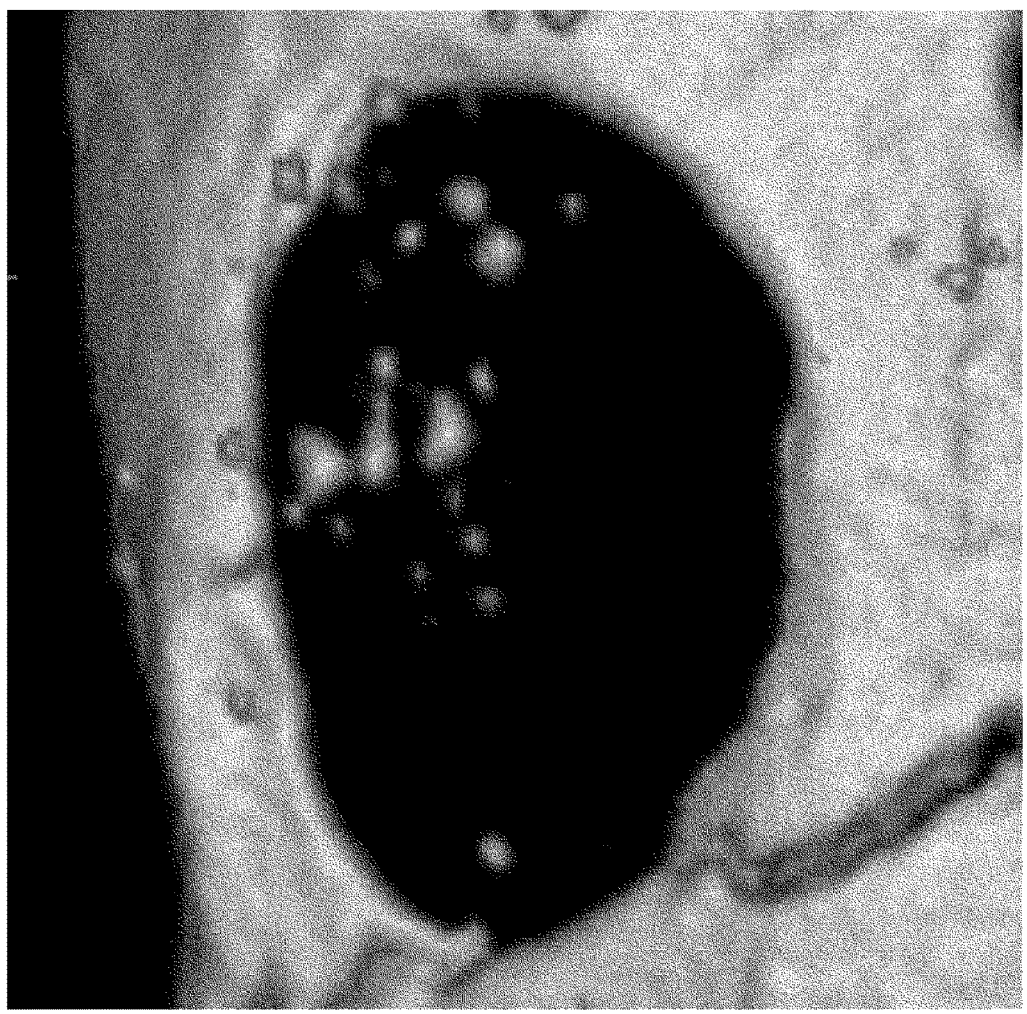
FIG. 41 is a photograph substituted for a drawing showing the state 8 weeks after filling a hole formed in the skull of a mouse with commercially available material.

These photographs substituted for drawings are shown in FIGS. 39 to 41, respectively.

Three different mice were evaluated for the degree of the bone formation in 8 weeks after filling with the biphasic SSCP. The results are shown in Table 15.

Table 15 shows the ratio of the osteoconduction length formed in the hole relative to the bone defect width in the section of the hole as the bone coverage in percentage (%).

TABLE 15

| Number OF Times | Bone Defect Width | Osteoconduction Length | Bone Coverage In Percentage % |
|---|---|---|---|
| | Relative Value | | |
| 1st Time | 158 | 55 | 34.8 |
| 2nd Time | 227 | 17 | 7.4 |
| 3rd Time | 126 | 67 | 53.1 |
| Average Value | | | 31.7 |

It was found that when the commercially available product was used, the bone formed in the hole in 8 weeks after filling with the biphasic SSCP was about 30 percent.

Figure 42:
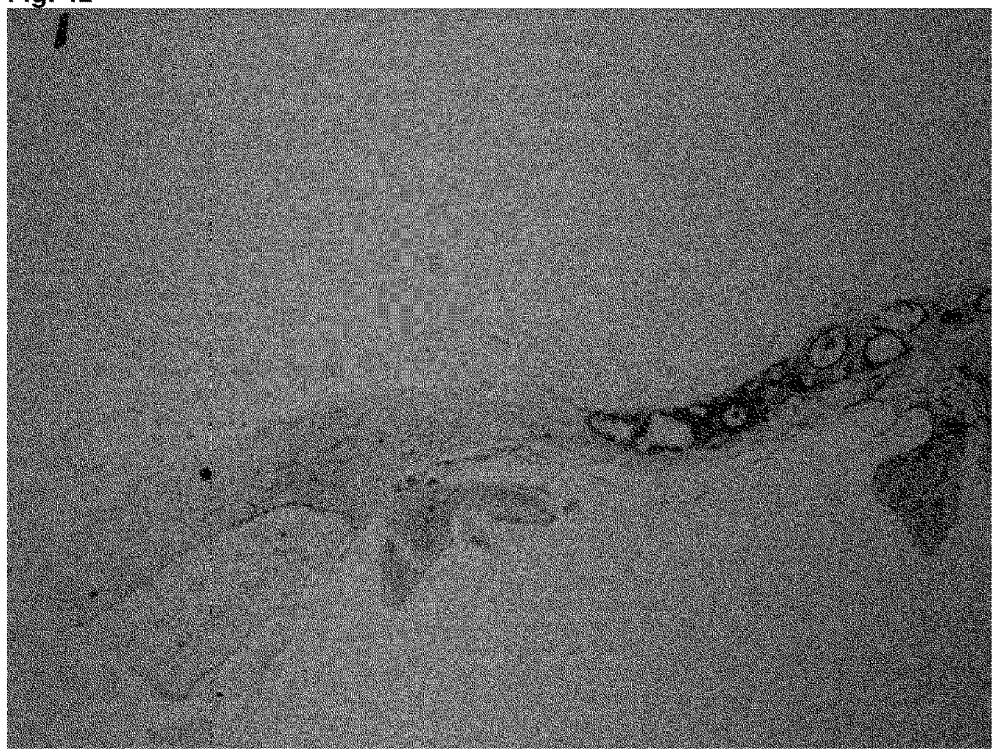
FIG. 42 is a photograph substituted for a drawing showing an enlarged section of tissue including a hole, which is stained by the TB staining method.

FIG. 42 is a photograph substituted for a drawing showing an enlarged section of tissue including a hole, which is stained by the TB staining method.

Figure 43:
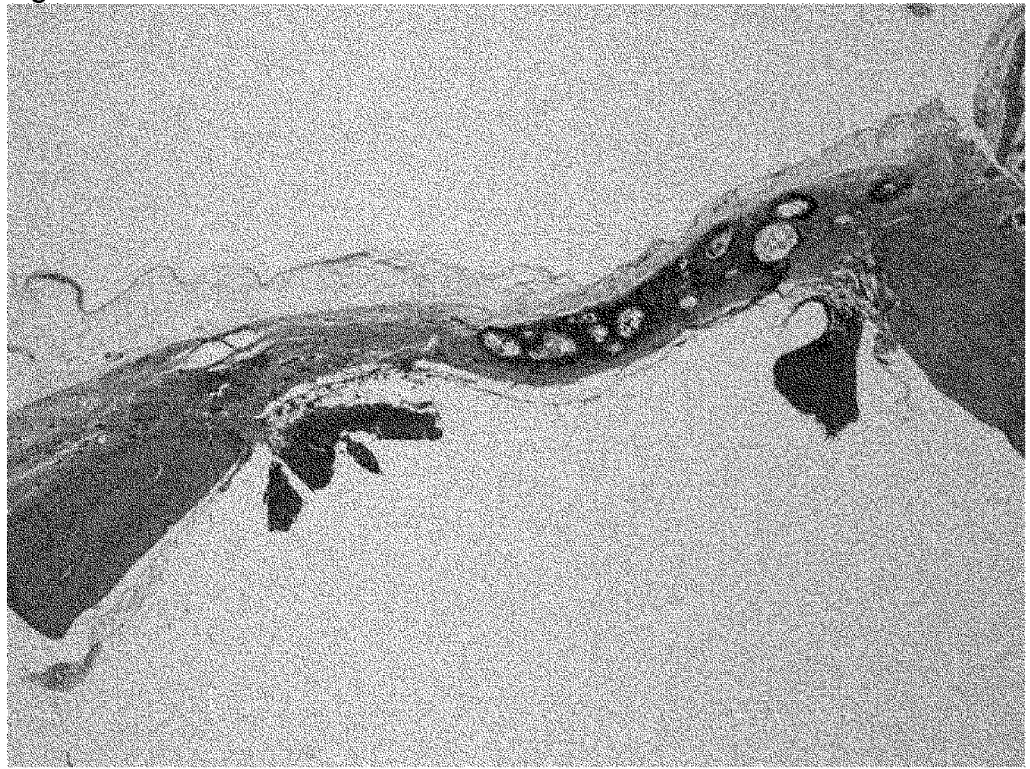
FIG. 43 is a photograph substituted for a drawing showing an enlarged section of tissue including a hole, which is stained by the HE staining method.

FIG. 43 is an enlarged photograph substituted for a drawing showing an enlarged section of tissue including a hole, which is stained by the HE staining method.

In the case where the commercially available product was used, definite formation of woven bone surrounding the hole was not able to be verified.

Comparative Example 20

Bone Formation by Biphasic SSCP Using Mouse

The experiment was performed in completely the same manner as in the case of Comparative Example 19 except that the mice were replaced with different individuals.

The hole formed in the skull of a mouse was photographed immediately after filling, 3 weeks after filling, and 8 weeks after filling.

Figure 44:
FIG. 44 is a photograph substituted for a drawing showing the state immediately after filling a hole formed in the skull of a mouse with commercially available material.
Figure 45:
FIG. 45 is a photograph substituted for a drawing showing the state 3 weeks after filling a hole formed in the skull of a mouse with commercially available material.
Figure 46:
FIG. 46 is a photograph substituted for a drawing showing the state 8 weeks after filling a hole formed in the skull of a mouse with commercially available material.

These photographs substituted for drawing are shown in FIGS. 44 to 46, respectively.

Figure 47:
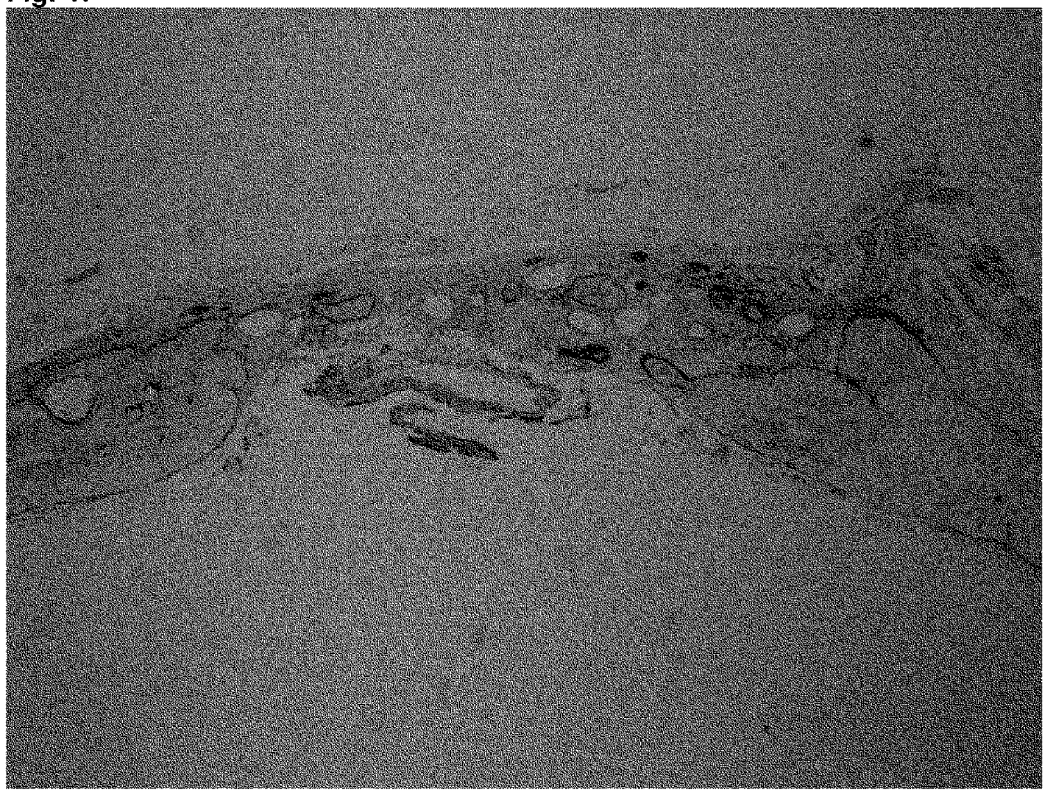
FIG. 47 is a photograph substituted for a drawing showing an enlarged section of tissue including a hole, which is stained by the TB staining method.

FIG. 47 is a photograph substituted for a drawing showing an enlarged section of tissue including a hole, which is stained by the TB staining method.

Figure 48:
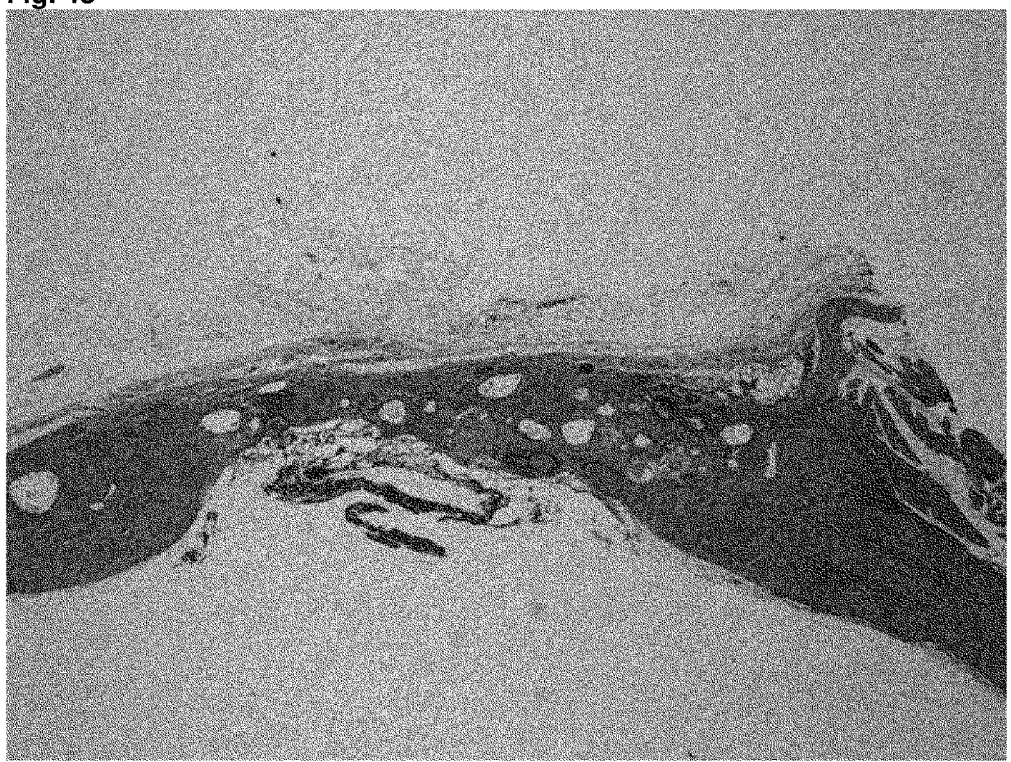
FIG. 48 is a photograph substituted for a drawing showing an enlarged section of tissue including a hole, which is stained by the HE staining method.

FIG. 48 is an enlarged photograph substituted for a drawing showing an enlarged section of tissue including a hole, which is stained by the HE staining method.

In the case where the commercially available product was used, definite formation of woven bone surrounding the hole was not able to be verified.

Example 21

Relationship Between Work Time and Set State of Biphasic SSCP

FIG. 55 to FIG. 59 are photographs substituted for drawings for describing the kneading state of a biphasic SSCP powder portion and a biphasic SSCP liquid portion.

The biphasic SSCP used in Example 21 is the same as that used in Example 13.

Figure 55:
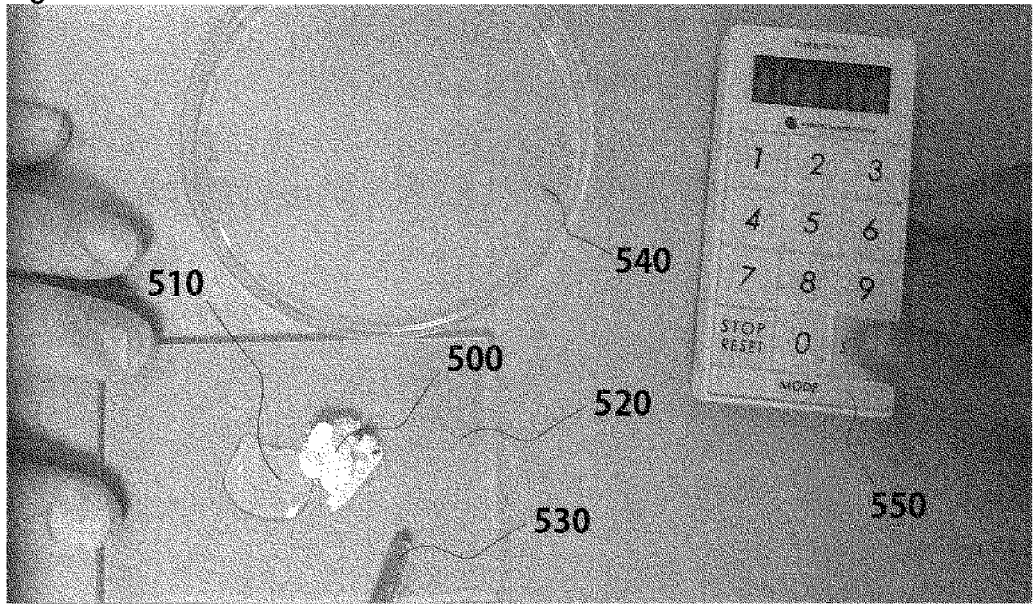
FIG. 55 is a photograph substituted for a drawing for describing the kneading state of a biphasic SSCP powder portion and a biphasic SSCP liquid portion.

As shown in FIG. 55, kneading of a biphasic SSCP powder portion 500 and a biphasic SSCP liquid portion 510 was started with a spatula 530 on a glass plate 520. The time of the start of kneading is 0 minutes and 0 seconds.

Figure 56:
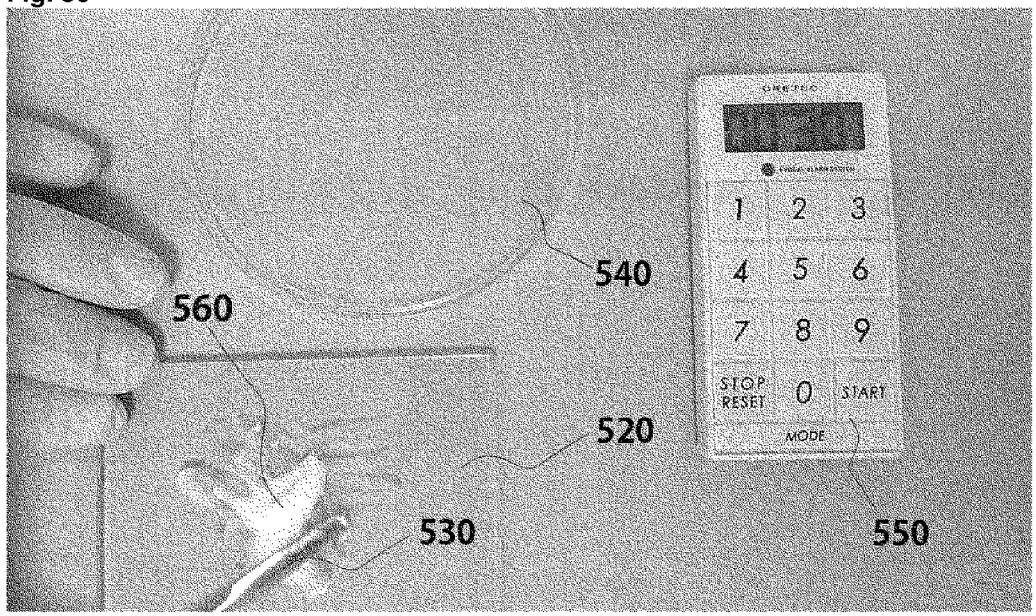
FIG. 56 is a photograph substituted for a drawing for describing the kneading state of a biphasic SSCP powder portion and a biphasic SSCP liquid portion.

Next, as shown in FIG. 56, the biphasic SSCP powder portion 500 and the biphasic SSCP liquid portion 510 were kneaded for 30 seconds to obtain a uniform kneaded material 560.

Figure 57:
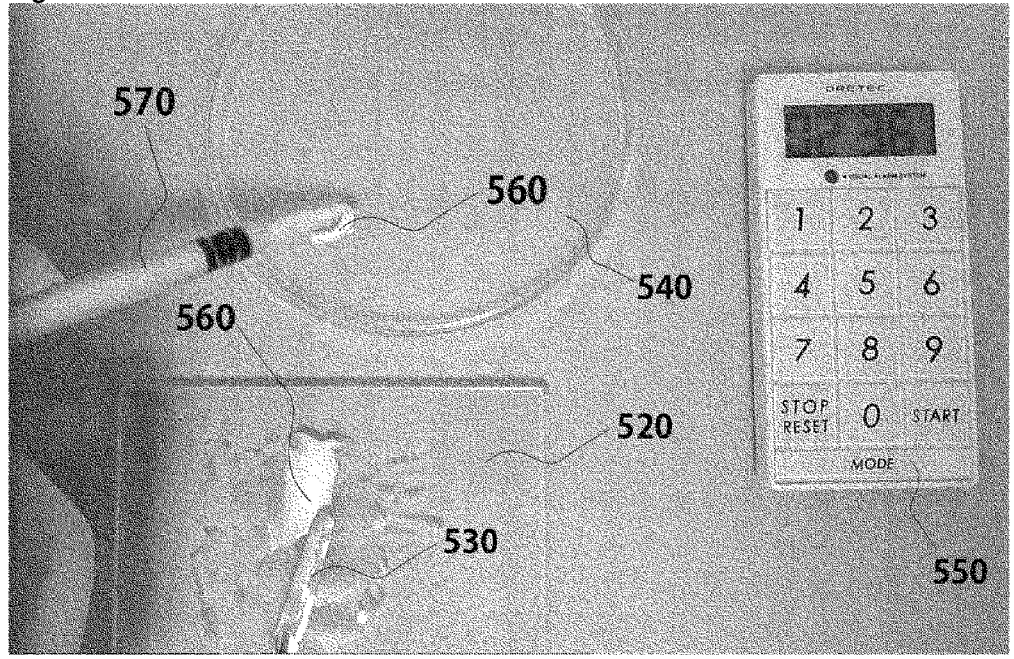
FIG. 57 is a photograph substituted for a drawing for describing the kneading state of a biphasic SSCP powder portion and a biphasic SSCP liquid portion.

Next, as shown in FIG. 57, the kneaded material 560 was injectable with a syringe 570 at the time when 2 minutes and 36 seconds elapsed from the start of kneading.

The kneaded material 560 was injected from the syringe 570 into a dish 540 in which distilled water was put.

Figure 58:
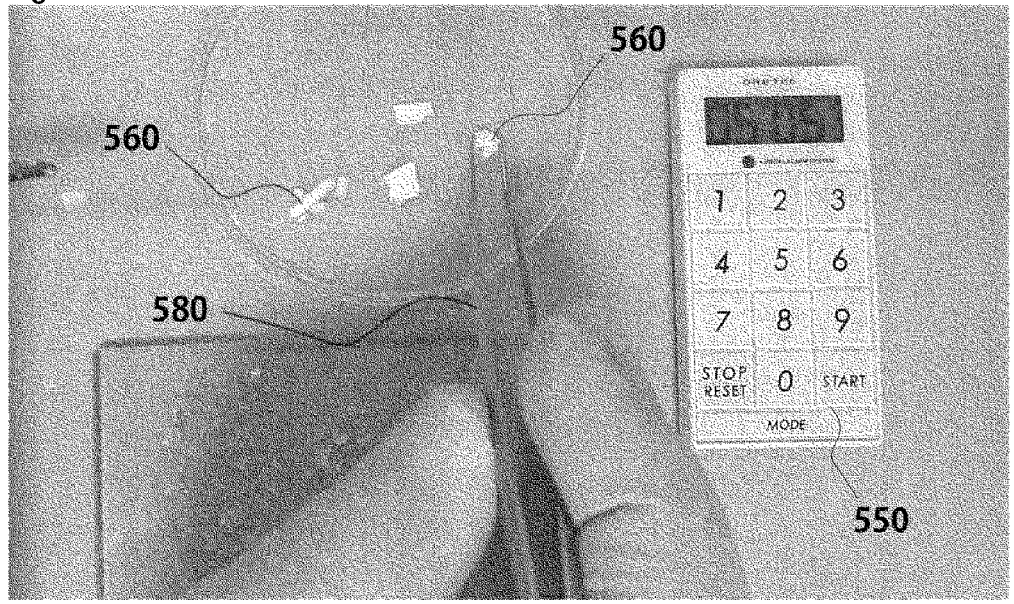
FIG. 58 is a photograph substituted for a drawing for describing the kneading state of a biphasic SSCP powder portion and a biphasic SSCP liquid portion.

Next, as shown in FIG. 58, the kneaded material 560 was deformed by applying external force and shapable at the time when 5 minutes and 05 seconds elapsed from the start of kneading.

Figure 59:
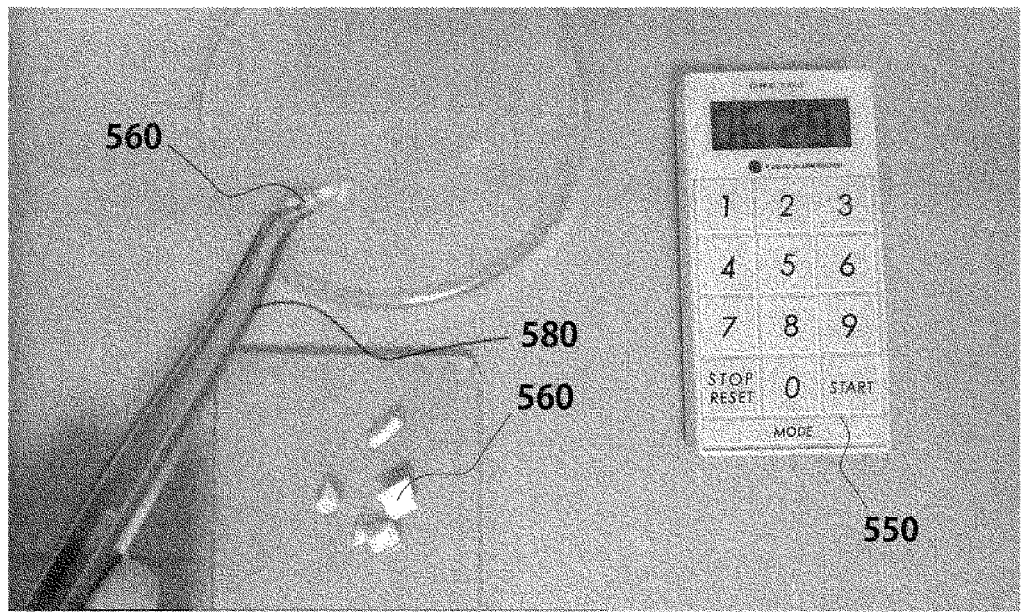
FIG. 59 is a photograph substituted for a drawing for describing the kneading state of a biphasic SSCP powder portion and a biphasic SSCP liquid portion.

Next, as shown in FIG. 59, the kneaded material 560 set at the time when 6 minutes and 29 seconds elapsed from the start of kneading, and the set material was able to be removed from distilled water in the dish 540.

Comparative Example 21

The experiment was performed in completely the same manner as in the case of Example 21 except that commercially available Biopex (registered trademark, available from Taisho Pharmaceutical Co., Ltd.) was used instead of the biphasic SSCP used in Example 21.

Figure 60:
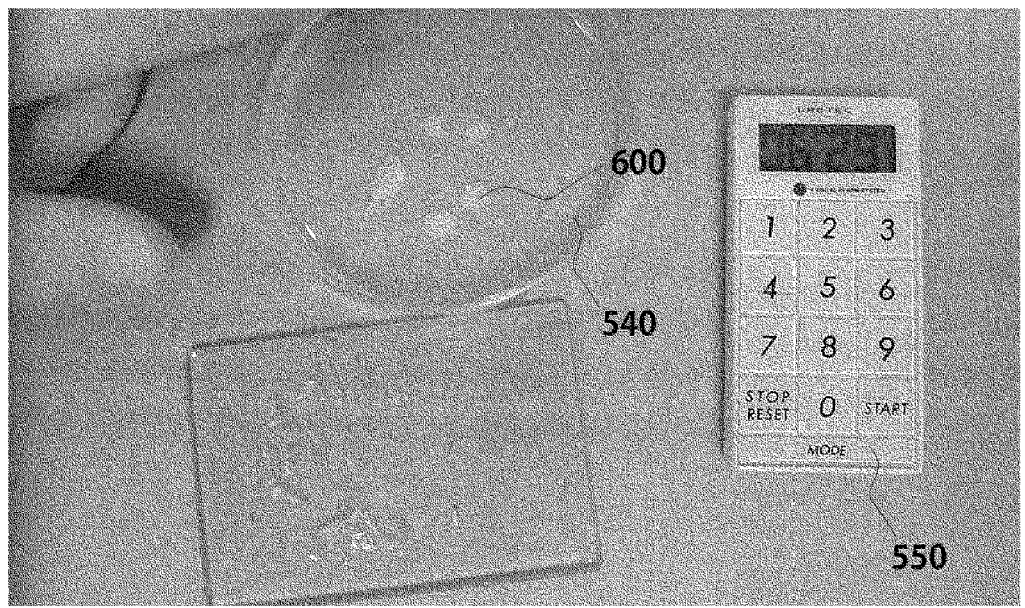
FIG. 60 is a photograph substituted for a drawing for describing the set state of a commercially available product.

FIG. 60 is a photograph substituted for a drawing for describing the set state of the commercially available product.

As shown in FIG. 60, the kneaded material 600 did not set at the time when 6 minutes and 29 seconds elapsed from the start of kneading, and a set material was not able to be removed from distilled water in the dish 540.

Comparative Example 22

The experiment was performed in completely the same manner as in the case of Example 21 except that commercially available BoneSource (trade name, available from Stryker Corporation) was used instead of the biphasic SSCP used in Example 21.

Figure 61:
FIG. 61 is a photograph substituted for a drawing for describing the set state of a commercially available product.

FIG. 61 is a photograph substituted for a drawing for describing the set state of the commercially available product.

As shown in FIG. 61, the kneaded material 610 did not set at the time when 6 minutes and 29 seconds elapsed from the start of kneading, and a set material was not able to be removed from distilled water in the dish 540.

Example 22

Physical Properties Test of Biphasic SSCP

The biphasic SSCP liquid portion used in Example 14 was diluted by adding 3.5 g of distilled water to 1.0 g of the biphasic SSCP liquid portion. The resulting sample was used to measure the DTS of the set material by the same measuring method as in Example 11. The results are shown in Table 16.

Example 23

Physical Properties Test of Biphasic SSCP

The biphasic SSCP liquid portion used in Example 15 was diluted by adding 4.0 g of distilled water to 1.0 g of the biphasic SSCP liquid portion. The resulting sample was used to measure the DTS of the set material by the same measuring method as in Example 11. The results are shown in Table 17.

TABLE 16

|  | Diameter (mm) | Thickness (mm) | Load (N) | MPa |
|---|---|---|---|---|
| 1st Time | 6.08 | 3.17 | 108.70 | 3.59 |
| 2nd Time | 6.09 | 3.11 | 106.20 | 3.57 |
| 3rd Time | 6.07 | 3.09 | 89.00 | 3.02 |
| 4th Time | 6.09 | 3.11 | 104.50 | 3.51 |
| 5th Time | 6.09 | 3.18 | 131.50 | 4.32 |
| Average | 6.08 | 3.13 | 107.98 | 3.61 |
| Standard Deviation | 0.01 | 0.04 | 15.24 | 0.47 |

TABLE 17

|  | Diameter (mm) | Thickness (mm) | Load (N) | MPa |
|---|---|---|---|---|
| 1st Time | 6.05 | 3.24 | 122.00 | 3.96 |
| 2nd Time | 6.06 | 3.07 | 88.50 | 3.03 |
| 3rd Time | 6.01 | 3.07 | 91.00 | 3.14 |
| 4th Time | 6.03 | 3.09 | 99.00 | 3.38 |
| 5th Time | 6.06 | 3.13 | 100.50 | 3.37 |
| Average | 6.04 | 3.12 | 100.20 | 3.38 |
| Standard Deviation | 0.02 | 0.07 | 13.21 | 0.36 |

Comparative Example 23

In quite the same manner as in the case of Comparative Example 15, a 1 mol/L citric acid aqueous solution was used instead of the biphasic SSCP liquid portion used in Example 1. The resulting sample was used.

The electron microscope photograph of the set material of the biphasic SSCP was taken under the same conditions as in the case of Example 11.

Figure 62:
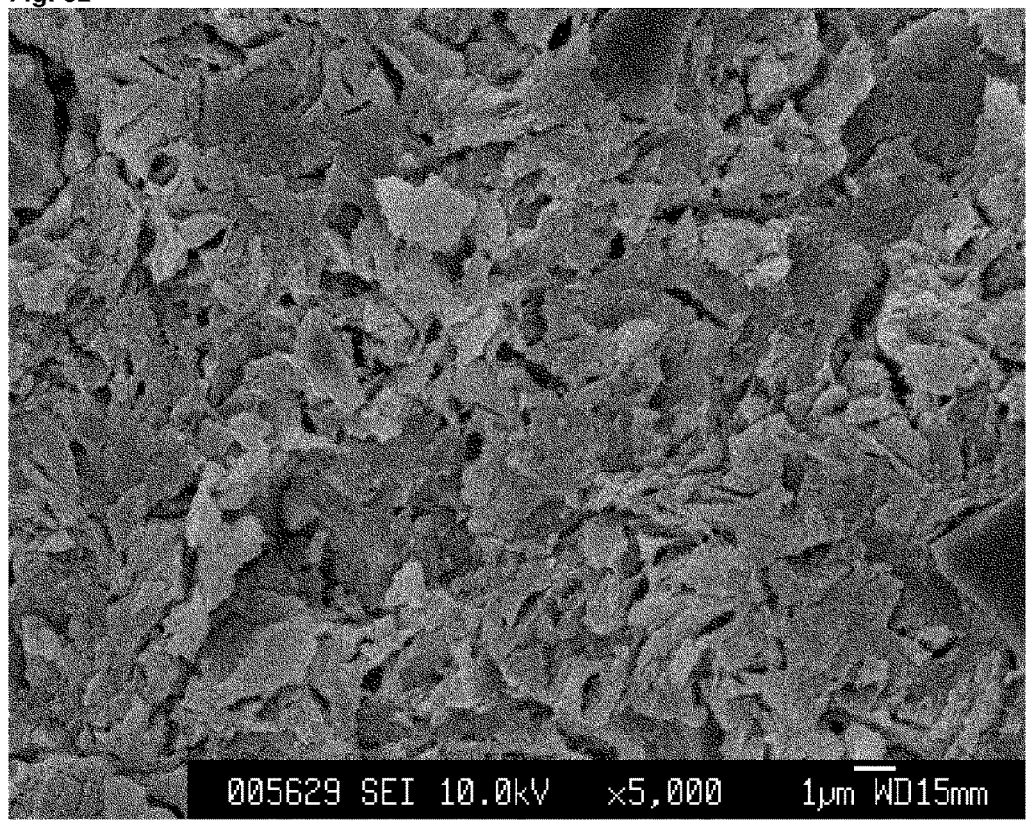
FIG. 62 is a photograph substituted for a drawing showing the surface of a set material, in which citric acid is used, enlarged by 5000 times with an electron microscope.

FIG. 62 is a photograph substituted for a drawing showing the surface of a set material in which citric acid is used, enlarged by 5000 times with an electron microscope.

As shown in FIG. 62, the state of precipitation of HA crystals cannot be observed when citric acid is used.

INDUSTRIAL APPLICABILITY

According to the present invention, since the work time of biphasic SSCP can be adjusted in a range of 10 seconds to 600 seconds, the biphasic SSCP can be effectively applied to the application for the treatment of a patient who has not been able to undergo sufficient treatment due to the difficulty of bone formation; a hard tissue regeneration material can be supplied to a medical institution quickly and in large quantities; and, in addition, a dental material used for the applications for hypersensitivity, the prevention of dental caries, and the like can be supplied stably and in large quantities.

REFERENCE SIGNS LIST

1 Biphasic SSCP liquid portion used in Example 1
3 Biphasic SSCP liquid portion used in Example 3
4 Biphasic SSCP liquid portion used in Example 4
5 Biphasic SSCP liquid portion used in Example 5
6 Biphasic SSCP liquid portion used in Example 6
7 Biphasic SSCP liquid portion used in Example 7
8 Biphasic SSCP liquid portion used in Example 8
9 Biphasic SSCP liquid portion used in Example 9
13 Biphasic SSCP liquid portion used in Example 13
14 Biphasic SSCP liquid portion used in Example 14
15 Biphasic SSCP liquid portion used in Example 15
100 HA
110 TTCP
120 α-TCP
200 Gilmore needle
210 Tip of Gilmore needle
220 Rear end of Gilmore needle
230 Body of Gilmore needle
300 Hole of skull of mouse
310 Woven bone
400 Mouse
410 Skull of mouse
420 Operative wound
430 Forceps
440 Hook
450,560 Kneaded material of biphasic SSCP
500 Biphasic SSCP powder portion
510 Biphasic SSCP liquid portion
530 Spatula
540 Dish
550 Stopwatch
570 Syringe
600,610 Kneaded material using commercially available product
a The point of (x, y)=(2.96, 1.09)
b The point of (x, y)=(0.592, 0.218)
c The point of (x, y)=(7.38, 0.25)

The invention claimed is:

1. A method for controlling work time for shape-forming a biphasic self-setting calcium phosphate comprising,
adjusting a work time to be in a range of 10 seconds to 600 seconds by kneading a biphasic self-setting calcium phosphate powder portion and a biphasic self-setting calcium phosphate liquid portion at a temperature in a range of 10 to 40° C.,
the work time being from the start of kneading the biphasic self-setting calcium phosphate powder portion and the biphasic self-setting calcium phosphate liquid portion to the setting of the biphasic self-setting calcium phosphate,
the biphasic self-setting calcium phosphate powder portion comprising tetracalcium phosphate and α-tricalcium phosphate,
the biphasic self-setting calcium phosphate liquid portion comprising a phosphoric acid aqueous solution containing a calcium component,
the calcium component contained in the biphasic self-setting calcium phosphate liquid portion comprising at least one selected from the group consisting of calcium hydroxide, calcium oxide, and calcium carbonate, and
the biphasic self-setting calcium phosphate liquid portion is undersaturated with respect to a calcium phosphate compound prior to kneading with the biphasic self-setting calcium phosphate powder portion,
wherein when a phosphorus concentration (mol/L) of the biphasic self-setting calcium phosphate liquid portion is taken along the x-axis and a calcium concentration (mol/L) of the biphasic self-setting calcium phosphate liquid portion is taken along the y-axis, the values (x, y) of the phosphorus concentration and the calcium concentration of the biphasic self-setting calcium phosphate liquid portion are included in the range of a triangle obtained by connecting the 3 points of (2.96, 1.09), (0.592, 0.218), and (7.38, 0.25) by straight lines, respectively.

2. The method for controlling the work time for shape-forming a biphasic self-setting calcium phosphate according to claim 1, wherein the biphasic self-setting calcium phosphate contains a sodium citrate compound comprising at least one selected from the group consisting of monosodium citrate, disodium citrate, and trisodium citrate; and the sodium citrate compound is added to at least one of the biphasic self-setting calcium phosphate powder portion and the biphasic self-setting calcium phosphate liquid portion.

3. The method for controlling the work time for shape-forming a biphasic self-setting calcium phosphate according to claim 1, wherein the biphasic self-setting calcium phosphate powder portion is prepared by grinding a heated mixture obtained by heating a mixture comprising calcium carbonate and dicalcium phosphates for 3 to 12 hours at a temperature range of 1200 to 1600° C., and the weight % of the calcium carbonate based on the sum of the weight of the calcium carbonate and the weight of the dicalcium phosphates is in a range of 26.9 to 42.3 weight %.

4. The method for controlling the work time for shape-forming a biphasic self-setting calcium phosphate according to claim 1, wherein the biphasic self-setting calcium phosphate powder portion is a solid solution comprising tetracalcium phosphate and α-tricalcium phosphate, and the weight fraction of α-tricalcium phosphate in the solid solution is in a range of 10 to 90%.

5. The method for controlling the work time for shape-forming a biphasic self-setting calcium phosphate according to claim 1, wherein the biphasic self-setting calcium phosphate liquid portion is a phosphoric acid aqueous solution containing calcium, and the concentration of calcium in the aqueous solution is in a range of $1.0 \times 10^{-3}$ mol/L to 1.1 mol/L, and the phosphorus concentration of the aqueous solution is in a range of 0.5 to 8 moL/L.

6. The method for controlling the work time for shape-forming a biphasic self-setting calcium phosphate according to claim 1, wherein the ratio of the weight of the biphasic self-setting calcium phosphate powder portion to the biphasic self-setting calcium phosphate liquid portion is in a range of 1.0 to 5.0.

7. The method for controlling the work time for shape-forming a biphasic self-setting calcium phosphate according to claim 1, wherein the biphasic self-setting calcium phosphate liquid portion is an aqueous solution containing 3 to 45 weight % of phosphoric acid.

\* \* \* \* \*